United States Patent
Munroe et al.

(10) Patent No.: US 6,482,609 B1
(45) Date of Patent: Nov. 19, 2002

(54) ISOLATED HUMAN EDG-4 RECEPTOR AND POLYNUCLETIDE ENCODING SAID RECEPTOR

(75) Inventors: Donald G. Munroe, Waterdown (CA); Rajender Kamboj, Mississauga (CA); Diana Peters, Toronto (CA); Fatemch Kooshesh, Etobicoke (CA); Tejal B. Vyas, Mississauga (CA); Ashwani K. Gupta, Mississauga (CA)

(73) Assignee: NPS Allelix Corporation, Mississauga (CA)

( * ) Notice: Subject to any disclaimer, the term of this patent is extended or adjusted under 35 U.S.C. 154(b) by 0 days.

(21) Appl. No.: 09/582,200

(22) PCT Filed: Dec. 30, 1998

(86) PCT No.: PCT/CA98/01195

§ 371 (c)(1), (2), (4) Date: Jul. 28, 2000

(87) PCT Pub. No.: WO99/35259

PCT Pub. Date: Jul. 15, 1999

Related U.S. Application Data

(60) Provisional application No. 60/070,185, filed on Dec. 30, 1997, provisional application No. 60/080,610, filed on Apr. 3, 1998, and provisional application No. 60/109,885, filed on Nov. 25, 1998.

(51) Int. Cl.[7] .......................... C12N 15/12; C12N 5/10; C12N 15/63; C07K 14/705
(52) U.S. Cl. ..................... 435/69.1; 435/71.1; 435/320; 435/471; 435/325; 435/252.2; 536/23.5; 536/23.4; 530/350
(58) Field of Search ............................... 435/69.1, 71.1, 435/320, 471, 325, 252.3; 536/23.5, 23.4; 530/350

(56) References Cited

U.S. PATENT DOCUMENTS 5,585,476 A 12/1996 MacLennan ............... 536/23.5

FOREIGN PATENT DOCUMENTS

WO 97 00952 1/1997
WO 98 53062 11/1998

OTHER PUBLICATIONS

An, S. EMBL/GenBank: Accession No. AF034780, Nov. 1997.*

Yamaguchi et al., "Molecular cloning of the novel human G protein–coupled receptor (GPCR) gene mapped on chromosome 9", Biochemical and Biophysical Research Communications, vol. 227, No. 2, Oct. 14, 1996, pp. 608–614.

Maclennan et al., "Cloning and characterization of a putative G–protein coupled receptor potentially involved in development", Molecular and Cellular Neurosciences, vol. 5, No. 3, Jun. 1994, pp. 201–209.

An et al., "Molecular cloning of the human Edg2 protein and its identification as a functional cellular receptor for lysophosphatidic acid", Biochemical and Biophysical Research Communications, vol. 231, Feb. 24, 1997, pp. 619–622.

Shatrov et al., "Sphingosine–1–phosphate mobilizes intracellular Calcium and activates transcription factor NF–KappaB in U937 Cells", Biochemical and Biophusical Research Communications, vol. 234, No. 1, May 8, 1997, pp. 121–124.

* cited by examiner

*Primary Examiner*—Prema Mertz
*Assistant Examiner*—Fozia Hamud
(74) *Attorney, Agent, or Firm*—Arent Fox Kintner Plotkin & Kahn

(57) ABSTRACT

A lysolipid receptor, a human EDG-4 receptor, a method of identifying lysolipid receptors involved in inflammatory response and the lysolipid receptors so identified, and a method of identifying ligands which interact with such lysolipid receptors.

16 Claims, 36 Drawing Sheets

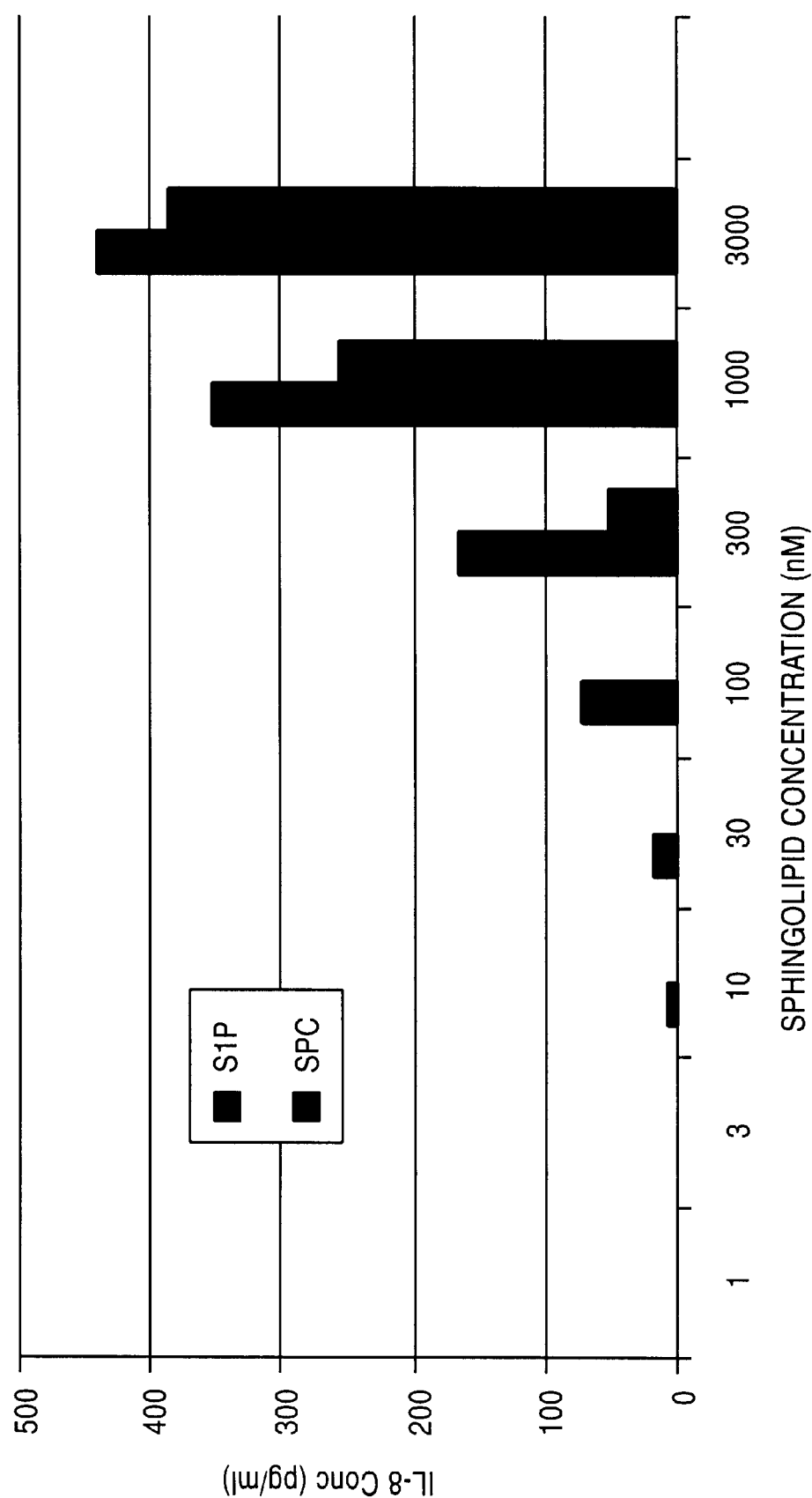

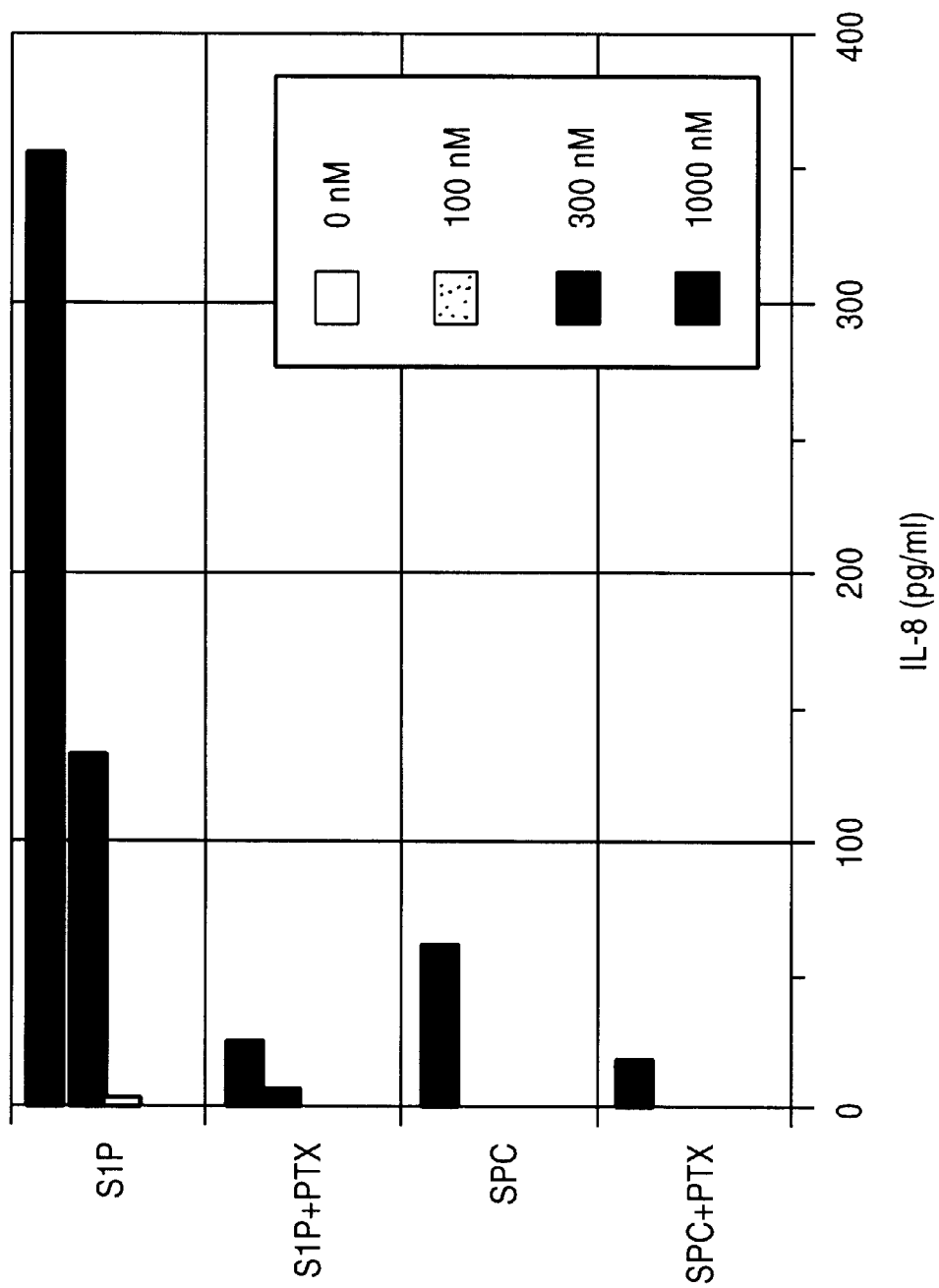

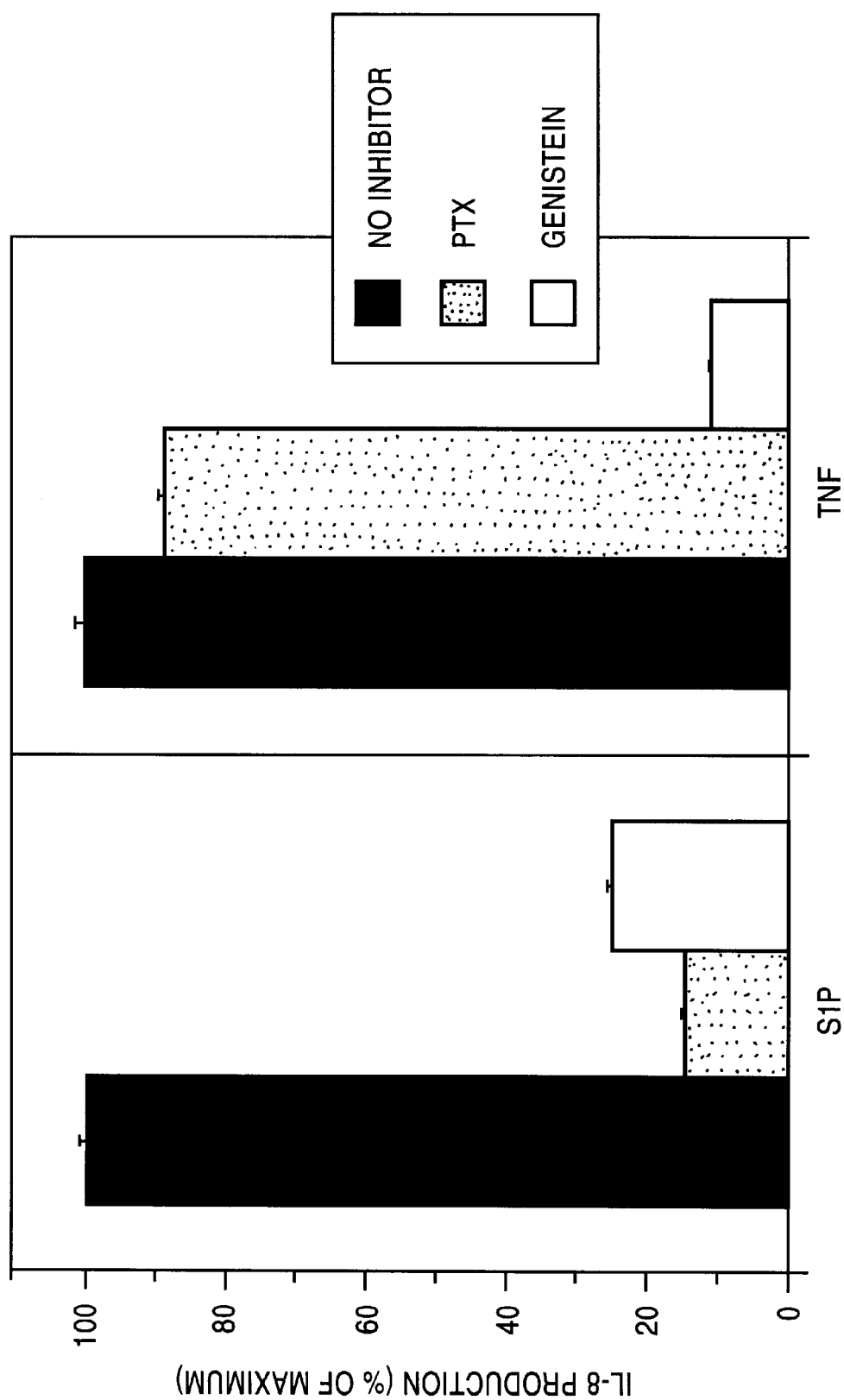

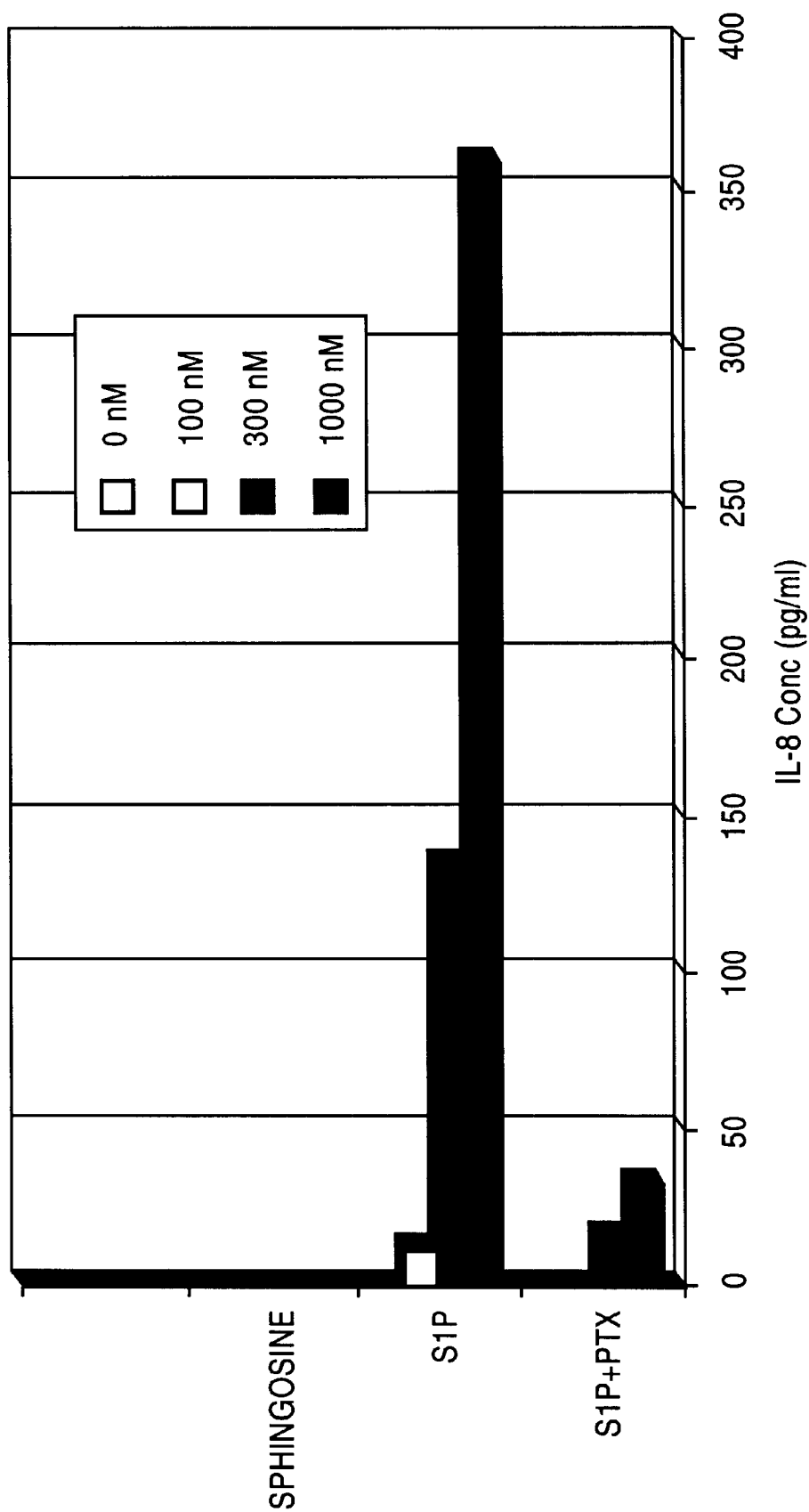

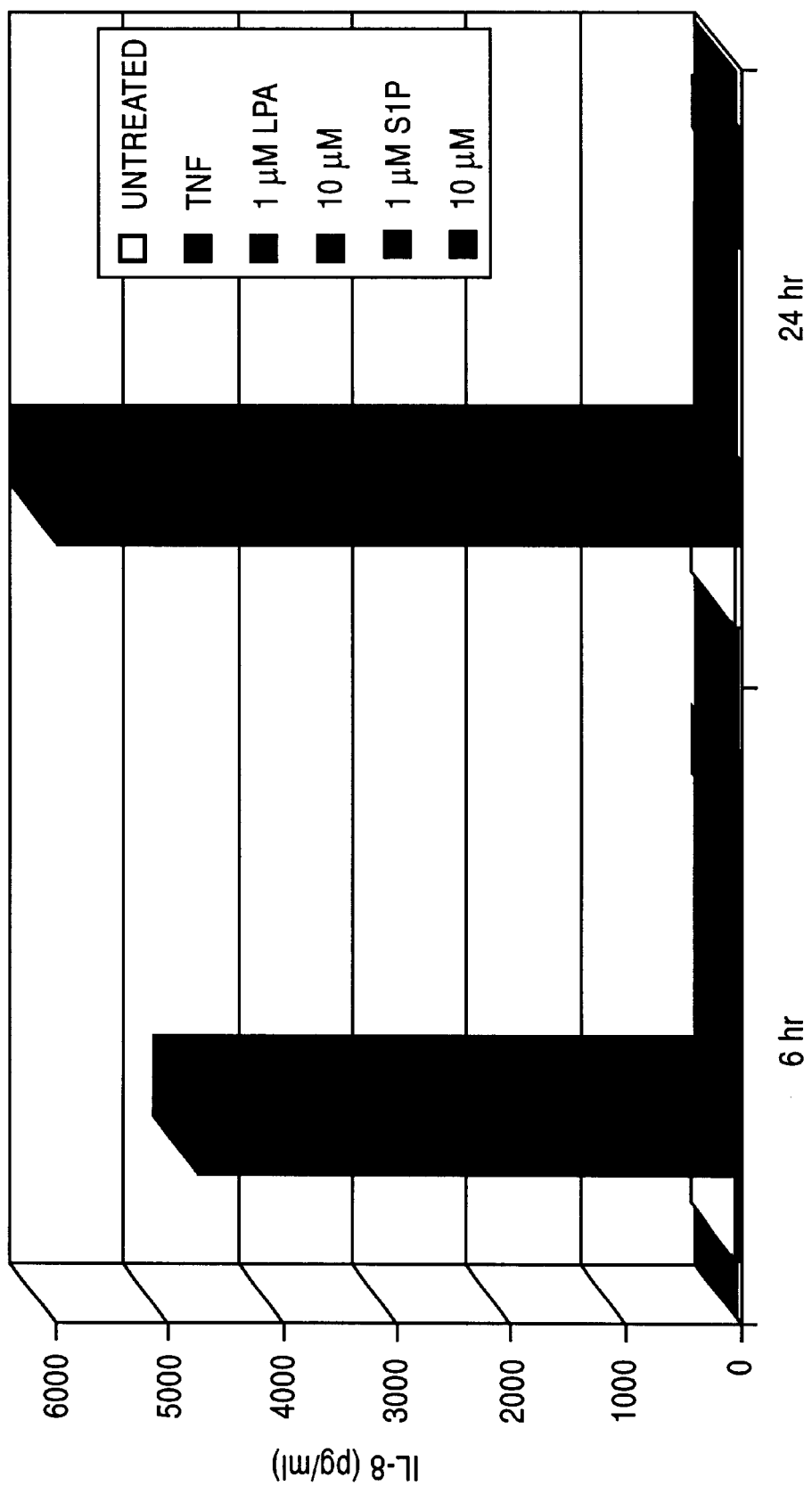

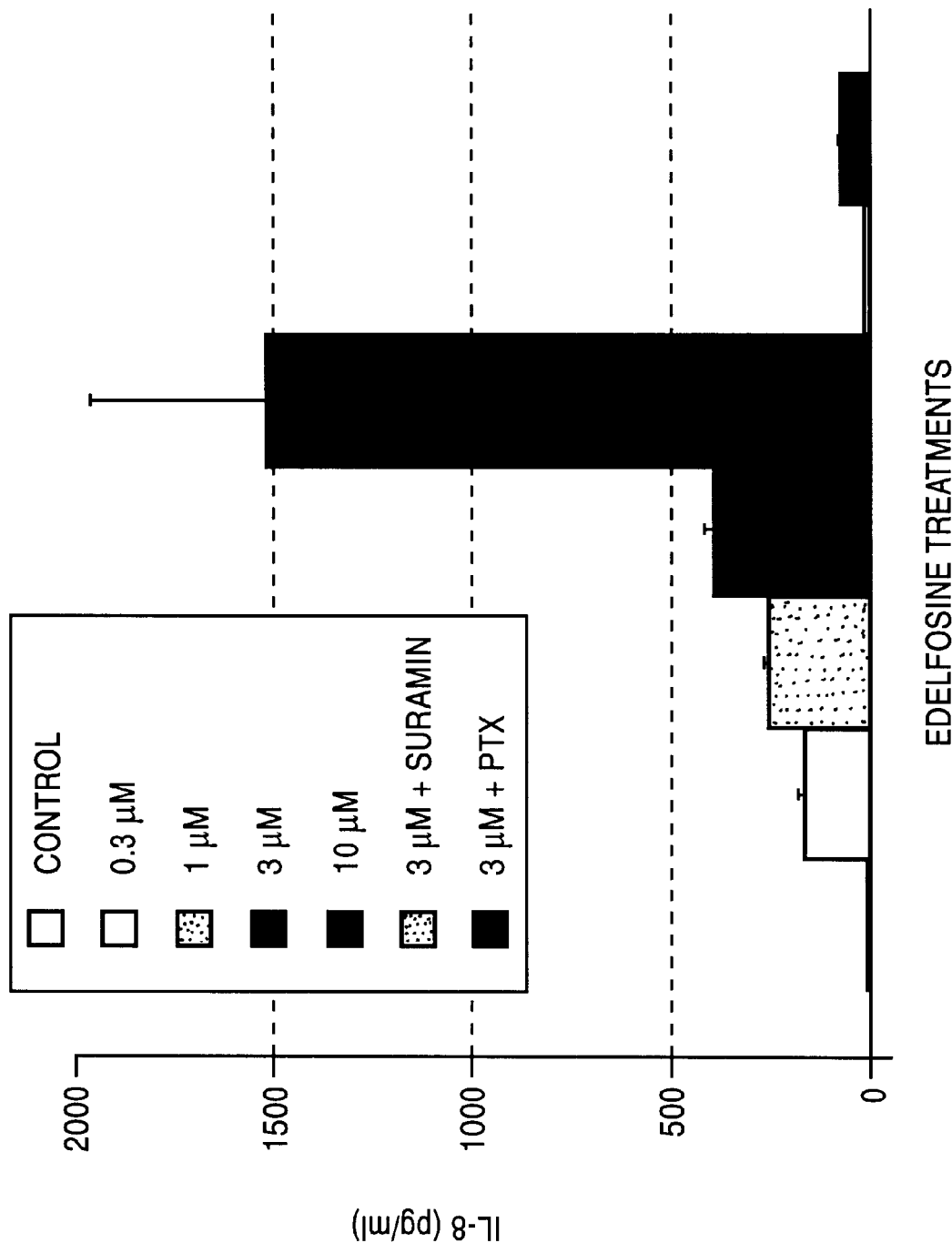

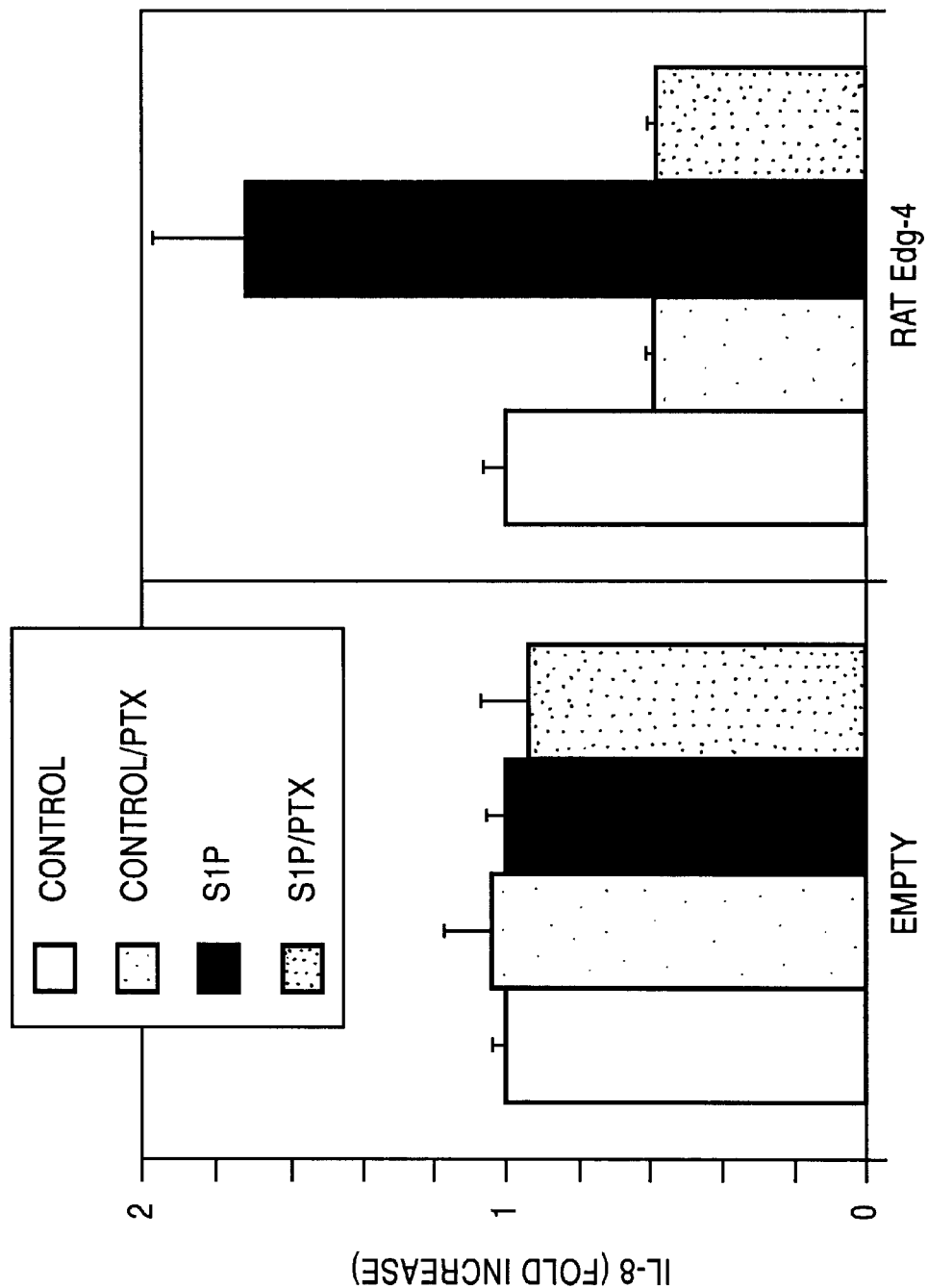

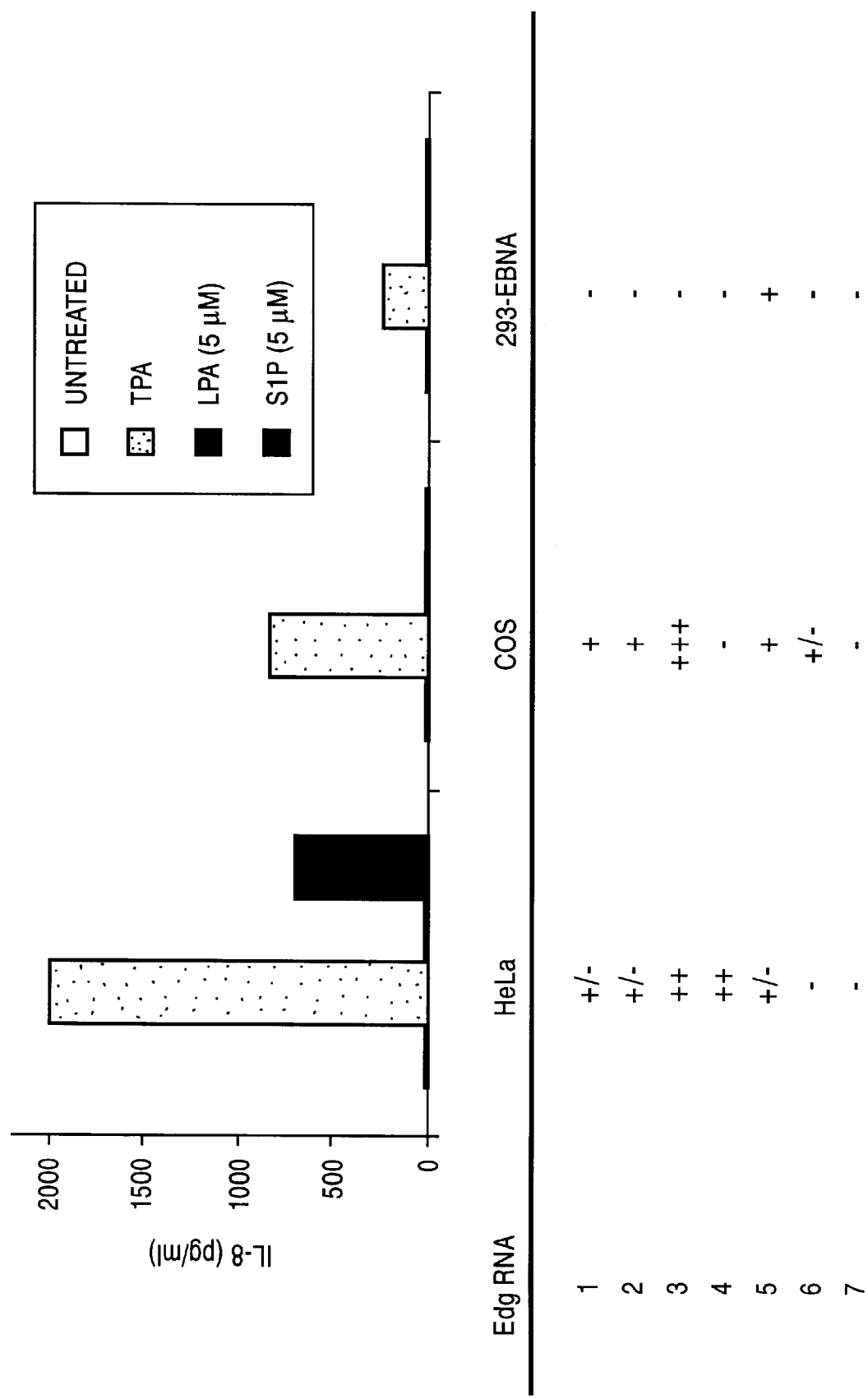

Fig.14

```
                              1                                                    50
SEQ ID NO: 5  AA834537   -------AAA GCCCCATGGC CCCAGCAGGC CTCTGAGCCC CACCATGGGC
SEQ ID NO: 6  AA804628   -------AAA GCCCCATGGC CCCAGCAGGC CTCTGAGCCC CACCATGGGC
SEQ ID NO: 7  AA827835   AGTTCTGAAA GCCCCATGGC CCCAGCAGGC CTCTGAGCCC CACCATGGGC 51                                                   100
              AA834537   AGCTTGTACT CGGAGTACCT GAACCCCAAC AAGGTCCAGG AACACTATAA
              AA804628   AGCTTGTACT CGGAGTACCT GAACCCCAAC AAGGTCCAGG AACACTATAA
              AA827835   AGCTTGTACT CGGAGTACCT GAACCCCAAC AAGGTCCAGG AACACTATAA 101                                                  150
              AA834537   TTATACCAAG GAGACGCTGG AAACGCAGGA GACGACCTCC CGCCAGGTGG
              AA804628   TTATACCAAG GAGACGCTGG AAACGCAGGA GACGACCTCC CGCCAGGTGG
              AA827835   TTATACCAAG GAGACGCTGG AAACGCAGGA GACGACCTCC CGCCAGGTGG 151                                                  200
              AA834537   CCTCGGCATT CATCGTCATC CTCTGTTGCG CCATTGTGGT GGAAAACCTT
              AA804628   CCTCGGCCTT CATCGTCATC CTCTGTTGCG CCATTGTGGT GGAAAACCTT
              AA827835   CCTCGGCCTT CATCGTCATC CTCTGTTGCG CCATTGTGGT GGAAAACCTT 201                                                  250
              AA834537   CTGGTGCTCA TTGCGGTGGC CCGAAACAGC AAGTTCCACT CGGCAATGTA
              AA804628   CTGGTGCTCA TTGCGGTGGC CCGAAACAGC AAGTTCCACT CGGCAATGTA
              AA827835   CTGGTGCTCA TTGCGGTGGC CCGAAACAGC AAGTTCCACT CGGCAATGTA 251                                                  300
              AA834537   CCTGTTTCTG GGCAACCTGG CCGCCTCCGA TCTACTGGCA GGCGTGGCCT
              AA804628   CCTGTTTCTG GGCAACCTGG CCGCCTCCGA TCTACTGGCA GGCGTGGCCT
              AA827835   CCTGTTTCTG GGCAACCTGG CCGCCTCCGA TCTACTGGCA GGCGTGG.CT 301                                                  350
              AA834537   TCGTAGCCAA TACCTTGCTC TCTGGCTCTG TCACGCTGAG GCTGACGCCT
              AA804628   TCGTAGCCAA TACCTTGCTC TCTGGCTCTG TCACGCTGAG GCTGACGCCT
              AA827835   TCGTAGCCAA TACCTTGCTC TCTGGCTCTG TCACGCTGAG GCTGACGCCT 351                                                  400
              AA834537   GTGCAGTGGT TTGCCCGGGA CGGTCTGCCT TCATCACGCT CTCGGCCTCT
              AA804628   GTGCAGTGGT TTGCCCGGGA C--------- ---------- ----------
              AA827835   GTGCAGTGGT TTGCCCGGGA ---------- ---------- ----------

401                                                  450
              AA834537   GTCTTCAGCC TCCTGGCCAT CGCCATTGAG CGCCACGTGG CCATTGCAAA
              AA804628   ---------- ---------- ---------- ---------- ----------
              AA827835   ---------- ---------- ---------- ---------- ----------

```
                                    M  G  S  L  Y  S  E  Y
     AAAGCCCCATGGCCCCAGCAGGCCTCTGAGCCCCACCATGGGCAGCTTGTACTCGGAGTA
  1  ---------+---------+---------+---------+---------+---------+  60
     TTTCGGGGTACCGGGGTCGTCCGGAGACTCGGGGTGGTACCCGTCGAACATGAGCCTCAT

L  N  P  N  K  V  Q  E  H  Y  N  Y  T  K  E  T  L  E  T  Q
     CCTGAACCCCAACAAGGTCCAGGAACACTATAATTATACCAAGGAGACGCTGGAAACGCA
 61  ---------+---------+---------+---------+---------+---------+ 120
     GGACTTGGGGTTGTTCCAGGTCCTTGTGATATTAATATGGTTCCTCTGCGACCTTTGCGT

E  T  T  S  R  Q  V  A  S  A  F  I  V  I  L  C  C  A  I  V
     GGAGACGACCTCCCGCCAGGTGGCCTCGGCCTTCATCGTCATCCTCTGTTGCGCCATTGT
121  ---------+---------+---------+---------+---------+---------+ 180
     CCTCTGCTGGAGGGCGGTCCACCGGAGCCGGAAGTAGCAGTAGGAGACAACGCGGTAACA

V  E  N  L  L  V  L  I  A  V  A  R  N  S  K  F  H  S  A  M
     GGTGGAAAACCTTCTGGTGCTCATTGCGGTGGCCCGAAACAGCAAGTTCCACTCGGCAAT
181  ---------+---------+---------+---------+---------+---------+ 240
     CCACCTTTTGGAAGACCACGAGTAACGCCACCGGGCTTTGTCGTTCAAGGTGAGCCGTTA

Y  L  F  L  G  N  L  A  A  S  D  L  L  A  G  V  A  F  V  A
     GTACCTGTTTCTGGGCAACCTGGCCGCCTCCGATCTACTGGCAGGCGTGGCCTTCGTAGC
241  ---------+---------+---------+---------+---------+---------+ 300
     CATGGACAAAGACCCGTTGGACCGGCGGAGGCTAGATGACCGTCCGCACCGGAAGCATCG

N  T  L  S  G  S  V  T  L  R  L  T  P  V  Q  W  F  A  R
     CAATACCTTGCTCTCTGGCTCTGTCACGCTGAGGCTGACGCCTGTGCAGTGGTTTGCCCG
301  ---------+---------+---------+---------+---------+---------+ 360
     GTTATGGAACGAGAGACCGAGACAGTGCGACTCCGACTGCGGACACGTCACCAAACGGGC

E  G  S  A  F  I  T  L  S  A  S  V  F  S  L  L  A  I  A  I
     GGAGGGCTCTGCCTTCATCACGCTCTCGGCCTCTGTCTTCAGCCTCCTGGCCATCGCCAT
361  ---------+---------+---------+---------+---------+---------+ 420
     CCTCCCGAGACGGAAGTAGTGCGAGAGCCGGAGACAGAAGTCGGAGGACCGGTAGCGGTA

E  R  H  V  A  I  A  K  V  K  L  Y  G  S  D  K  S  C  R  M
     TGAGCGCCACGTGGCCATTGCCAAGGTCAAGCTGTATGGCAGCGACAAGAGCTGCCGCAT
421  ---------+---------+---------+---------+---------+---------+ 480
     ACTCGCGGTGCACCGGTAACGGTTCCAGTTCGACATACCGTCGCTGTTCTCGACGGCGTA

L  L  L  I  G  A  S  W  L  I  S  L  V  L  G  G  L  P  I  L
     GCTTCTGCTCATCGGGGCCTCGTGGCTCATCTCGCTGGTCCTCGGTGGCCTGCCCATCCT
481  ---------+---------+---------+---------+---------+---------+ 540
     CGAAGACGAGTAGCCCCGGAGCACCGAGTAGAGCGACCAGGAGCCACCGGACGGGTAGGA

G  W  N  C  L  G  H  L  E  A  C  S  T  V  L  P  L  Y  A  K
     TGGCTGGAACTGCCTGGGCCACCTCGAGGCCTGCTCCACTGTCCTGCCTCTCTACGCCAA
541  ---------+---------+---------+---------+---------+---------+ 600
     ACCGACCTTGACGGACCCGGTGGAGCTCCGGACGAGGTGACAGGACGGAGAGATGCGGTT

H  Y  V  L  C  V  V  T  I  F  S  I  I  L  L  A  I  V  A  L
     GCATTATGTGCTGTGCGTGGTGACCATCTTCTCCATCATCCTGTTGGCCATCGTGGCCCT
601  ---------+---------+---------+---------+---------+---------+ 660
     CGTAATACACGACACGCACCACTGGTAGAAGAGGTAGTAGGACAACCGGTAGCACCGGGA

Y  V  R  I  Y  C  V  V  R  S  S  H  A  D  M  A  A  P  Q  T
     GTACGTGCGCATCTACTGCGTGGTCCGCTCAAGCCACGCTGACATGGCCGCCCCGCAGAC
661  ---------+---------+---------+---------+---------+---------+ 720
     CATGCACGCGTAGATGACGCACCAGGCGAGTTCGGTGCGACTGTACCGGCGGGGCGTCTG

L  A  L  L  K  T  V  T  I  V  L  G  V  F  I  V  C  W  L  P
SEQ ID NO:1
```

Fig.15A-2

```
        GCTAGCCCTGCTCAAGACGGTCACCATCGTGCTAGGCGTCTTTATCGTCTGCTGGCTGCC
721     ------------------------------------------------------------  780
        CGATCGGGACGAGTTCTGCCAGTGGTAGCACGATCCGCAGAAATAGCAGACGACCGACGG

A  F  S  I  L  L  L  D  Y  A  C  P  V  H  S  C  P  I  L  Y
        CGCCTTCAGCATCCTCCTTCTGGACTATGCCTGTCCCGTCCACTCCTGCCCGATCCTCTA
781     ------------------------------------------------------------  840
        GCGGAAGTCGTAGGAGGAAGACCTGATACGGACAGGGCAGGTGAGGACGGGCTAGGAGAT

K  A  H  Y  X  F  A  V  S  T  L  N  S  L  L  N  P  V  I  Y
        CAAAGCCCACTACYTTTTCGCCGTCTCCACCCTGAATTCCCTGCTCAACCCCGTCATCTA
841     ------------------------------------------------------------  900
        GTTTCGGGTGATGRAAAAGCGGCAGAGGTGGGACTTAAGGGACGAGTTGGGGCAGTAGAT

T  W  R  S  R  D  L  R  R  E  V  L  R  P  L  Q  C  W  R  P
        CACGTGGCGCAGCCGGGACCTGCGGCGGGAGGTGCTTCGGCCGCTGCAGTGCTGGCGGCC
901     ------------------------------------------------------------  960
        GTGCACCGCGTCGGCCCTGGACGCCGCCCTCCACGAAGCCGGCGACGTNACGACCGCCGG

G  V  G  V  Q  G  R  R  R  G  G  T  P  G  H  H  L  L  P  L
        GGGGGTGGGGGTGCAAGGACGGAGGCGGGGCGGGACCCCGGGCCACCACCTCCTGCCACT
961     ------------------------------------------------------------  1020
        CCCCCACCCCCACGTTCCTGCCTCCGCCCCGCCCTGGGGCCCGGTGGTGGAGGACGGTGA

R  S  S  S  L  E  R  G  M  H  M  P  T  S  P  T  F  L  E
        CCGCAGCTCCAGCTCCCTGGAGAGGGGCATGCACATGCCCACGTCACCCACGTTTCTGGA
1021    ------------------------------------------------------------  1080
        GGCGTCGAGGTCGAGGGACCTCTCCCCGTACGTGTACGGGTGCAGTGGGTGAAAAGACCT

G  N  T  V  V  *
        GGGCAACACGGTGGTCTGAGGGTGGGGGTGGACCAACAACCAGGCCAGGGCATAGGGGTT
1081    ------------------------------------------------------------  1140
        CCCGTTGTGCCACCAGACTCCCACCCCCACCTGGTTGTTGGTCCGGTCCCGTATCCCCAA

CATGGAAAGGCCACTGGGTGACCCCAAATA
1141    ------------------------------  1170
        GTACCTTTCCGGTGACCCACTGGGGTTTAT
```

Fig.15B-1 cDNA sequence of clone pC3-hedg4#36 encoding functional HEDG4 receptor protein.
(SEQ ID NO: 2)

```
      ATGGGCAGCTTGTACTCGGAGTACCTGAACCCCAACAAGGTCCAGGAACACTATAATTAT
  1   ------------+---------+---------+---------+---------+---------+   60
      TACCCGTCGAACATGAGCCTCATGGACTTGGGGTTGTTCCAGGTCCTTGTGATATTAATA

ACCAAGGAGACGCTGGAAACGCAGGAGACGACCTCCCGCCAGGTGGCCTCGGCCTTCATC
 61   ------------+---------+---------+---------+---------+---------+  120
      TGGTTCCTCTGCGACCTTTGCGTCCTCTGCTGGAGGGCGGTCCACCGGAGCCGGAAGTAG

GTCATCCTCTGTTGCGCCATTGTGGTGGAAAACCTTCTGGTGCTCATTGCGGTGGCCCGA
121   ------------+---------+---------+---------+---------+---------+  180
      CAGTAGGAGACAACGCGGTAACACCACCTTTTGGAAGACCACGAGTAACGCCACCGGGCT

AACAGCAAGTTCCACTCGGCAATGTACCTGTTTCTGGGCAACCTGGCCGCCTCCGATCTA
181   ------------+---------+---------+---------+---------+---------+  240
      TTGTCGTTCAAGGTGAGCCGTTACATGGACAAAGACCCGTTGGACCGGCGGAGGCTAGAT

CTGGCAGGCGTGGCCTTCGTAGCCAATACCTTGCTCTCTGGCTCTGTCACGCTGAGGCTG
241   ------------+---------+---------+---------+---------+---------+  300
      GACCGTCCGCACCGGAAGCATCGGTTATGGAACGAGAGACCGAGACAGTGCGACTCCGAC

ACGCCTGTGCAGTGGTTTGCCCGGGAGGGCTCTGCCTTCATCACGCTCTCGGCCTCTGTC
301   ------------+---------+---------+---------+---------+---------+  360
      TGCGGACACGTCACCAAACGGGCCCTCCCGAGACGGAAGTAGTGCGAGAGCCGGAGACAG

TTCAGCCTCCTGGCCATCGCCATTGAGCGCCACGTGGCCATTGCCAAGGTCAAGCTGTAT
361   ------------+---------+---------+---------+---------+---------+  420
      AAGTCGGAGGACCGGTAGCGGTAACTCGCGGTGCACCGGTAACGGTTCCAGTTCGACATA

GGCAGCGACAAGAGCTGCCGCATGCTTCTGCTCATCGGGGCCTCGTGGCTCATCTCGCTG
421   ------------+---------+---------+---------+---------+---------+  480
      CCGTCGCTGTTCTCGACGGCGTACGAAGACGAGTAGCCCCGGAGCACCGAGTAGAGCGAC

GTCCTCGGTGGCCTGCCCATCCTTGGCTGGAACTGCCTGGGCCACCTCGAGGCCTGCTCC
481   ------------+---------+---------+---------+---------+---------+  540
      CAGGAGCCACCGGACGGGTAGGAACCGACCTTGACGGACCCGGTGGAGCTCCGGACGAGG

ACTGTCCTGCCTCTCTACGCCAAGCATTATGTGCTGTGCGTGGTGACCATCTTCTCCATC
541   ------------+---------+---------+---------+---------+---------+  600
      TGACAGGACGGAGAGATGCGGTTCGTAATACACGACACGCACCACTGGTAGAAGAGGTAG

ATCCTGTTGGCCGTCGTGGCCCTGTACGTGCGCATCTACTGCGTGGTCCGCTCAAGCCAC
601   ------------+---------+---------+---------+---------+---------+  660
      TAGGACAACCGGCAGCACCGGGACATGCACGCGTAGATGACGCACCAGGCGAGTTCGGTG

GCTGACATGGCCGCCCCGCAGACGCTAGCCCTGCTCAAGACGGTCACCATCGTGCTAGGC
661   ------------+---------+---------+---------+---------+---------+  720
      CGACTGTACCGGCGGGGCGTCTGCGATCGGGACGAGTTCTGCCAGTGGTAGCACGATCCG
```

Fig.15B-2

```
       GTCTTTATCGTCTGCTGGCTGCCCGCCTTCAGCATCCTCCTTCTGGACTATGCCTGTCCC
721    ---------+---------+---------+---------+---------+---------+   780
       CAGAAATAGCAGACGACCGACGGGCGGAAGTCGTAGGAGGAAGACCTGATACGGACAGGG

GTCCACTCCTGCCCGATCCTCTACAAAGCCCACTACCTTTTCGCCGTCTCCACCCTGAAT
781    ---------+---------+---------+---------+---------+---------+   840
       CAGGTGAGGACGGGCTAGGAGATGTTTCGGGTGATGGAAAAGCGGCAGAGGTGGGACTTA

TCCCTGCTCAACCCCGTCATCTACACGTGGCGCAGCCGGGACCTGCGGCGGGAGGTGCTT
841    ---------+---------+---------+---------+---------+---------+   900
       AGGGACGAGTTGGGGCAGTAGATGTGCACCGCGTCGGCCCTGGACGCCGCCCTCCACGAA

CGGCCGCTGCAGTGCTGGCGGCCGGGGGTGGGGGTGCAAGGACGGAGGCGGGGCGGGACC
901    ---------+---------+---------+---------+---------+---------+   960
       GCCGGCGACGTCACGACCGCCGGCCCCCACCCCCACGTTCCTGCCTCCGCCCCGCCCTGG

CCGGGCCACCACCTCCTGCCACTCCGCAGCTCCAGCTCCCTGGAGAGGGGCATGCACATG
961    ---------+---------+---------+---------+---------+---------+  1020
       GGCCCGGTGGTGGAGGACGGTGAGGCGTCGAGGTCGAGGGACCTCTCCCCGTACGTGTAC

CCCACGTCACCCACGTTTCTGGAGGGCAACACGGTGGTCTGA
1021   ---------+---------+---------+---------+--   1062
       GGGTGCAGTGGGTGCAAAGACCTCCCGTTGTGCCACCAGACT
```

Fig.16A

```
  1  MGSLYSEYLN PNKVQEHYNY TKETLETQET TSRQVASAFI VILCCAIVVE
 51  NLLVLIAVAR NSKFHSAMYL FLGNLAASDL LAGVAFVANT LLSGSVTLRL
101  TPVQWFAREG SAFITLSASV FSLLAIAIER HVAIAKVKLY GSDKSCRMLL
151  LIGASWLISL VLGGLPILGW NCLGHLEACS TVLPLYAKHY VLCVVTIFSI
201  ILLAIVALYV RIYCVVRSSH ADMAAPQTLA LLKTVTIVLG VFIVCWLPAF
251  SILLLDYACP VHSCPILYKA HYXFAVSTLN SLLNPVIYTW RSRDLRREVL
301  RPLQCWRPGV GVQGRRRGGT PGHHLLPLRS SSSLERGMHM PTSPTFLEGN
351  TVV*
```

SEQ ID NO: 3

Fig.16B

Predicted amino acid sequence of HEDG4 polypeptide encoded by pC3-hedg4#36. (SEQ ID NO: 4)

```
  1  MGSLYSEYLN PNKVQEHYNY TKETLETQET TSRQVASAFI VILCCAIVVE

51  NLLVLIAVAR NSKFHSAMYL FLGNLAASDL LAGVAFVANT LLSGSVTLRL

101  TPVQWFAREG SAFITLSASV FSLLAIAIER HVAIAKVKLY GSDKSCRMLL

151  LIGASWLISL VLGGLPILGW NCLGHLEACS TVLPLYAKHY VLCVVTIFSI

201  ILLAVVALYV RIYCVVRSSH ADMAAPQTLA LLKTVTIVLG VFIVCWLPAF

251  SILLLDYACP VHSCPILYKA HYLFAVSTLN SLLNPVIYTW RSRDLRREVL

301  RPLQCWRPGV GVQGRRRGGT PGHHLLPLRS SSSLERGMHM PTSPTFLEGN

351  TVV
```

Fig. 17A

```
SEQ ID NO: 8 → HUMAN   1 MGSLYSEYLNPNKVQEHYNYTKETLETQETTSRQVASAFIVILCCAIVVE  50
                         || |||||||||  ||||||||||||||:  ||| ||.|||||:||||||||
SEQ ID NO: 9 → RAT     1 MGGLYSEYLNPEKVQEHYNYTKETLDMQETPSRKVASAFIIILCCAIVVE  50

HUMAN  51 NLLVLIAVARNSKFHSAMYLFLGNLAASDLLAGVAFVANTLLSGSVTLRL 100
                         ||||||||||||||||||||||||||||||||||||||||||||| ||| |
               RAT    51 NLLVLIAVARNSKFHSAMYLFLGNLAASDLLAGVAFVANTLLSGPVTLSL 100

HUMAN 101 TPVQWFAREGSAFITLSASVFSLLAIAIERHVAIAKVKLYGSDKSCRMLL 150
                         ||.||||||||||||||||||||||||||||||| ||||||||||||||:
               RAT   101 TPLQWFAREGSAFITLSASVFSLLAIAIERQVAIAKVKLYGSDKSCRMLM 150

HUMAN 151 LIGASWLISLVLGGLPILGWNCLGHLEACSTVLPLYAKHYVLCVVTIFSI 200
                         ||||||||||:|||||||||||||||||||||||||||||||||||||:
               RAT   151 LIGASWLISLILGGLPILGWNCLDHLEACSTVLPLYAKHYVLCVVTIFSV 200

HUMAN 201 ILLAIVALYVRIYCVVRSSHADMAAPQTLALLKTVTIVLGVFIVCWLPAF 250
                         |||||||||||||| ||||||||.| |||||||||||||||||||:|||||
               RAT   201 ILLAIVALYVRIYFVVRSSHADVAGPQTLALLKTVTIVLGVFIICWLPAF 250

HUMAN 251 SILLLDYACPVHSCPILYKAHYXFAVSTLNSLLNPVIYTWRSRDLRREVL 300
                         ||||||| ||| .||:|||||| .|||||||||||||||||||||||||||
               RAT   251 SILLLDSTCPVRACPVLYKAHYFFAFATLNSLLNPVIYTWRSRDLRREVL 300

HUMAN 301 RPLQCWRPGVGVQGRRRGGTPGHHLLPLRSSSSLERGMHMPTSPTFLEGN 350
                         ||| |||  |  |  |||| ||| ||||||||||||||||:|||||||||||
               RAT   301 RPLLCWRQGKGATG.RRGGNPGHRLLPLRSSSSLERGLHMPTSPTFLEGN 349

HUMAN 351 TVV* 353
                         |||
               RAT   350 TVV* 352
```

Fig.17B

Alignment of HEDG4 with pC3-hedg4#36 translation product and rat H218 (REDG4). Differences between pC3-hedg4#36 translation product and previously determined HEDG4 polypeptide are indicated in reverse text. Differences between rat and human edg-4 polypeptide sequences are shown in bold, shaded text.

```
                         1                                                          50
SEQ ID NO: 8   HEDG4     MGSLYSEYLN PNKVQEHYNY TKETLETQET TSRQVASAFI VILCCAIVVE
SEQ ID NO: 10  HEDG4#36  MGSLYSEYLN PNKVQEHYNY TKETLETQET TSRQVASAFI VILCCAIVVE
SEQ ID NO: 9   REDG4     MGGLYSEYLN PEKVQEHYNY TKETLDMQET PSRKVASAFI IILCCAIVVE 51                                                         100
               HEDG4     NLLVLIAVAR NSKFHSAMYL FLGNLAASDL LAGVAFVANT LLSGSVTLRL
               HEDG4#36  NLLVLIAVAR NSKFHSAMYL FLGNLAASDL LAGVAFVANT LLSGSVTLRL
               REDG4     NLLVLIAVAR NSKFHSAMYL FLGNLAASDL LAGVAFVANT LLSGPVTLSL 101                                                        150
               HEDG4     TPVQWFAREG SAFITLSASV FSLLAIAIER HVAIAKVKLY GSDKSCRMLL
               HEDG4#36  TPVQWFAREG SAFITLSASV FSLLAIAIER HVAIAKVKLY GSDKSCRMLL
               REDG4     TPLQWFAREG SAFITLSASV FSLLAIAIER QVAIAKVKLY GSDKSCRMLM 151                                                        200
               HEDG4     LIGASWLISL VLGGLPILGW NCLGHLEACS TVLPLYAKHY VLCVVTIFSI
               HEDG4#36  LIGASWLISL VLGGLPILGW NCLGHLEACS TVLPLYAKHY VLCVVTIFSI
               REDG4     LIGASWLISL TLGGLPILGW NCLDHLEACS TVLPLYAKHY VLCVVTIFSV 201                                                        250
               HEDG4     ILLAVVALYV RIYCVVRSSH ADMAAPQTLA LLKTVTIVLG VFIVCWLPAF
               HEDG4#36  ILLAVVALYV RIYCVVRSSH ADMAAPQTLA LLKTVTIVLG VFIVCWLPAF
               REDG4     ILLAIVALYV RIYFVVRSSH ADVAGPQTLA LLKTVTIVLG VFIICWLPAF 251                                                        300
               HEDG4     SILLLDYACP VHSCPILYKA HYXFAVSTLN SLLNPVIYTW RSRDLRREVL
               HEDG4#36  SILLLDYACP VHSCPILYKA HYLFAVSTLN SLLNPVIYTW RSRDLRREVL
               REDG4     SILLLDSTCP VRACPVLYKA HYPFAFATLN SLLNPVIYTW RSRDLRREVL 301                                                        350
               HEDG4     RPLQCWRPGV GVQGRRRGGT PGHHLLPLRS SSSLERGMHM PTSPTFLEGN
               HEDG4#36  RPLQCWRPGV GVQGRRRGGT PGHHLLPLRS SSSLERGMHM PTSPTFLEGN
               REDG4     RPLLCWRQGK GATGYRRGGN PGHRLLPLRS SSSLERGLHM PTSPTFLEGN

351
               HEDG4     TVV-
               HEDG4#36  TVV-
               REDG4     TVV-
```

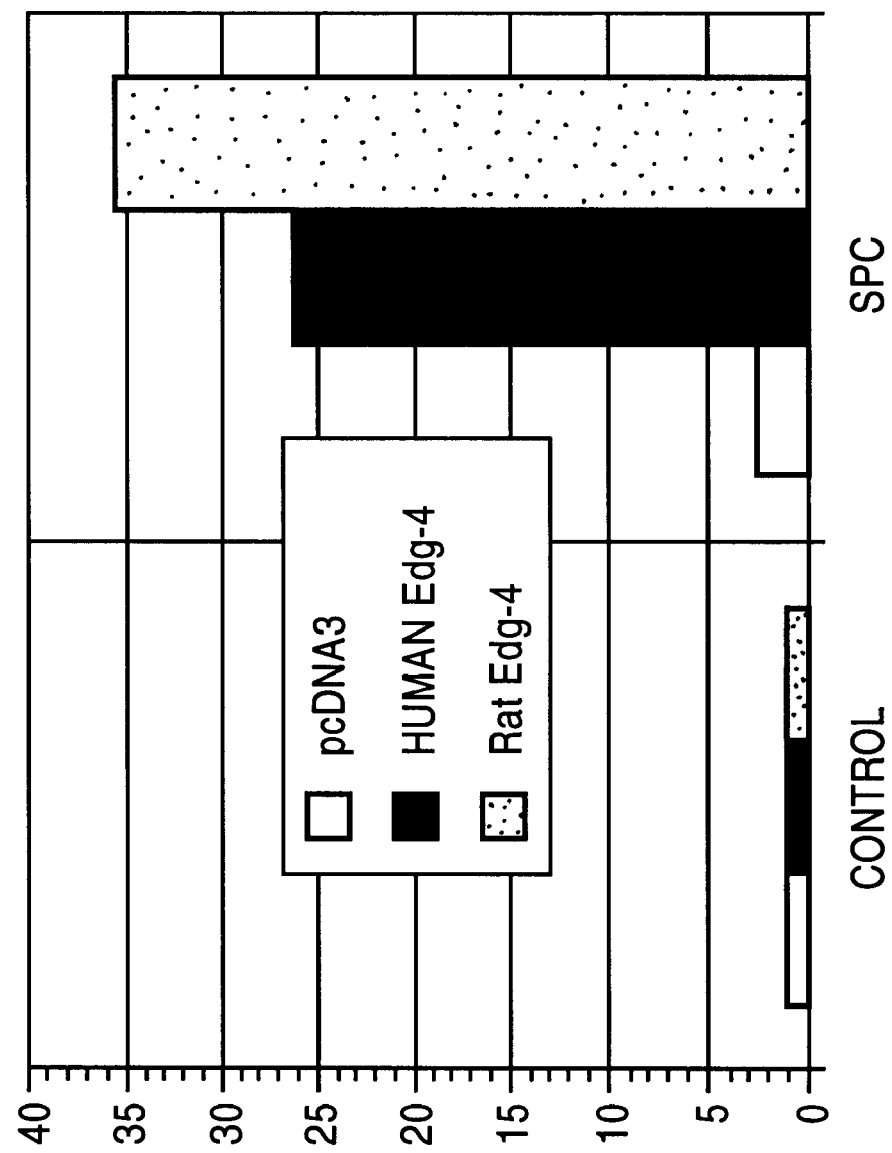

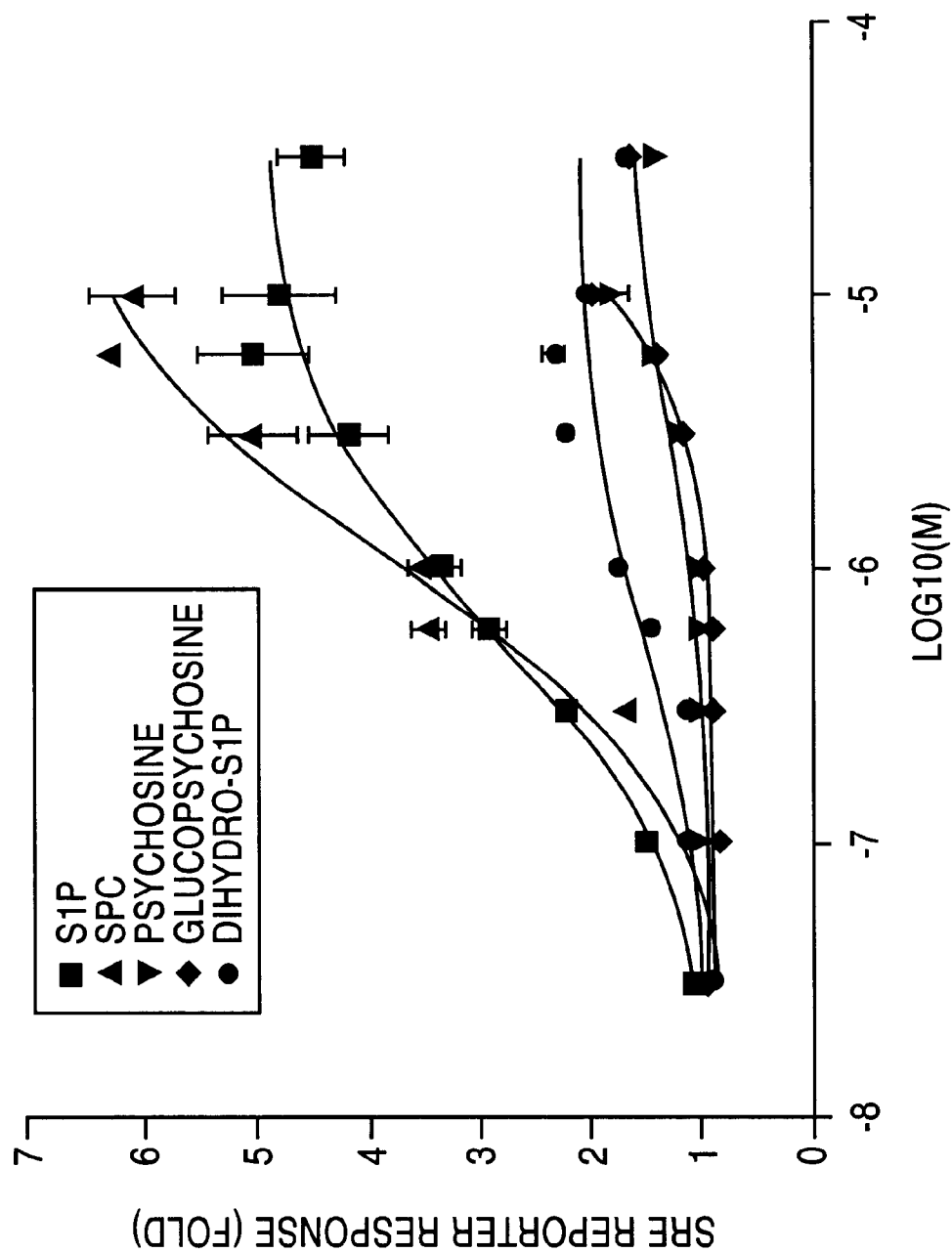

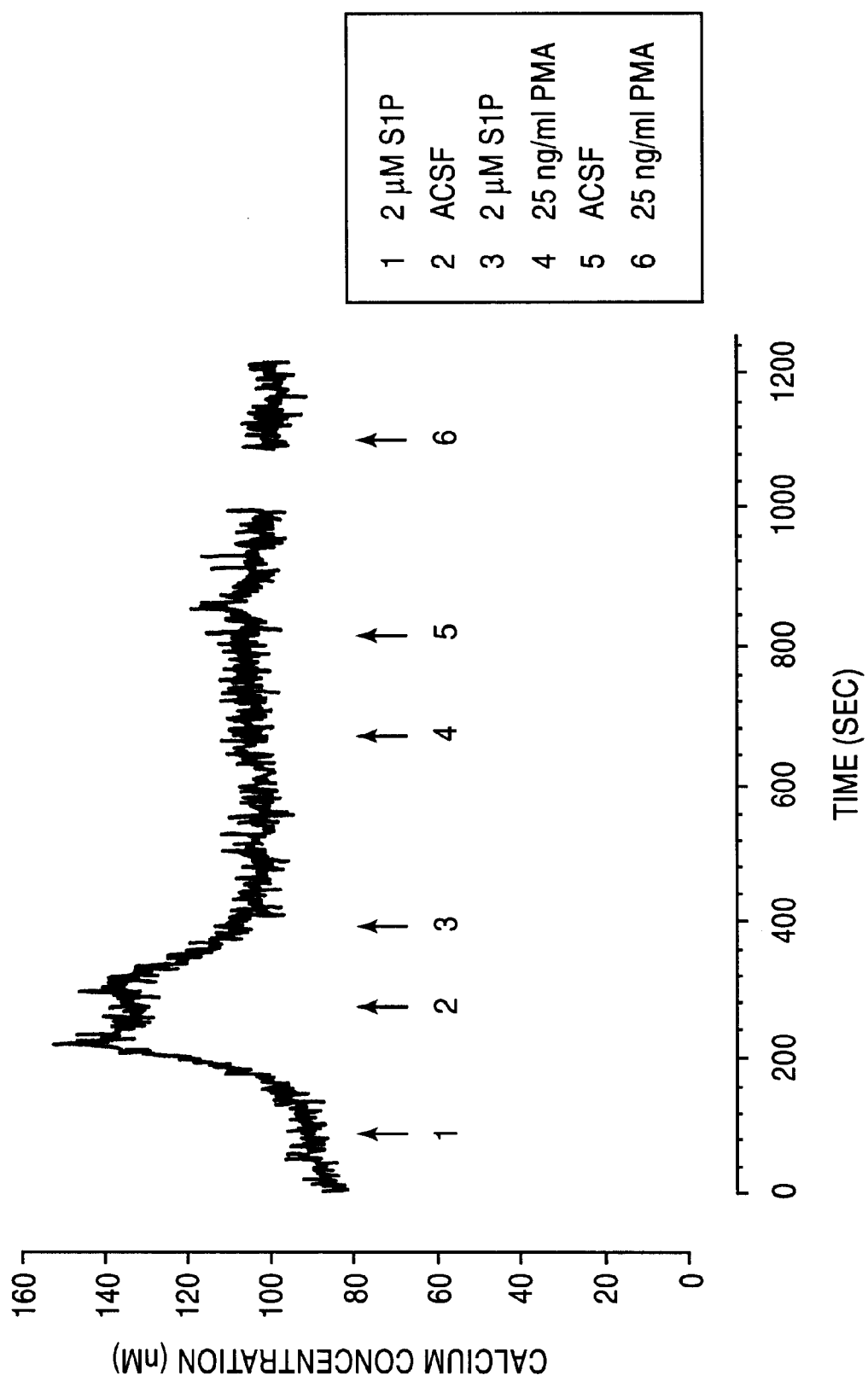

Fig.21

Human Edg-6 Amino Acid Sequence.

```
      MVIMGQCYYNETIGFFYNNSGKELSSHWRPKDVVVVALGLTVSVLVLLTNLLVIAAIASN
  1   ---------+---------+---------+---------+---------+---------+   60

RRFHQPIYYLLGNLAAADLFAGVAYLFLMFHTGPRTARLSLEGWFLRQGLLDTSLTASVA
 61   ---------+---------+---------+---------+---------+---------+  120

TLLAIAVERHRSVMAVQLHSRLPRGRVVMLIVGVWVAALGLGLLPAHSWHCLCALDRCSR
121   ---------+---------+---------+---------+---------+---------+  180

MAPLLSRSYLAVWALSSLLVFLLMVAVYTRIFFYVRRRVQRMAEHVSCHPRYRETTLSLV
181   ---------+---------+---------+---------+---------+---------+  240

KTVVIILGAFVVCWTPGQVVLLLDGLGCESCNVLAVEKYFLLLAEANSLVNAAVYSCRDA
241   ---------+---------+---------+---------+---------+---------+  300

EMRRTFRRLLCCACLRQSTRESVHYTSSAQGGASTRIMLPENGHPLMDSTL*
301   ---------+---------+---------+---------+----------+--   352
```

SEQ ID NO: 11

Fig.22-1  Human Edg-6 Sequence

```
       ATGGTCATCATGGGCCAGTGCTACTACAACGAGACCATCGGCTTCTTCTATAACAACAGT
   1   ------------+---------+---------+---------+---------+---------+  60
       TACCAGTAGTACCCGGTCACGATGATGTTGCTCTGGTAGCCGAAGAAGATATTGTTGTCA

GGCAAAGAGCTCAGCTCCCACTGGCGGCCCAAGGATGTGGTCGTGGTGGCACTGGGGCTG
  61   ------------+---------+---------+---------+---------+---------+ 120
       CCGTTTCTCGAGTCGAGGGTGACCGCCGGGTTCCTACACCAGCACCACCGTGACCCCGAC

ACCGTCAGCGTGCTGGTGCTGCTGACCAATCTGCTGGTCATAGCAGCCATCGCCTCCAAC
 121   ------------+---------+---------+---------+---------+---------+ 180
       TGGCAGTCGCACGACCACGACGACTGGTTAGACGACCAGTATCGTCGGTAGCGGAGGTTG

CGCCGCTTCCACCAGCCCATCTACTACCTGCTCGGCAATCTGGCCGCGGCTGACCTCTTC
 181   ------------+---------+---------+---------+---------+---------+ 240
       GCGGCGAAGGTGGTCGGGTAGATGATGGACGAGCCGTTAGACCGGCGCCGACTGGAGAAG

GCGGGCGTGGCCTACCTCTTCCTCATGTTCCACACTGGTCCCCGCACAGCCCGACTTTCA
 241   ------------+---------+---------+---------+---------+---------+ 300
       CGCCCGCACCGGATGGAGAAGGAGTACAAGGTGTGACCAGGGGCGTGTCGGGCTGAAAGT

CTTGAGGGCTGGTTCCTGCGGCAGGGCTTGCTGGACACAAGCCTCACTGCGTCGGTGGCC
 301   ------------+---------+---------+---------+---------+---------+ 360
       GAACTCCCGACCAAGGACGCCGTCCCGAACGACCTGTGTTCGGAGTGACGCAGCCACCGG

ACACTGCTGGCCATCGCCGTGGAGCGGCACCGCAGTGTGATGGCCGTGCAGCTGCACAGC
 361   ------------+---------+---------+---------+---------+---------+ 420
       TGTGACGACCGGTAGCGGCACCTCGCCGTGGCGTCACACTACCGGCACGTCGACGTGTCG

CGCCTGCCCCGTGGCCGCGTGGTCATGCTCATTGTGGGCGTGTGGGTGGCTGCCCTGGGC
 421   ------------+---------+---------+---------+---------+---------+ 480
       GCGGACGGGGCACCGGCGCACCAGTACGAGTAACACCCGCACACCCACCGACGGGACCCG

CTGGGGCTGCTGCCTGCCCACTCCTGGCACTGCCTCTGTGCCCTGGACCGCTGCTCACGC
 481   ------------+---------+---------+---------+---------+---------+ 540
       GACCCCGACGACGGACGGGTGAGGACCGTGACGGAGACACGGGACCTGGCGACGAGTGCG

ATGGCACCCCTGCTCAGCCGCTCCTATTTGGCCGTCTGGGCTCTGTCGAGCCTGCTTGTC
 541   ------------+---------+---------+---------+---------+---------+ 600
       TACCGTGGGGACGAGTCGGCGAGGATAAACCGGCAGACCCGAGACAGCTCGGACGAACAG

TTCCTGCTCATGGTGGCTGTGTACACCCGCATTTTCTTCTACGTGCGGCGGCGAGTGCAG
 601   ------------+---------+---------+---------+---------+---------+ 660
       AAGGACGAGTACCACCGACACATGTGGGCGTAAAAGAAGATGCACGCCGCCGCTCACGTC

CGCATGGCAGAGCATGTCAGCTGCCACCCCCGCTACCGAGAGACCACGCTCAGCCTGGTC
 661   ------------+---------+---------+---------+---------+---------+ 720
       GCGTACCGTCTCGTACAGTCGACGGTGGGGGCGATGGCTCTCTGGTGCGAGTCGGACCAG

AAGACTGTTGTCATCATCCTGGGGGCGTTCGTGGTCTGCTGGACACCAGGCCAGGTGGTA
 721   ------------+---------+---------+---------+---------+---------+ 780
       TTCTGACAACAGTAGTAGGACCCCCGCAAGCACCAGACGACCTGTGGTCCGGTCCACCAT

CTGCTCCTGGATGGTTTAGGCTGTGAGTCCTGCAATGTCCTGGCTGTAGAAAAGTACTTC
 781   ------------+---------+---------+---------+---------+---------+ 840
       GACGAGGACCTACCAAATCCGACACTCAGGACGTTACAGGACCGACATCTTTTCATGAAG
```

SEQ ID NO:12

Fig.22-2

```
        CTACTGcTGGCCGAGGCCAACTCACTGGTCAATGCTGCTGTGTACTCTTGCCGAGATGCT
841     ---------+---------+---------+---------+---------+---------+   900
        GATGACgACCGGCTCCGGTTGAGTGACCAGTTACGACGACACATGAGAACGGCTCTACGA

GAGATGCGCCGCACCTTCCGCCGCCTTCTCTGCTGCGCGTGCCTCCGCCAGTCCACCCGC
901     ---------+---------+---------+---------+---------+---------+   960
        CTCTACGCGGCGTGGAAGGCGGCGGAAGAGACGACGCGCACGGAGGCGGTCAGGTGGGCG

GAGTCTGTCCACTATACATCCTCTGCCCAGGGAGGTGCCAGCACTCGCATCATGCTTCCC
961     ---------+---------+---------+---------+---------+---------+   1020
        CTCAGACAGGTGATATGTAGGAGACGGGTCCCTCCACGGTCGTGAGCGTAGTACGAAGGG

GAGAACGGCCACCCACTGATGGACTCCACCCTTTAG
1021    ---------+---------+---------+------   1056
        CTCTTGCCGGTGGGTGACTACCTGAGGTGGGAAATC
```

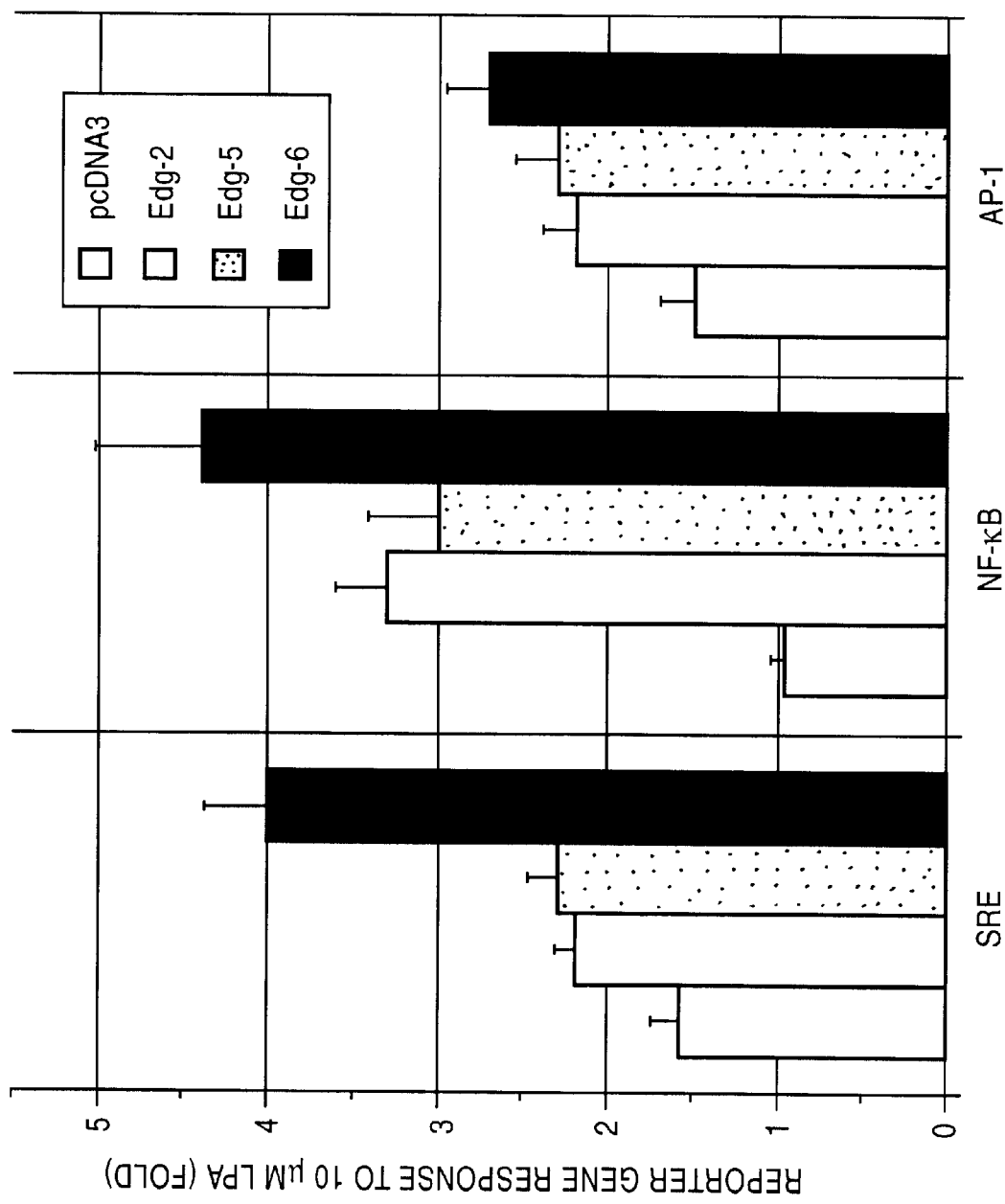

ISOLATED HUMAN EDG-4 RECEPTOR AND POLYNUCLETIDE ENCODING SAID RECEPTOR

This application is a 371 of WO 99/35259 filed on Dec. 30, 1998, which claims priority from provisioned application No. 60/070185, filed Dec. 30, 1997 which claims priority from provisioned application No. 60/080,610 filed Apr. 3, 1998 which claims priority from provisional application No. 60/109,885 filed Nov. 25, 1998.

FIELD OF THE INVENTION

The present invention is in the field of molecular biology. More particularly, the present invention relates to a novel lysolipid receptor, a human EDG-4 receptor, a method of identifying lysolipid receptors involved in inflammatory response and the lysolipid receptors so identified, and a method of identifying ligands which interact with such lysolipid receptors.

BACKGROUND OF THE INVENTION (a) EDG Receptors

EDG receptors have been grouped with orphan receptors because their endogenous ligands are not known (for example see Hla T and Maciag T (1990) J Biol. Chem. 265:93018–13; U.S. Pat. No. 5,585,476). Recently, however, lysophosphatidic acid (LPA) has been demonstrated to be the endogenous ligand for the EDG-2 receptor (Hecht et al. (1996) J. Cell. Biol. 135: 1071–1083; An et al. (1997) Biochem. Biophys. Res. Comm. 213: 619–622).

The EDG receptors are seven transmembrane G protein coupled receptors (T7Gs or GPCRs). GPCRs are so named because of their seven hydrophobic domains of 20–30 amino acids which span the plasma membrane and form a bundle of antiparallel α helices. These transmembrane segments (TMS) are designated by roman numerals I–VII and account for structural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. The activated receptor, in turn, interacts with an intracellular G-protein complex which mediates further intracellular signaling activities such as the production of second messengers such as cyclic AMP (cAMP), phospholipase C, inositol triphosphate, activation of protein kinases, alteration in the expression of specific genes.

When the receptor is activated by the binding of a ligand, the conformation of the receptor changes allowing it to interact with and activate a G protein. The activated G protein causes a molecule of guanosine diphoshate (GDP), that is bound to the surface of the G protein, to be replaced with a molecule of guanosine triphosphate (GTP), which causes another alteration in the conformation of the G protein. With GTP bound to its surface the G protein can regulate the activity of an effector. These effectors include enzymes such as adenylyl cyclase and phospholipase C and certain transport protein and ion channels such as calcium ions, potassium ions or sodium ions.

GPCRs are expressed and activated during numerous developmental and disease processes. Identification of a novel GPCR provides the opportunity to diagnose or intervene in such processes. The receptor can be used in screening assays to identify physiological or pharmaceutical molecules which trigger, prolong or inhibit a receptor's activity or a differentially modulate distinct intracellular pathways which are controlled by GPCRs. However, for many of the GPCRs (such as the EDG receptors) the biological processes mediated by the receptor are currently unknown. There exists a need therefore for methods to identify the biological processes mediated by these GPCRs and also for methods of identifying other GPCRs that may be involved in these processes.

Because there are diverse functions of GPCRs, it is not surprising that there are a number of therapeutic drugs that act by modifying the function of GPCRs. Therapeutic drugs which modify the GPCRs are particularly attractive because of the ability to design such drugs with particular specificity so that they turn on or off specific receptors and their signaling pathways.

(b) Lysophogpholinids and Inflammation

LPA is a naturally-occurring agonist of the EDG-2 receptor (Hecht et al. J Cell Biol 135: 1071, 1996). LPA, and many other lysophospholipids, are produced by activated platelets as a consequence of inflammation-related intracellular signal transduction accompanying aggregation and thrombus formation. Similar inflammatory pathways occur in many cell types, and typically lead to production of LL and other lipid mediators within seconds to minutes, and activation of new gene expression within minutes to hours.

A number of lysop pholipids have been studied to determine their biological effects. For example, the lysophospholipd sphingosine-1-phosphate (S1P) appears to play a role in a number of CNS-related biological processes. These include apoptosis, mitogenesis and cytoskeletal reorganization. S1P has been proposed to mediate at least some of the biological functions of PDGF and NGF. The former is a growth hormone with potent mitogenic and wound-healing activity. The latter is a neurotrophic factor, which has also been proposed to play a role in neuropathic pain.

In addition, it has been reported that there is activation of NF-κB by S1P in U937 cells; however, the authors assumed that S1P was an intracellular second messenger, and no attempt was made to determine whether this response was receptor-mediated. Furthermore, the functional relevance of NF-κB activation was not tested, e.g. by examining the possible upregulation of inflammatory cytokines, adhesion molecules or other NF-κB-dependent genes. If multiple receptors for S1P exist, the finding of NF-κB activation offers no utility by itself, since one, several, or all of the receptors might respond through NF-κB.

Moreover, direct modulation of NF-κB activation cascades has been proposed as a therapeutic mechanism for inflammation or apoptosis. However, NF-κB plays a vital role in innate immunity against ubiquitous microbial pathogens and in mobilizing the antigen-specific immune system. Therefore, rather than targeting this irreplaceable defense system, it would be preferred to instead block inappropriate activation of NF-κB by specific inflammatory or apoptotic signaling events. Accordingly, it is highly desireable to design therapeutic agents which could modulate NF-κB activation and thereby prevent unwanted apoptosis or thereby enhance immune function in immunocompromised hosts via a receptor modulated pathway.

SUMMARY OF THE INVENTION

It has now been discovered that there are LL/EDG receptors which are involved in an inflammatory response signaling pathway and an apoptotic signaling pathway. In particular, it has been discovered that the EDG-2, EDG-3, EDG-4, EDG-5 and EDG-6 receptors activate NF-κB and/or the production of IL-8. Accordingly, the present invention provides a link between NF-κB activation and edg receptors and hence a means for controlling NF-κB activation and thereby for controlling apoptosis and inflammatory responses.

In an aspect of the present invention, it has been discovered that agonists to the EDG-2, EDG-5 and EDG-6 receptors result in activation/production of NF-κB and/or IL-8. In particular, it has been discovered that LPA will act as an agonist to the EDG-2, EDG-5 and EDG-6 receptors resulting in activation/production of NF-κB and/or IL-8.

In another aspect of the present invention, it has been discovered that agonists to the EDG-3 and EDG-4 receptors result in activation/production of NF-κB and/or IL-8. In particular, it has been discovered that S1P and SPC will act as an agonist to the EDG-3 and EDG-4 receptor resulting in activation/production of NF-κB and/or IL-8.

In another aspect of the present invention there is provided isolated polynucleotides encoding the human EDG-4 receptor. The isolated polynucleotides may be either cDNA or genomic clones.

In particular, the present invention provides an isolated nucleotide sequence selected from the group consisting of:
a) the nucleotide sequence comprising nucleotides 38–1099 of FIG. 15A (SEQ ID NO:1);
(b) the nucleotide sequence of FIG. 15B (SEQ ID NO:2);
(c) a nucleotide sequence with at least about 95% sequence identity to (a) or (b) and which hybridizes under stringent conditions to sequences (a) and (b), respectively;
(d) a nucleotide sequence which encodes the amino acid sequence of FIG. 16A (SEQ ID NO:3) for the human EDG-4 receptor; and
(e) a nucleotide sequence which encodes the amino acid sequence of FIG. 16B (SEQ ID NO:4) for the human EDG-4 receptor.

There is also provided: expression vectors; host cells; purified amino acid sequences; complementary nucleic acid sequences; biologically active fragments; and hybridization probes, for such nucleotide sequences and their encoded amino acid sequences.

In another aspect of the present invention, there is provided a method of determining whether a DNA sequence encodes edg receptors that are involved in inflammatory response by measuring the induction of NF-κB and/or IL-8 upon activation by a suitable ligand.

In another aspect of the present invention, there is provided a method of determining whether a DNA sequence encodes an edlfosine receptor that is involved in inflammatory response by measuring the induction of NF-κB and/or IL-8 activation by a suitable ligand, including edelfosine.

In another aspect of the present invention, there is provided a method of identifying ligands that interact with edg or lysolipid receptors that are involved in inflammatory response. In particular, the present invention provides a method of identifying ligands which interact with edg or lysolipid receptors by measuring the induction or lack of induction of NF-κB and/or IL-8.

In another aspect of the present invention, there is provided a method of modulating or treating an inflammatory process condition in a subject by administering an effective amount of a pharmaceutical composition comprising an agonist or antagonist of an NF-κB and/or IL-8 modulated EDG or lysolipid receptor and a pharmaceutically acceptable excipient, for upregulation or downregulation of the inflammatory process, respectively. In particular, agonists and antagonists of the EDG-2, EDG-3, EDG-4, EDG-5 and/or EDG-6 receptor are applicable.

In another aspect of the present invention, there is provided a method of modulating an immune response in a subject by administering an effective amount of a pharmaceutical composition comprising an agonist or antagonist of an NF-κB and/or IL-8 modulated EDG or lysolipid receptor and a pharmaceutically acceptable excipient, for upregulation or downregulation of the immune response, respectively. In particular, agonists and antagonists of the EDG-2, EDG-3, EDG-4, EDG-5 and/or EDG-6 receptor are applicable.

In another aspect of the present invention, there is provided a method of controlling apoptosis by activating an EDG or lysolipid receptor which receptor activates the induction of NF-κB. In particular, by modulating the EDG-2, EDG-3, EDG-4, EDG-5 and/or EDG-6 receptor via agonists or antagonists there is provided a method of controlling apoptosis.

An EDG receptor herein refers to any receptor with at least 27–30% identity, preferably at least 30–35% identity, more preferably at least 35–40% identity, even more preferably at least 40–45% and most preferably at least 45–50% identity with each other. As is known in the art, the percentage identity of the amino acid sequences of related receptors is generally greater in the same species than in different species.

BRIEF DESCRIPTION OF THE FIGURES

The following figures will now be used to describe the invention in more detail.

FIG. 2A illustrates the concentration dependent IL-8 response to S1P and SPC in HeLa cells.

FIG. 2B illustrates the concentration-dependent IL-8 response to S1P and SPC in HeLa cells and the PTX-sensitivity of this response.

FIG. 3 illustrates the IL-8 response to S1P and TNF-α in HeLa cells and the PTX- and genistein sensitivity of this response.

FIG. 4A illustrates the concentration-dependent IL-8 response to S1P, sphingosine and sphingomyelin in HeLa cells.

FIG. 5 illustrates the time- and concentration-dependent IL-8 response to TNF-α, S1P and LPA in HL-60 cells.

FIG. 9 illustrates the IL-8 response to edelfosine in HeLa cells and the PTX- and suramin sensitivity of this response.

FIG. 10A illustrates the IL-8 response to S1P in 293-EBNA cells transfected with rat EDG-4 expression plasmid and the PTX sensitivity of this response.

FIG. 10B illustrates the expression of endogenous edg receptors in HeLa, COS and 293-EBNA cells.

FIG. 14 shows a multiple alignment of EST sequences representing the 5' end of the open reading frame of human EDG-4 cDNA. Sequences were aligned using the PILEUP program from the Wisconsin Package Version 9.0, Genetics Computer Group (GCG), Madison, Wis. The predicted translation start of human EDG-4, based on similarity to the rat translation start site, begins at nt 45 of the multiple alignment.

FIG. 15A, SEQ ID NO: 1, shows human EDG-4 cDNA and EDG-4 predicted amino acid sequence. The cDNA sequence was derived from clones pC3-hedg4#5 and pC3-hedg4#36 isolated by PCR from human lung fibroblast cell line WI-38 cDNA library (Origene Technologies Inc.).

FIG. 15B, SEQ ID NO: 2, shows human EDG-4 cDNA of clone pC3-Hedg4#36.

FIG. 16A, SEQ ID NO: 3, shows the amino acid sequence and features of the predicted polypeptide product of human EDG-4 cDNA of FIG. 15A.

FIG. 16B, SEQ ID NO: 4, shows the amino acid sequence of the EDG-4 polypeptide encoded by pC3-hEdg-4#36.

FIG. 17A shows the GAP alignment of the predicted human vs rat EDG-4 polypeptides. The predicted amino acid sequences of two polypeptides were aligned using the GCG GAP program.

FIG. 17B shows the alignment of the amino acid sequences of EDG-4 as derived from the clones pC3-Hedg4#5 and pC3-Hedg4#36 (FIG. 16A) with pC3-Hedg4#36 (FIG. 16B) and with rat EDG-4/H218 using the PILEUP program.

FIG. 18A illustrates the SRE reporter response to SPC in 293-EBNA cells cotransfected with a human or rat edg4 expression plasmid and an SRE reporter plasmid.

FIG. 18B illustrates the concentration-dependence of SRE response to S1P analogs in EDG-4 transfected cells.

FIG. 19 illustrates the incellular calcium response to S1P in cells transfected with the empty expression vector pcDNA3.

FIG. 21 illustrates the amino acid sequence for human EDG-6 receptor.

FIG. 22 illustrates the cDNA sequence for human EDG-6 receptor.

FIG. 23 illustrates that the three LPA receptor subtypes signal through NF-B and AP-1 genes.

DETAILED DESCRIPTION OF THE INVENTION

The EDG receptors are characterized by structural features common to the G-protein coupled receptor class, including seven transmembrane regions, and by the functional properties of binding lysophospholipids or lysophingolipids selectively. When expressed functionally in a host cell, i.e., in operable linkage with a responsive second messenger system the EDG receptors are capable further of responding to lysophingolipid or binding by signal transduction.

In the present invention it has been discovered that EDG receptors are involved in an inflammatory response signaling pathway and an apoptotic signaling pathway by the activation of NF-κB and production of IL-8.

It has also been discovered that endogenous LL receptors in HeLa cells can be activated to induce NF-κB/IL-8 and that an edelfosine receptor in HeLa cells can be activated to induce NF-κB/IL-8.

Functional assays were developed to identify receptors as NF-κB inducing receptors, in particular, to identify lysolipid (LL) receptors, EDG receptors and edelfosine receptors. In particular, assays were developed to measure NF-κB, IL-8 or IL-6 production.

With respect to the LL receptor(s) and edelfosine receptor (s), an assay was developed to determine the response of HeLa cells to LL (including S1P and LPA) and edelfosine, respectively, to induce NF-κB/IL-8 activation/production.

Figure 25:
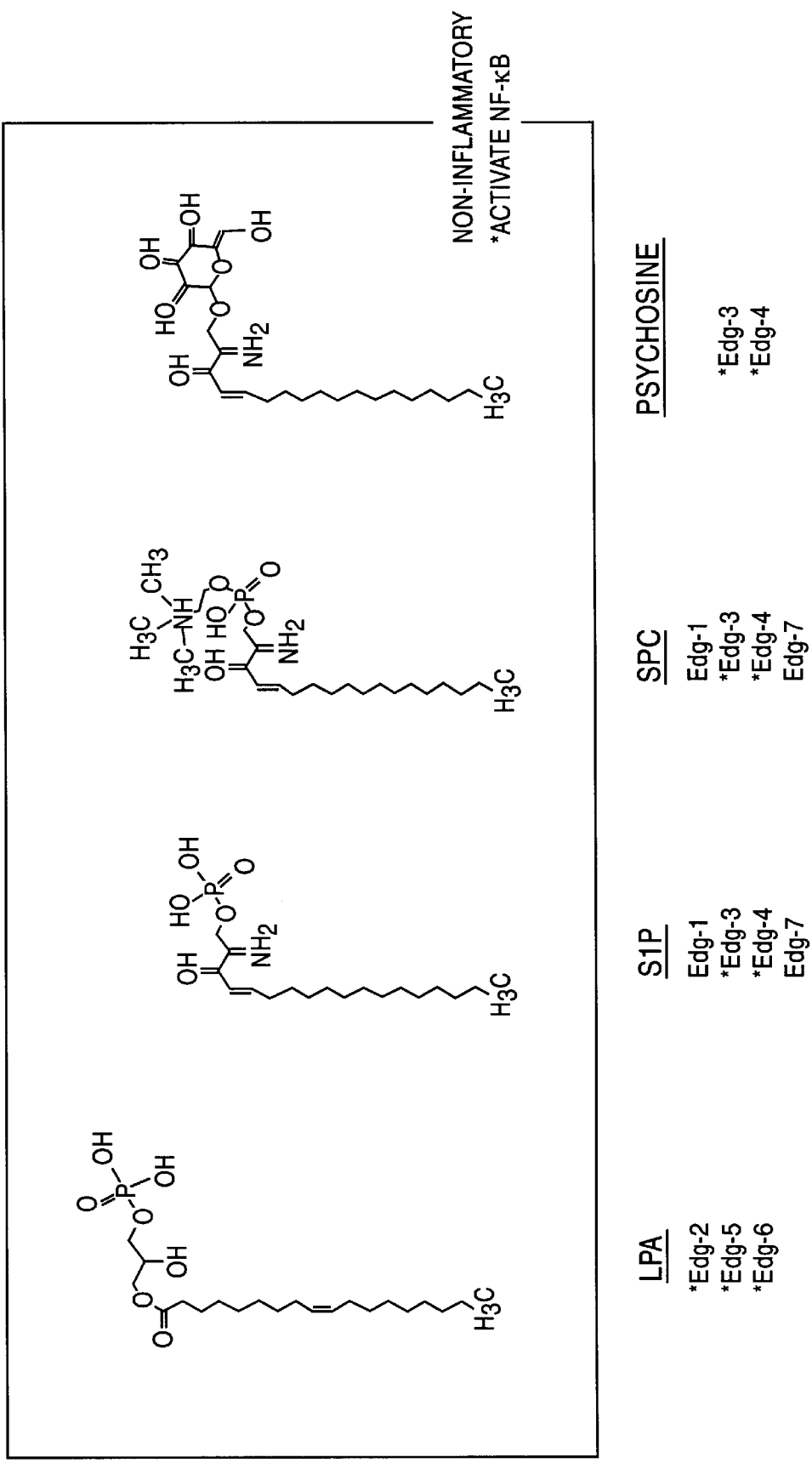
FIG. 25 illustrates edg receptors implicated in the activation of NF-κB.

As exemplified below, 293-EBNA cells were used to transfect EDG receptors. The transfected 293 EBNA cells were then exposed to specific ligands (namely, S1P, SPC and LPA) and NF-κB or IL-8 were measured as an indication of the inflammatory response. Accordingly, using these functional assays, it has now been determined that LPA, S1P and/or SPC bind to EDG-2, EDG-3, EDG-4, EDG-5 and EDG-6 to induce NF-κB and/or IL-8 (See FIG. 25). Since NF-κB and/or IL-8 are products of an inflammatory response pathway and NF-κB is also associated with an anti-apoptotic pathway, EDG-2, EDG-3, EDG-4, EDG-5 and EDG-6 are receptors which are linked to these same pathways. Thereby, by modulating these edg receptors or any edg receptors which activate NF-κB, an inflammatory response or apoptosis-modulating signal can be modulated.

The assays described herein are able to identify inflammatory EDG/LL receptors both in heterologous expression and endogenous expression settings, and to aid in their cloning and characterization. Thus, EDG-2, EDG-3, EDG-4, EDG-5 and EDG-6 were identified herein as inflammatory LL receptors through this approach. Similarly, the determination that edelfosine can provoke a PTX-sensitive IL-8 response in HeLa cells suggests that an edelfosine receptor resides in HeLa cells, which may or may not correspond to an EDG or LL receptor. Isolation of this and other EDG/LL receptors is a straightforward technical exercise, in light of the current disclosure. Given the demonstrated clinical effects of edelfosine, a LL-derived anti-neoplastic agent, such isolated receptors and the attendant functional assays offer great scientific, commercial and medical potential.

The non-receptor-dependent actions of LL might be expected to cause cell injury, possibly activating NF-κB without a requirement for a GPCR receptor. Therefore, a parallel assessment of cytotoxicity with functional response was conducted, along with a clear demonstration of time- and concentration-dependence and ligand specificity, and an assessment of signal transduction mechanism, in order to validate NF-κB activation as a functional assay for the receptors herein. (See Examples below.)

The invention relates in another respect to polynucleotides, in their isolated form, that encode the human EDG-4 receptor. The activity of EDG-4 receptor can be measured using a variety of appropriate functional assays, some of which are described hereinbelow. More particularly, the EDG-4 receptor is capable of binding with LLs, such as S1P and SPC, for signal transduction to induce NF-κB and IL-8.

As used herein and designated by the upper case abbreviation, EDG, refers to the receptor in either naturally occurring or synthetic form and edg refers to the nucleotide sequence of the receptor. In particular, HEDG-4 refers to the human EDG-4 receptor homolog in either naturally occurring or synthetic form and hedg-4 refers to the nucleotide sequence of the human receptor. The HEDG-4 receptor is activated by S1P and SPC and includes the amino acid sequence of FIG. 16A or 16B and biologically active fragments thereof. More particularly, the HEDG-4 receptors preferably have at least 91% sequence identity with each other, and more preferably at least 95% sequence identity with each other.

Definitions

The following definitions are used herein for the purpose of describing particular terms used in the application. Any terms not specifically defined should be given the meaning commonly understood by one of ordinary skill in the art to which the invention pertains.

As used herein "isolated" means separated from nucleotide sequences that encode other proteins. In the context of polynucleotide libraries, for instance, a hedg-4 receptor-encoding nucleotide sequence is considered "isolated" when it has been selected, and hence removed from association with other nucleotide sequences within the library. Such nucleotide sequences may be in the form of RNA, or in the form of DNA including cDNA, genomic DNA and synthetic DNA.

As used herein "purified" refers to sequences that are removed from their natural environment, and are isolated or separated, and are at least 60% free, preferably 75% free, and most preferably 90% free from other components with which they are naturally associated.

An "oligonucleotide" is a stretch of nucleotide residues, which has a sufficient number of bases to be used as an oligomer, amplimer or probe in a polymerase chain reaction (PCR). Oligonucleotides are prepared from genomic or cDNA sequence and are used to amplify, reveal or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring, recombinant, or chemically synthesized single—or double—stranded nucleic acids or be chemically synthesized. They are useful in detecting the presence of identical or similar sequences.

A "portion" or "fragment" of a nucleotide or nucleic acid sequence comprises all or any part of the sequence having fewer nucleotides than about 6 kb, preferably fewer than about 1 kb. A portion or fragment can be used as a probe. Such probes may be labeled with reporter molecules using nick translation, Klenow fill-in reaction, PCR or other methods well known in the art. To optimize reaction conditions and to eliminate false positives, nucleic acid probes may be used in Southern, Northern or in situ hybridizations to determine whether DNA or RNA encoding HEDG-4 is present in a cell type, tissue, or organ.

"Reporter" molecules are those radionuclides, enzymes, fluorescent, chemiluminescent, or chromogenic agents which associate with, establish the presence of, and may allow quantification of a particular nucleotide or amino acid sequence.

"Recombinant nucieotide variants" encoding HEDG-4 may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one (or more than one) of the following HEDG-4 characteristics: cellular location, distribution, ligand-binding affinities, interchain affinities, degradation/tumover rate, signaling, etc.

"Biologically Active or Active" refers to those forms, fragments, or domains of any HEDG-4 polypeptide which retain at least some of the biological and/or antigenic activities of any naturally occurring HEDG-4.

"Naturally occurring HEDG-4" refers to a polypeptide produced by cells which have not been genetically engineered and specifically contemplates various polypeptides arising from polymorphisms found among human populations, as well as those arising from RNA editing, alternative splicing, or post-translational modifications of the polypeptide including but not limited to acetylation, carboxylation, glycosylation, plaosphorylation, lipidation and acylation.

"Derivative" refers to those amino acid sequences and nucleotide sequences which have been chemically modified. Such techniques for polypeptide derivatives include: ubiquitination; labeling (see above); pegylation (derivatization with polyethylene glycol); and chemical insertion or substitution of amino acids such as ornithine which do not normally occur in human proteins. A nucleotide sequence derivative would encode the amino acid which retains its essential biological characteristics of the natural molecule.

"Recombinant polypeptide variant" refers to any polypeptide which differs from naturally occurring HEDG-4 by amino acid insertions, deletions and/or substitutions, created using recombinant DNA techniques. Guidance in determining which amino acid residues may be replaced, added or deleted without abolishing activities of interest may be found by comparing the sequence of HEDG-4 with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically or by systematically making insertions, deletions, or substitutions of nucleotides in the hedge-4 sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is any substance which retards or prevents a biochemical, cellular or physiological reaction or response. Common inhibitors include but are not limited to antisense molecules, antibodies, and antagonists.

"Standard" is a quantitative or qualitative measurement for comparison. It is based on a statistically appropriate number of normal samples and is created to use as a basis of comparison when performing diagnostic assays, running clinical trials, or following patient treatment profiles.

"Stringent conditions" is used herein to mean conditions that allow for hybridization of substantially related nucleic acid sequences. Such hybridization conditions are described by Sambrook et al., Molecular Cloning: A Laboratory Manual, 2nd ed., Cold Spring Harbor Press, 1989. Generally, stringency occurs within a range from about 5° C. below the melting temperature of the probe to about 20° C.–25° C. below the melting temperature. As understood by ordinary skilled persons in the art, the stringency conditions may be altered in order to identify or detect identical or related nucleotide sequences. Factors such as the length and nature (DNA, RNA, base composition) of the sequence, nature of the target (DNA, RNA, base composition, presence in solution or immobilization, etc.) and the concentration of the salts and other components (e.g. the presence or absence of formamide, dextran sulfate and/or polyethylene glycol) are considered and the hybridization solution may be varied to generate conditions of either low or high stringency.

"Animal" as used herein may be defined to include human, domestic (cats dogs, etc.), agricultural (cows, horses, sheep, etc.) or test species (mouse, rat, rabbit, etc.).

"Nucleotide sequences" as used herein are oligonucleotides, polynucleotides, and fragments or portions thereof, and are DNA or RNA of genomic or synthetic origin which may be single or double stranded, and represent the sense or complement or antisense strands.

"Sequence Identity" is known in the art, and is a relationship between two or more polypeptide sequences or two or more polynucleotide sequences, as determined by comparing the sequences, particularly, as determined by the match between strings of such sequences. Sequence identity can be readily calculated by known methods (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two sequences, the term is well known to skilled artisans (see, for example, Sequence Analysis in Molecular Biology; Sequence Analysis Primer; and Carillo, H., and Lipman, D., SIAM J. Applied Math., 48: 1073 (1988)). Methods commonly employed to determine identity between sequences include, but are not limited to those disclosed in Carillo, H., and Lipman, D., SIAM J. Applied Math., 48: 1073 (1988) or, preferably, in Needleman and Wunsch, J. Mol. Biol., 48: 443–445, 1970, wherein the parameters are as set in version 2 of DNASIS (Hitachi Software Engineering Co., San Bruno, Calif.). Computer programs for determining identity are publicly available. Preferred computer program methods to determine identity between two sequences include, but are not limited to, GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990)). The BLASTX program is publicly available from NCBI (blast@ncbi.nlm.nih.gov) and other sources (BLAST Manual, Altschul, S., et al., NCBI NLM NIH Bethesda, Md. 20894; Altschul, S., et al., J. Mol. Bio. 215: 403–410 (1990)). Computational Molecular Biology, Lesk, A. M, ed. Unless specified otherwise in the claims, the percent identity for the purpose of interpreting the claims shall be calculated by the Needleman and Wucnsch algorithm with the parameters set in version 2 of DNASIS.

The EDG receptor family of T7G receptors has been subdivided into 2 subgroups on the basis of sequence similarity and genomic organization (Chun, Contos & Munroe, in press). We have determined that EDG-2, EDG-5 (see U.S. Ser. No. 08/997,803, incorporated herein by reference) and EDG-6 (Genbank Accession AF011466) respond to LPA as an agonist, and share a common intron structure within their coding regions. EDG-1, EDG-3, rat EDG-4/H218 (Accession U10699) and EDG-7 (see co-pending U.S. patent application Ser. No. 60/070,184) have intronless coding regions and respond to S1P and SPC as agonists. The present T7G receptor, HEDG-4, has no intron within the coding region.

One aspect of the present invention is a method for using recombinant HEDG-4 receptors in an assay for screening ligands and potential drug candidates. Although the use of T7G receptors in high-throughput screening is well-known, no such screen has been reported for the HEDG-4 receptor. More specifically, the novel HEDG-4 receptor presented herein can be used to identify and rank the relative potency and efficacy of potential agonists. These compounds may be useful inasmuch as they would be expected to modulate cellular or physiological responses to HEDG-4 agonists, or to initiate or supplement HEDG-4 signaling in cells where the receptor occurs. Equally, once a quantitative and reliable assay is established, it can readily be applied to identify and rank the relative potency and efficacy of receptor antagonists. This application, without limiting other aspects, of the screening methods described herein is specifically contemplated and incorporated within the scope of this invention.

It was determined that S1P and SPC are agonists for HEDG-4.

Other HEDG-4 ligands are likely to be found among the phospholipid class of compounds. Therefore, in one embodiment, phospholipid molecules could be screened to identify ligands. Particularly, it is believed that potential ligands include fatty acid chains of differing length, such as 16, 17, 18, 19, 20, 22 and 24 carbon units, with or without 1, 2, 3 or 4 unsaturated carbon-carbon bonds.

The nucleotide sequences encoding HEDG-4 (or their complement) have numerous applications in techniques known to those skilled in the art of molecular biology. These techniques include use as hybridization probes, use in the construction of oligomers for PCR, use for chromosome and gene mapping, use in the recombinant production of HEDG-4, and use in generation of antisense DNA or RNA, their chemical analogs and the like. Uses of nucleotides encoding HEDG-4 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of hedg-4 encoding nucleotide sequences may be produced. Some of these will only bear minimal homology to the nucleotide sequence of the known and naturally occurring hedg-4. The invention has specifically contemplated each and every possible variation of nucleotide sequence that could be made by selecting combinations based on possible codon choices. These combinations are made in accordance with the standard triplet genetic code as applied to the nucleotide sequence of naturally occurring hedg-4, and all such variations are to be considered as being specifically disclosed.

Although the nucleotide sequences which encode HEDG-4, its derivatives or its variants are preferably capable of hybridizing to the nucleotide sequence of the naturally occurring hedg-4 under stringent conditions, it may be advantageous to produce nucleotide sequences encoding HEDG-4 or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding HEDG-4 and/or its derivatives without altering the encoded amino acid sequence include the production of RNA transcripts having more desirable properties, such as a greater half-life, than transcripts produced from the naturally occurring sequence.

Human genes often show considerable actual polymorphism; that is, variation in nucleotide sequence among a fraction of the entire human population. In many cases this polymorphism can result in one or more amino acid substitutions. While some of these substitutions show no demonstrable change in function of the protein, others may produce varying degrees of functional effects. In fact, many natural or artificially produced mutations can lead to expressible HEDG proteins. Each of these variants, whether naturally or artificially produced, is considered to be equivalent and specifically incorporated into the present invention.

Nucleotide sequences encoding HEDG-4 may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel F M et al (1989) Current Protocols in Molecular Biology, John Wiley & Sons, New York City). Useful nucleotide sequences for joining to hedg-4 include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease senstive sites, and selectable markers for one or more host cell systems.

Another aspect of the subject invention is to provide for hedg-4 specific hybridization probes capable of hybridizing with naturally occurring nucleotide sequences encoding HEDG-4. Such probes may also be used for the detection of similar T7G encoding sequences and should preferably contain at least 91% nucleotide identity to hedg-4 sequence and more preferably at least 95% identity. The hybridization probes of the subject invention may be derived from the nucleotide sequence presented in the figures for hedge or from genomic sequences including promoter, enhancers, introns or 3'-untranslated regions of the native gene. Hybridization probes may be labeled by a variety of reporter molecules using techniques well known in the art. Preferably, the hybridization probes incorporate at least 15 nucleotides, and preferably at least 25 nucleotides, of the hedg-4 receptor.

It will be recognized that many deletional or mutational analogs of nucleic acid sequences for HEDG-4 will be effective hybridization probes for HEDG-4 nucleic acid. Accordingly, the invention relates to nucleic acid sequences that hybridize with such HEDG-4 encoding nucleic acid sequences under stringent conditions.

Stringent conditions will generally allow hybridization of sequence with at least about 70% sequence identity, more preferably at least about 80–85% sequence identity, even more preferably at least about 90% sequence identity, and most preferably with at least about 95% sequence identity Hybridization conditions and probes can be adjusted in well-characterized ways to achieve selective hybridization of human-derived probes. Nucleic acid molecules that will hybridize to HEDG-4 encoding nucleic acid under stringent conditions can be identified functionally, using methods outlined above, or by using for example the hybridization rules reviewed in Sambrook et al., Molecular Cloning: A Laboratory Manual, 2nd ed., Cold Spring Harbor Press, 1989. Without limitation, examples of the uses for hybridization probes include: histochemical uses such as identifying tissues that express HEDG-4; measuring mRNA levels, for instance to identify a sample's tissue type or to identify cells that express abnormal levels of HEDG-4; and detecting polymorphisms in the HEDG-4. RNA hybridization procedures are described in Maniatis et al. Molecular Cloning, a Laboratory Manual (Cold Spring Harbor Press, 1989). PCR as described U.S. Pat. Nos. 4,683,195; 4,800,195; and 4,965,188 provides additional uses for oligonucleotides based upon the nucleotide sequence which encodes the EDG-4 sequences of the invention. Such probes used in PCR may be of recombinant origin, chemically synthesized, or a mixture of both. Oligomers may comprise discrete nucleotide sequences employed under optimized conditions for identification of hedg-4 in specific tissues or diagnostic use. The same two oligomers, a nested set of oligomers, or even a degenerate pool of oligomers may be employed under less stringent conditions for identification of closely related DNA's or RNA's. Rules for designing PCR primers are now established, as reviewed by PCR Protocols, Cold Spring Harbor Press, 1991. Degenerate primers, i.e., preparations of primers that are heterogeneous at given sequence locations, can be designed to amplify nucleic acid sequences that are highly homologous to, but not identical to hedg-4. Strategies are now available that allow for only one of the primers to be required to specifically hybridize with a known sequence. See, Froman et al., Proc. Natl. Acad. Sci. USA 85: 8998, 1988 and Loh et al., Science 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified. PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, PCR Protocols, Cold Spring Harbor Press, 1991.

Other means of producing specific hybridization probes for hedg-4 include the cloning of nucleic acid sequences encoding HEDG-4 or HEDG-4 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the man) available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

The nucleotide sequence for hedg-4 can be used in an assay to detect inflammation or disease associated with abnormal levels of HEDG-4 expression. The cDNA can be labeled by methods known in the art, added to a fluid, cell or tissue sample from a patient, and incubated under hybridizing conditions. After an incubation period, the sample is washed with a compatible fluid which optionally contains a reporter molecule. After the compatible fluid is rinsed off, the reporter molecule is quantitated and compared with a standard as previously defined.

A diagnostic test for aberrant expression of HEDG-4 can accelerate diagnosis and proper treatment of abnormal conditions of for example, the heart, kidney, lung and testis. Specific examples of conditions in which aberrant expression of HEDG-4 may play a role include adult respiratory distress, asthma, rheumatoid arthritis, cardiac ischemia, acute pancreatitis, septic shock, psoriasis, acute cyclosporine nephrotoxicity and early diabetic glomerulopathy, as well as lung damage following exposure to cigarette smoke, asbestos or silica.

Nucleotide sequences encoding hedg-4 may be used to produce a purified oligo—or polypeptide using well known methods of recombinant DNA technology. Goeddel (1990, Gene Expression Technology, Methods and Enzymology, Vol. 185, Academic Press, San Diego Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding HEDG-4 may be cultured under conditions suitable for the expression of T7Gs, their extracellular, transmembrane or intracellular domains and recovery of such peptides from cell culture. HEDG-4 (or any of its domains) produced by a recombinant cell may be secreted, expressed on cellular membranes or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from hedge or a desired portion of the polypeptide to a nucleic acid sequence encoding a polypeptide domain which will facilitate protein purification (Kroll D J et al (1993) DNA Cell Biol. 12:441–53).

In addition to recombinant production, fragments of HEDG-4 may be produced by direct peptide synthesis using solid-phase techniques (e.g. Stewart at al (1969) Solid-Phase Peptide Synthesis, WH Freeman Co., San Francisco QA; Merrifield J (1963) J Am Chem. Soc. 85:2149–2154). Automated synthesis may be achieved, for example, using Applied Biosystems 431A Peptide Synthesizer (Foster City, Calif.) in accordance with the instructions provided by the manufacturer. Additionally, a particular portion of HEDG-4 may be mutated during direct synthesis and combined with other parts of the peptide using chemical methods.

HEDG-4 for antibody induction does not require biological activity: however, the protein must be antigenic. Peptides used to induce specific antibodies may have an aa (amino acid) sequence consisting of at least five amino acids (aa), preferably at least 10 aa. They should mimic a portion of the aa sequence of the protein and may contain the entire aa sequence of a small naturally occurring molecule such as HEDG-4. An antigenic portion of HEDG-4 may be fused to another protein such as keyhole limpet hemocyanin, and the chimeric molecule used for antibody production.

Antibodies specific for HEDG-4 may be produced by inoculation of an appropriate animal with the polypeptide or an antigenic fragment. An antibody is specific for HEDG-4 if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (e.g. Orlandi R et al (1989) PNAS 86:3833–3837, or Huse WD et al (1989) Science 256:1275–1281) or the in vitro stimulation of lymphocyte populations. Current technology (Winter G and Mistein C (1991) Nature 349:293–299) provides for a number of highly specific binding reagents based on the principles of antibody formation. These techniques may be adapted to produce molecules which specifically bind HEDG-4s.

An additional embodiment of the subject invention is the use of HEDG-4 specific antibodies, inhibitors, ligands or their analogs as bioactive agents to treat inflammation or disease including, but not limited to viral, bacterial or fungal infections; allergic responses; mechanical injury associated with trauma; hereditary diseases; lymphoma or carcinoma; or other conditions which activate the genes of kidney, lung, heart, lymphoid or tissues of the nervous system.

Bioactive compositions comprising agonists, antagonists, receptors or inhibitors of HEDG-4 may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving aberrant expression of the EDG-4 gene.

All publications and patent applications mentioned herein are incorporated by reference for the purpose of describing the methodologies, cell lines and vectors, among other things. However, nothing herein is to be construed as an admission that the invention is not entitled to antedate such disclosure, for example, by virtue of prior invention.

The examples below are provided to illustrate the subject invention. These examples are provided by way of illustration and are not included for the purpose of limiting the invention.

EXAMPLE 1

IL-8 Response to S1P in HeLa Cells is Concentration and Time Dependent

Figure 1A:
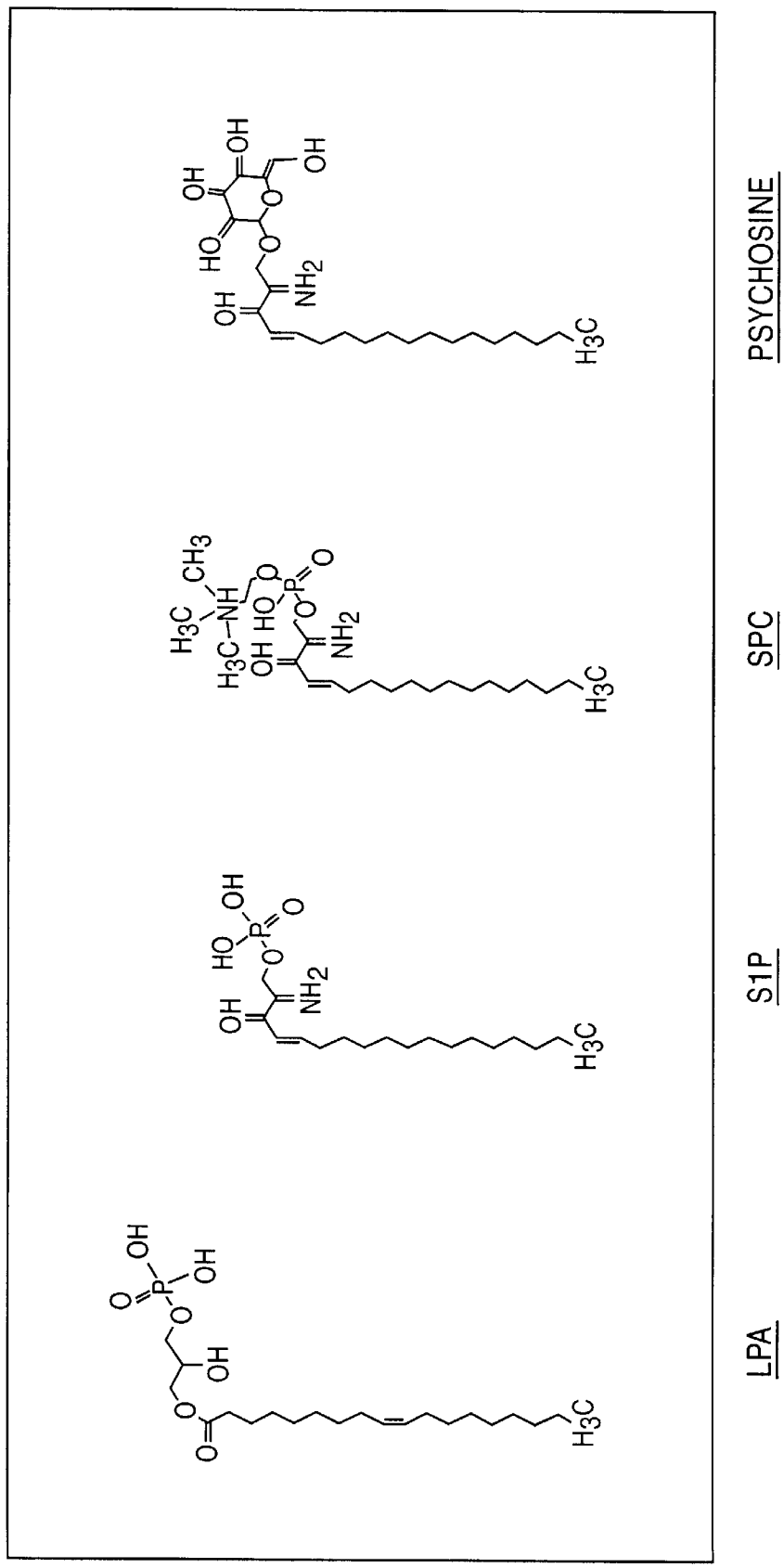
FIG. 1A illustrates the chemical structure of LPA, S1P, SPC and pyschosine.
Figure 1B:
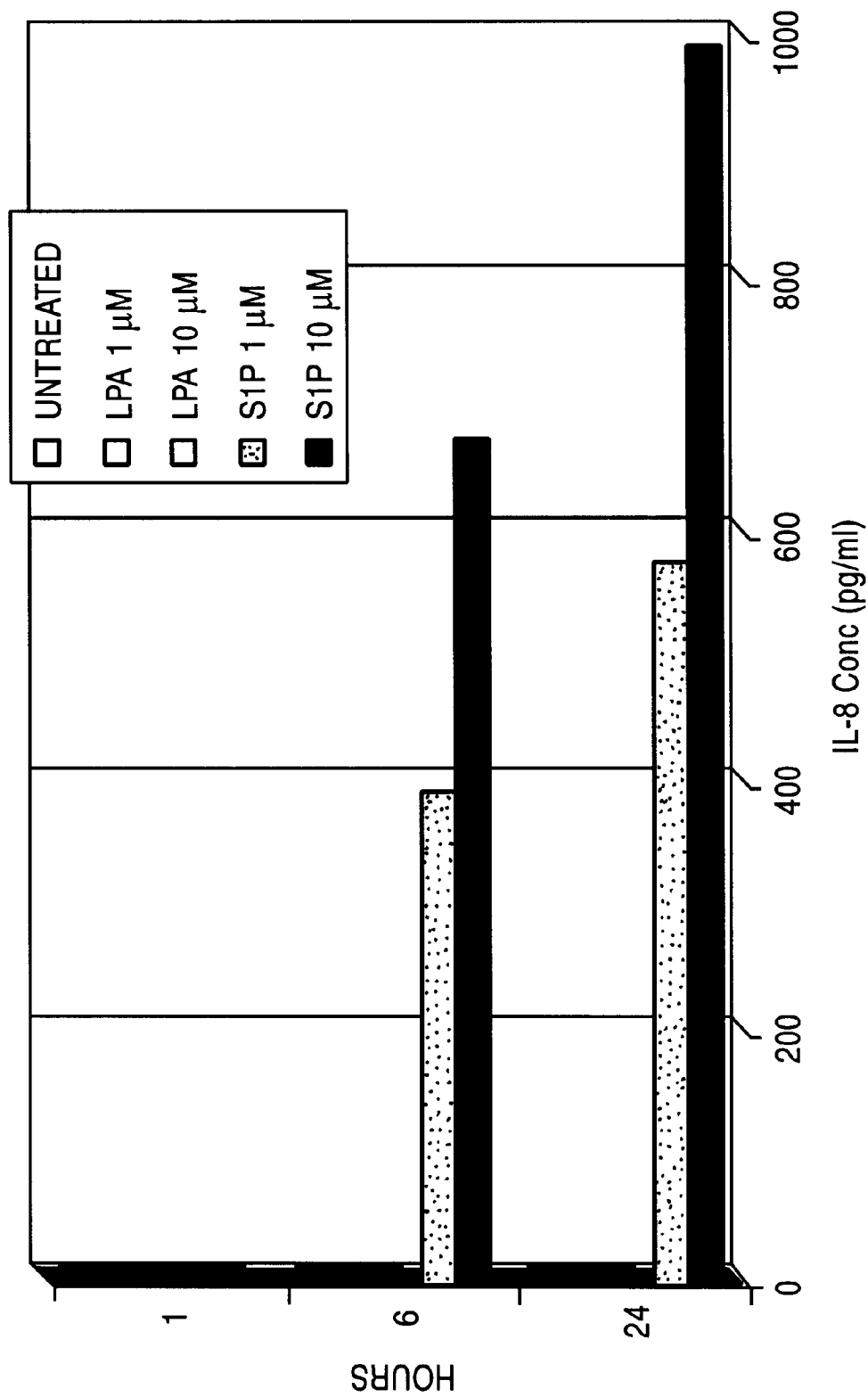
FIG. 1B illustrates the time- and concentration-dependent IL-8 response to S1P and LPA in HeLa cells.

A preliminary survey of cell lines for IL-8 and IL-6 response to S1P identified HeLa cells as a potential responder (FIG. 1B), while HL-60 cells were unresponsive, consistent with the reported lack of S1P receptors in these cells (FIG. 5). IL-8 and IL-6 are potently induced by a variety of proinflammatory agents, including TNF-α, phorbol ester (TPA) and ultraviolet radiation. Induction by these agents is dependent on transcriptional upregulation by NF-κB, although NF-IL6 and AP-1 also play roles in certain experimental models. Because commercially available IL-8 ELISA kits offer a robust and simple measurement with moderately high throughput, we chose to focus on the IL-8 response in the first instance. Later work included the NF-κB reporter gene. However, since the novelty and utility of this invention broadly encompasses inflammatory signaling by edg/LL receptors, we include other receptor-dependent proinflammatory reporters, including, but not limited to NF-κB, NF-IL6 and AP-1 activation are within the scope of the present invention.

Procedure #1 For HeLa Cells
A. Seeding Cells and Cell Plating Density
  Cells: HeLa (adenocarcinoma, human)
  Media: DMEM/F12+10%FBS adherent
    1) Cells were seeded at $0.2 \times 10^6$ cells/well in 6-well plates.
    2) Confluency of cells after 24–32 hrs was between 60–70%.
B. Overnight Serum-Starvation
    1) Media was aspirated (no PBS wash).
    2) 1.5 ml 0.5% FBS media was added to each well.
C. Treatments and Collection
    1) Made up all required solutions in 0.5% FBS media (control). Handling of LL for use in NF-κB experiments requires that sonication, commonly used to resuspend LPA, not be done; NF-κB may be activated by lipid peroxides created through vigorous frothing.
Solutions:
    TPA 100 ng/ml, Stock 0.1 mg/ml in DMSO Sigma, Cat. P-1585, Dilution 1:1000
    LPA 10 μM, Stock 10 mM in 0.2% Albumin Bovine, Sigma, Cat. A-0281in PBS; Dilution 1:1000
    LPA 1 μM, Dilute 10 μM 1:10
    S1P 10 μM, Stock 10 mM in methanol, Sigma, Cat. S-9666, Dilution 1:1000
    S1P 1 μM, Dilute 10 μM 1:10
    Note: All stock solutions are dissolved by pipetting and stored at −20° C.
  2) Media was aspirated.
  3) 1.5 ml appropriate treatments were added to each well.
  4) All plates were placed at 37° C./5% $CO_2$ for either 1, 6, or 24 hours.
  5) After the specified time cell supernatants were collected into 1.5 ml eppendorf tubes, spun down at 14000 rpm for 5 minutes and stored at −20° C. for later ELISA determination.
D. Detection of Interleukin-8 (IL-8) using an IL-8 ELISA (Enzyme-Linked InimunoSorbent Assay).
  1) The Quantikine Human IL-8 ImmunoAssay Kit was obtained from R&D Systems (Cat. D8050).
  2) The kit and all samples were allowed to equilibrate to room temperature prior to use.
  3) All reagents were provided in the kit and prepared according to the instructions provided.
  4) The assay procedure was followed as recommended in the kit for cell culture supernatant samples.
  5) ELISA was performed on 50 μl samples of culture supernatant and duplicate samples were measured for each well. Each treatment was performed on triplicate wells.
  6) Plates were read on UVmax kinetic microplate reader (Molecular Devices), set to 450 nm and correction set to 575 nm, using Wsoftmax software version 2.34.
    Results: This experiment showed a time- and concentration-dependent IL-8 response to S1P, but not LPA, in HeLa cells (see FIG. 1B).

EXAMPLE 2

S1P and SPC Both Induce a Concentration-dependent, PTX-sensitive IL-8 Response in HeLa Cells S1P and SPC both show PTX-sensitive functional responses in certain cell types. However, in some cell types S1P shows 10-fold or higher potency than SPC, while in other cell types S1P and SPC are roughly equipotent. If the IL-8 response to S1P and SPC is receptor-mediated, we might expect to see PTX-sensitivity with both ligands and possibly, an equal or reduced potency with SPC.

Procedure #2 For HeLa Cells
A. Seeding Cells and Cell Plating Density
  Cells: HeLa (adenocarcinoma, human), Media: DMEM/F12+10%FBS adherent cells
    1) Cells were seeded at $2.5 \times 10^4$ cells/well in 24-well plates.
    2) Confluency of cells after 24–32 hrs was between 60–70%.
B. Overnight Serum-Starvation and PTX Pre-Treatment
    1) Media was aspirated (no PBS wash).
    2) 0.5 ml 0.5% FBS media was added to all wells not requiring PTX pre-treatment.
    3) For wells requiring PTX; 0.5 ml 0.5% FBS media containing 50 ng/ml PTX (1 volume PTX (RBI Cat. P140): 1 volume DTT, incubate 37° C. for 30 minutes then dilute to 50 ng/ml) was added.

C. Treatments and Collection
1) Made up all required solutions in 0.5% FBS media (control).
Solutions:
S1P 3, 10, 30, 100, 300, 1000, 3000, 10000 nM
SPC 10 µM Stock 10 mM in methanol, Sigma, Cat. S4257, Dilution 1:1000
SPC 1, 3, 10, 30, 100, 300, 1000, and 3000 nM
2) Media was aspirated.
3) 0.5 ml appropriate treatments were added.
4) All plates were placed at 37° C./5% $CO_2$ for 6 hours.
5) After the specified time cell supernatants were collected into 1.5 ml eppendorf tubes, spun down at 14000 rpm for 5 minutes and stored at −20° C. for later ELISA determination.

D. Refer to Procedure #1 For HeLa Cells (D).

Results: The experiment demonstrated unequivocally that both S1P and SPC can induce IL-8 in HeLa cells in a concentration-dependent manner (FIG. 2A), and that these responses are PTX-sensitive, as expected of a $G_i$-coupled receptor (see FIG. 2B).

EXAMPLE 3

Effect of PTX on IL-8 Response to S1P and TNF-α in HeLa Cells

Effects of PTX toxin reflect a requirement for the $G_{i/o}$ family of heterotrimeric G proteins, which play critical roles in the multiple actions of GPCRs. It is possible, however, that the PTX inhibition of S1P-induced IL-8 response reflects an indirect effect on downstream signal transduction events, rather than an effect on the G proteins directly coupled to a GPCR for S1P. If a general block of IL-8 production is produced by PTX in HeLa cells, then IL-8 production by TNF-α should also be inhibited. TNF-α induces IL-8 through its own receptor, which is not a GPCR and does not require $G_{i/o}$ for signaling. On the other hand, if the IL-8 response to TNF-α is unaffected, then the blockade by PTX is specific to S1P but not TNF-α signaling pathways.

Procedure #3 For HeLa Cells

Follow Procedure #2 For HeLa Cells with the following exceptions:
1) Solutions required in section C are as follows:
S1P 5 µM
TNF-α 50 ng/ml Stock 10 µg/ml in 0.1% Albumin Bovine R&D, Cat. 210-TA
(Albumin: Sigma; Cat. A-028 1) in PBS
Dilute 1:200

Results: The results clearly showed that while PTX potently blocked the IL-8 response to S1P, the response to TNF-α was not significantly affected (see FIG. 3). Thus, $G_{i/o}$ pathways are required for S1P signaling that leads to the IL-8 response in HeLa cells.

EXAMPLE 4A

IL-8 Response to S1P in HeLa Cells is Ligand-selective and not a General LL Response S1P shares a detergent-like structure with many other LL. (See FIG. 1A) Thus, non-specific activation of NF-κB by cell injury or membrane actions of S1P should be produced by many other LL as well. Additionally, any general non-selective LL receptor expressed in HeLa should be activated interchangeably by several different LL. Alternatively, ligand-selective activation of NF-κB argues for a receptor-mediated mechanism amenable to future drug discovery.

Procedure #4 For HeLa Cells

Follow Procedure #2 For HeLa Cells with the following exceptions:
1) No PTX Pre-Treatment is required in section B.
2) Solutions required in section C are as follows:
LPC Stock 10 mM in methanol Sigma, Cat. L-1381
LPE Stock 10 mM in chloroform Sigma, Cat. L-4754
LPG Stock 10 mM in methanol Sigma, Cat. L-4525
LPI Stock 10 mM in 1% Albumin Bovine in PBS Sigma, Cat. L-7635
LPS Stock 10 mM in 0.2% Albumin Bovine in PBS Sigma, Cat. L-5772
Lyso-PAF Stock 10 mM in 1% Albumin Bovine in PBS Sigma, Cat. L-7890
Lysosulfatide Stock 10 mM in DMSO Sigma, Cat. L-3640
Sphingosine Stock 10 mM in methanol Sigma, Cat. S-6136
Sphingomyelin (SM) Stock 10 mM in methanol Sigma, Cat. S-7004
Concentrations for LPC, LPE, LPG, LPS, sphingosine and SM used were 10, 50, 100, 1000, and 5000 nM. Concentrations for LPI, lyso-PAF and lysosulfatide used were 0.3 and 3 µM.

Results: Only S1P and SPC significantly induced IL-8 production, strongly suggesting that a ligand-selective receptor mediates the PTX-sensitive IL-8 response pathway. While sphingosine is shown together with S1P as examples of the ligand-selectivity of the IL-8 response, a similar lack of response was observed in HeLa cells with all other compounds listed above, but not shown on the graph (see FIG. 4A).

EXAMPLE 4B

IL-8 Response to S1P, LPA and Other Lysolipids in Primary Cultured Human Umbilical Vein Endothelial Cells (HUVEC)

While HeLa cells form the basis of an experimentally homogeneous assay system, these cells have been carried continuously in culture for many years. Moreover, they are a transformed (i.e. neoplastic) cell line, and as such, carry many chromosomal and genetic abnormalities. As will be readily apparent to one skilled in cell and molecular biology, findings in HeLa cells should be confirmed in a non-transformed cell line, preferably primary cultured human cells. We chose HUVEC, a commonly available human primary cell culture. Since these cells are derived from the endothelium lining the umbilical vein, they share many characteristics and response pathways with endothelial cells found elsewhere in the human body. More particularly, HUVEC cells have been used for the study of NF-κB activation by GPCRs (Ishizuka T, et al Stimulation with thromboxane A2 (TXA2) receptor agonist enhances ICAM-1, VCAM-1 or ELAM-1 expression by human vascular endothelial cells. Clin Exp Immunol. 1998 June;112(3):464–470; Munoz C, et al Pyrrolidine dithiocarbamate inhibits the production of interleukin-6, interleukin-8, and granulocyte-macrophage colony-stimulating factor by human endothelial in response to inflammatory mediators: modulation of NF-κB and AP-1 transcription factors activity. Blood. 1996 November 1;88(9):3482–3490.). Among the documented consequences of NF-κB activation in this cell type are the production of cytokines such as IL-8, IL-6 and GM-CSF. In addition, cell adhesion molecules such as VCAM-1, ELAM-1 and ICAM-1 are upregulated, which play distinct roles in the attaclunent and extravasation of peripheral blood leukocytes at sites of injury or inflammation. The following experiment was conducted to look for IL-8 production in cultured HUVEC exposed to S1P, LPA or other lysolipids.

Plating, Pretreatment and Treatment of HUVEC

Procedures were followed as detailed above in "Procedure #1 for HeLa Cells" with the following exceptions:
Cells: HUVEC (Clonetics, Cat. CC-2519) were passaged according to supplier's instructions and used at passage 3. Cells were plated at 20,000 cells/well into 24-well plates. The next day, cells were serum-starved overnight in EBM medium (Clonetics) with 0.5% FBS, and then treated in EBM without FBS for 6 hr with the following lysolipids:
1) Control (no lysolipids)
2) Anandarnide
3) Edelfosine
4) LPA
5) S1P
6) SPC
7) Psychosine Supematants were collected and IL-8 levels were determined using ELISA as described previously.

Figure 4B:
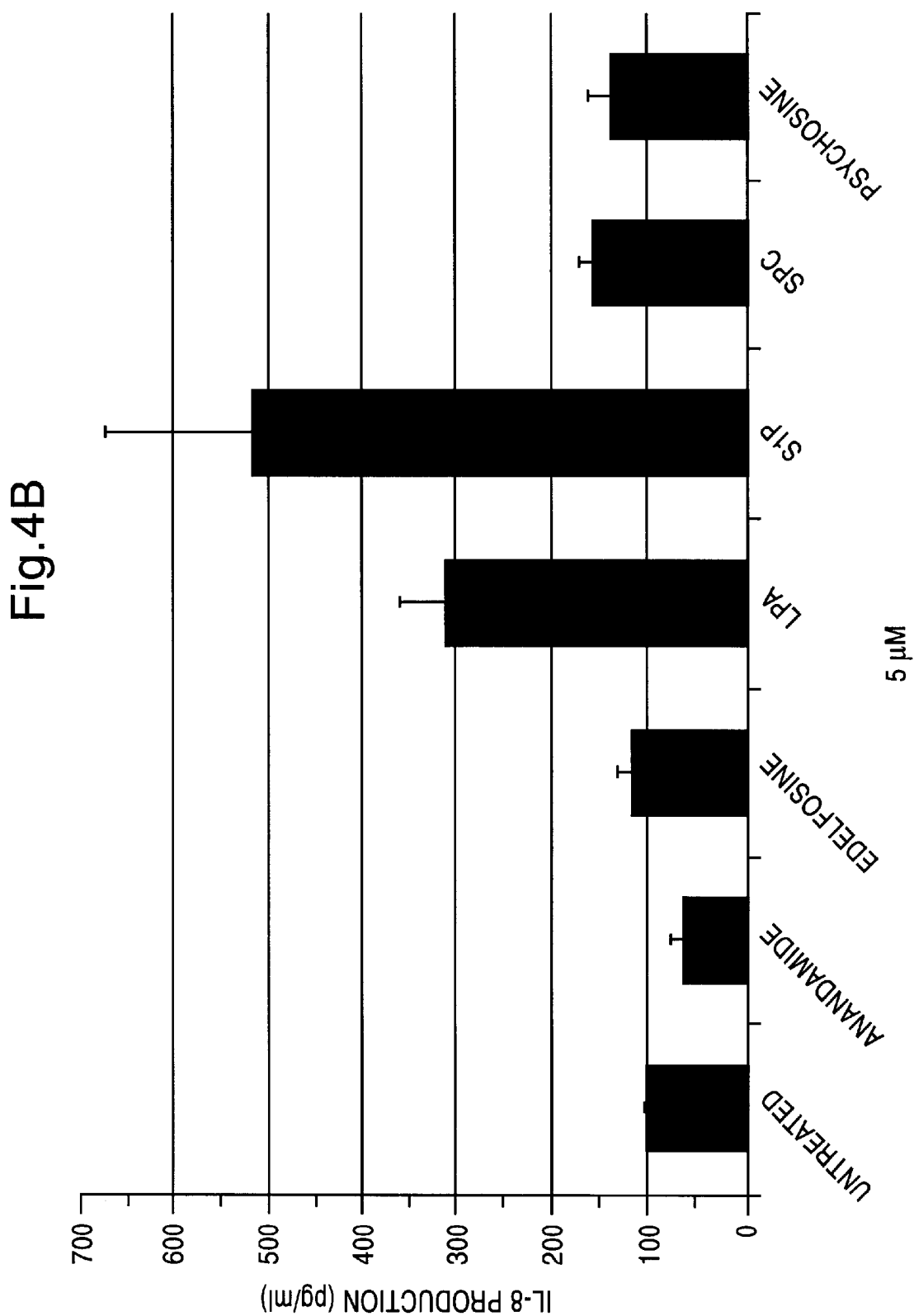
FIG. 4B illustrates the IL-8 response to lysolipids in primary cultured Human Umbilical Vein Endothelial Cells (HUVEC).

Results: After 6 hr of treatment with 5 $\mu$M S1P, IL-8 levels were increased approximately 5-fold over untreated controls, as shown in FIG. 4B. LPA induced a 3-fold IL-8 increase at this concentration. Marginal increases were seen after SPC and psychosine treatment, while no response was seen with anandamide or edelfosine. Therefore, IL-8 production was responsive to S1P in primary cultured human endothelial cells, similar to the results seen in HeLa cells. In addition, LPA induced IL-8 production in HUVEC, but not HeLa cells, suggesting that inflammatory receptors for LPA may be expressed in the former cell type. As shown below in FIG. 23, three cloned edg receptors respond to LPA as an agonist, and all three appear to transduce NF-κB activation in an agonist-dependent manner.

EXAMPLE 5

Lack of IL-8 Response to S1P in HL-60 Cells

HL-60 cells have been reported not to possess S1P receptors. One contradictory report has been published, but in that work, 10 $\mu$M concentration of S1P was used, 10–1000 times higher than other studies of S1P receptors. Nonetheless, HL-60 cells were examined for IL-8 response to S1P. As a control, IL-8 release from HL-60 cells was tested after treatment with TNF-α, which acts through a non-GPCR cell-surface receptor.

Procedure for HL-60 Cells:
A. Seeding Cells and Cell Plating Density
Cells: HL-60 (promyelocytic, human) suspension cells
Media: RPMI 1640 medium with 2 mM L-glutamine adjusted to contain 4.5 g/L glucose, 10 mM HEPES, and 1.0 mM sodium pyruvate+10% FBS
1) Cells were plated at a density of 0.25×10$^6$ cells/ml.
2) Density of cells after 48–56 hrs was approximately 1×10$^6$ cells/ml.

B. Overnight Pre-Treatments
1) Cells were spun down at 1000 rpm for 5 minutes.
2) Cell pellcts were resuspended in 0.5% FBS media at a density of approximately 1×10$^6$ cells/ml.
C. Treatments and Collection
1) Made up all required solutions in 0.5% FBS media (control).
TNF-α 10 ng/ml
LPA 10 and 1 $\mu$M
S1P 10 and 1 $\mu$M
2) 1.4 ml appropriate treatments were added to each well of a 6-well plate.
3) Cells were spun down at 1000 rpm for 5 minutes.
4) Cells were resuspended in 0.5% media to give a density of approximately 1×10$^6$ cells/100 $\mu$l.
5) 100 $\mu$l cell suspension was added to each well.
6) All plates were placed at 37° C./5% CO$_2$ for either 1, 6, or 24 hours.
7) After the specified time cell supematants were collected into 1.5 ml eppendorf tubes, spun down at 14000 rpm for 5 minutes and stored at −20° C.
D. Refer to Procedure #1 For HeLa Cells (D).

Results: Although HL-60 cells were capable of responding at 6 or 24 hr to TNF-α by releasing IL-8, no such release occurred in response to S1P or LPA at concentrations up to 3 $\mu$M (see FIG. 5). This concentration is 100 times higher than the lowest concentration that reliably induces IL-8 production in HeLa cells. Thus, the IL-8 response to S1P is expressed in some, but not all cell types.

EXAMPLE 6

HeLa Cell IL-8 Response to S1P is not Due to Cytotoxicity

For LL, demonstration of signaling at concentrations well below those that cause lo cytotoxicity is important. For this purpose, an experiment was conducted to measure cytotoxicity in parallel with IL-8 response. A stringent measure of cytotoxicity was applied, in that IL-8 responses were measured after 6 hr of S1P treatment, whereupon the medium was replaced with normal medium and viable cells were counted at 24 hr. Therefore, IL-8 production had to be robust to be observed at 6 hr, while even slight or delayed toxicity would be seen as a loss of viability at 24 hr.

Procedure #5 For HeLa Cells

Follow Procedure #2 For HeLa Cells with the following exceptions:
1) No PTX Pre-Treatment is required in section B.
2) Solutions required in section C are as follows:
S1P 0.3, 1, 3, 10, and 30 $\mu$M.
3) Cytotoxicity determination was added to section C; after step 5, 0.5 ml of 0.5% FBS/media was added to all the wells and placed at 37° C./5%CO$_2$ overnight.
4) Number of viable cells were counted after 24 hours of the initial treatments.

Figure 6:
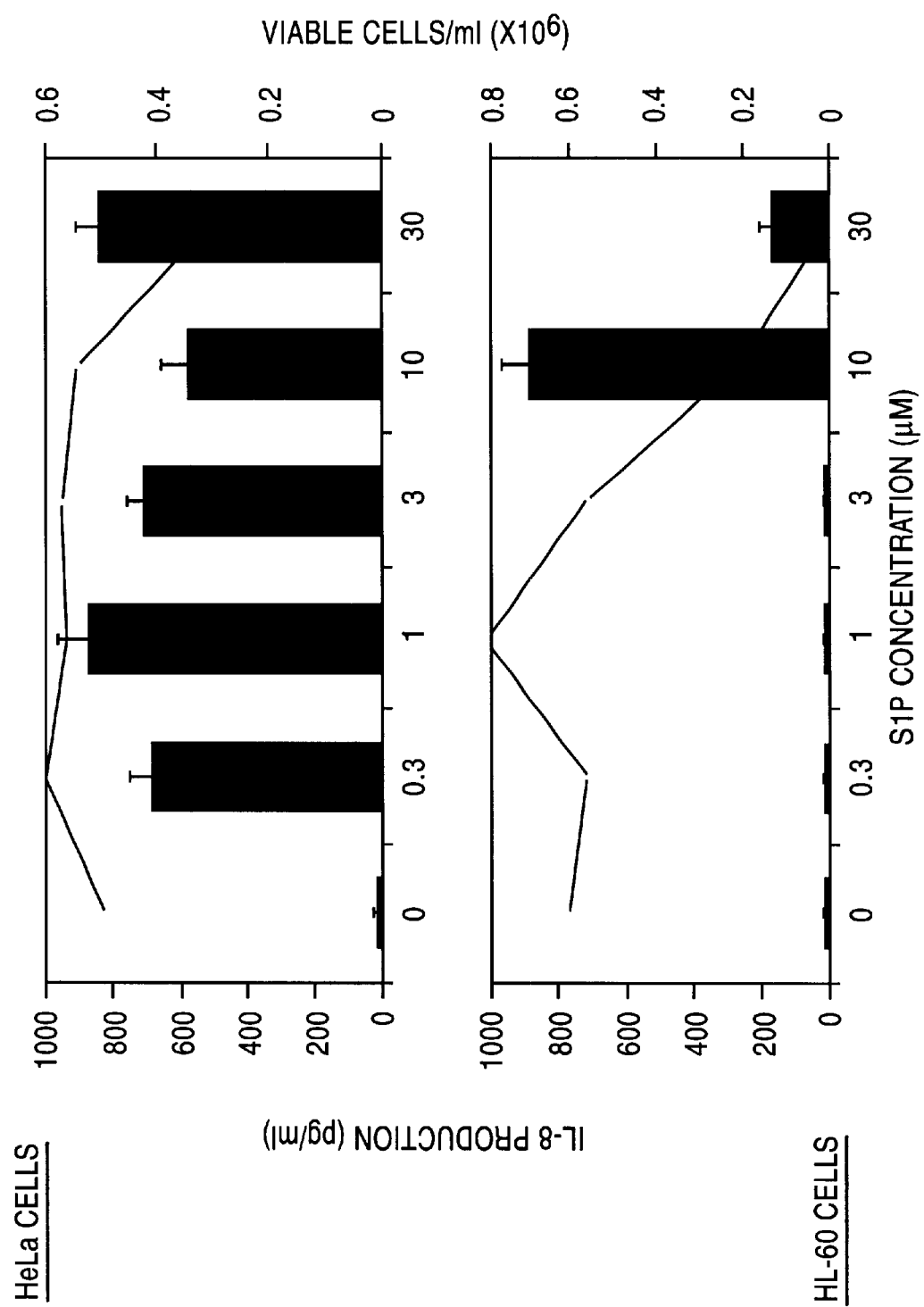
FIG. 6 illustrates the concentration-dependent IL-8 response to S1P in HeLa and HL-60 cells, as well as the cell viability at each S1P concentration level.

Results: No loss of HeLa viability was seen 24 hr after treatment with S1P concentrations up to 10 $\mu$M. In contrast, IL-8 production was seen even at 0.3 $\mu$M S1P, where levels were already near plateau values (see FIG. 6). In repeated experiments, the lowest S1P concentration that reliably induces IL-8 is about 30 nM, more than 100-fold below the cytotoxic threshold. HL-60 cells, on the other hand, show toxicity beginning at 10 $\mu$M S1P, but fail to produce IL-8 below the cytotoxic threshold. Thus, the IL-8 response to S1P does not reflect a non-specific cellular response to injury or impending death.

EXAMPLE 7

Effect of Suramin on IL-8 Response to S1P in HeLa Cells

Suramin is a non-selective inhibitor of extracellular ligand-receptor interactions with no known intracellular targets. This agent is used to provide evidence of an extracellular site of action both for LPA and S1P. The IL-8 response was tested to determine if it could be blocked at this extracellular site.

Procedure #6 For HeLa Cells

Follow Procedure #2 For HeLa Cells with the following exceptions:
1) No PTX Pre-Treatment is required in section B.
2) Solutions required in section C are as follows:
3) Suramin 1 mg/ml, Stock 100 mg/ml in distilled water, Calbiochem, Cat. 574625, Dilute 1:100
   S1P 1 $\mu$M
   S1P 1 $\mu$M+suramin 1 mg/ml
4) A 30 minute pre-treatment at 37° C./5%$CO_2$ of 0.5 ml of 1 mg/ml suramin was done to all wells except control and S1P 1 $\mu$M before step 3 of section C.

Figure 7:
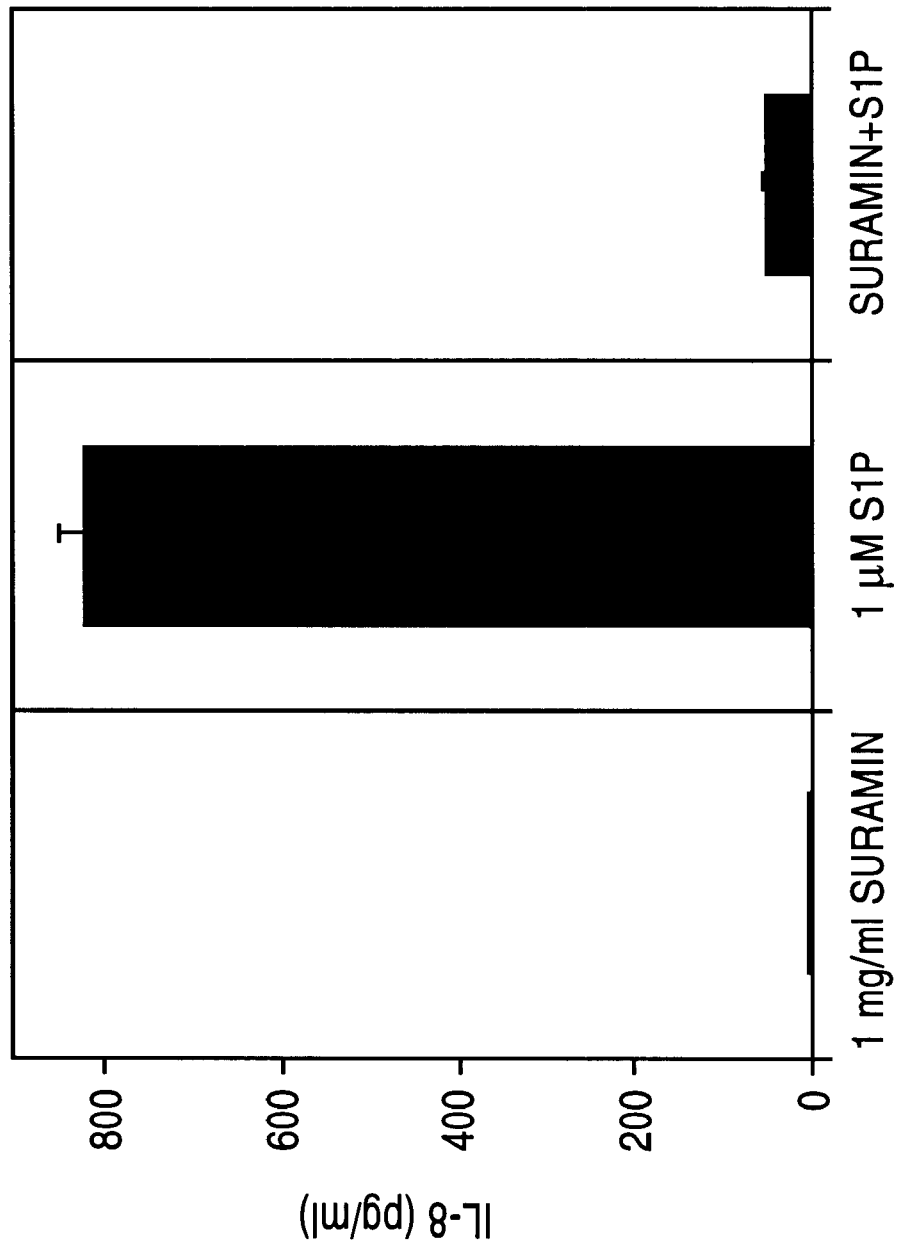
FIG. 7 illustrates the effect of surarmin on the IL-8 response to S1P in HeLa cells.

Results: Suramin was extremely effective in blunting the IL-8 response to S1P (see FIG. 7). Therefore, the most likely site of S1P action is at an extracellular receptor.

EXAMPLE 8

Effect of NDGA and NAC on IL-8 Response to S1P in HeLa Cells

NF-$\kappa$B and IL-8 production can be induced by many different inflammatory agents. Nearly all these diverse agents initiate signal transduction pathways that ultimately converge on destruction of the intracellular repressor I$\kappa$B, which holds NF-$\kappa$B function in check in resting cells. However, the upstream pathways used to target I$\kappa$B differ depending on the nature of the inducer. While inflammatory cytokines and TPA use intracellular reactive oxygen species (ROS) as a second messenger, TNF-$\alpha$ and IL-1 usually do not. The ROS pathway and subsequent NF-$\kappa$B activation can be inhibited by NDGA, NAC and certain other antioxidants. Therefore, the sensitivity of the IL-8 response induced by S1P to these antioxidants was evaluated.

Procedure #7 For HeLa Cells

Follow Procedure #2 For HeLa Cells with the following exceptions:
1) No PTX Pre-Treatment is required in section B.
2) Solutions required in section C are as follows:
3) NDGA 40 $\mu$M Stock 10 mM in ethanol, Sigma, Cat. N-5023, Dilute 1:250
   NAC 30 mM Stock 0.3 M in PBS, pH to 7.4, Calbiochem, Cat.106425, Dilute 1:10
   S1P 1 $\mu$m
   S1P 1 $\mu$M+NDGA 40 $\mu$M
   S1P 1 $\mu$M+NDGA 10 $\mu$M
   S1P 1 $\mu$M+NAC 30 mM
4) A 30 minute pre-treatment at 37° C./5%$CO_2$ of 0.5 ml of either NDGA or NAC was done to all wells except control and S1P 1 $\mu$M before step 3 of section C.

Figure 8:
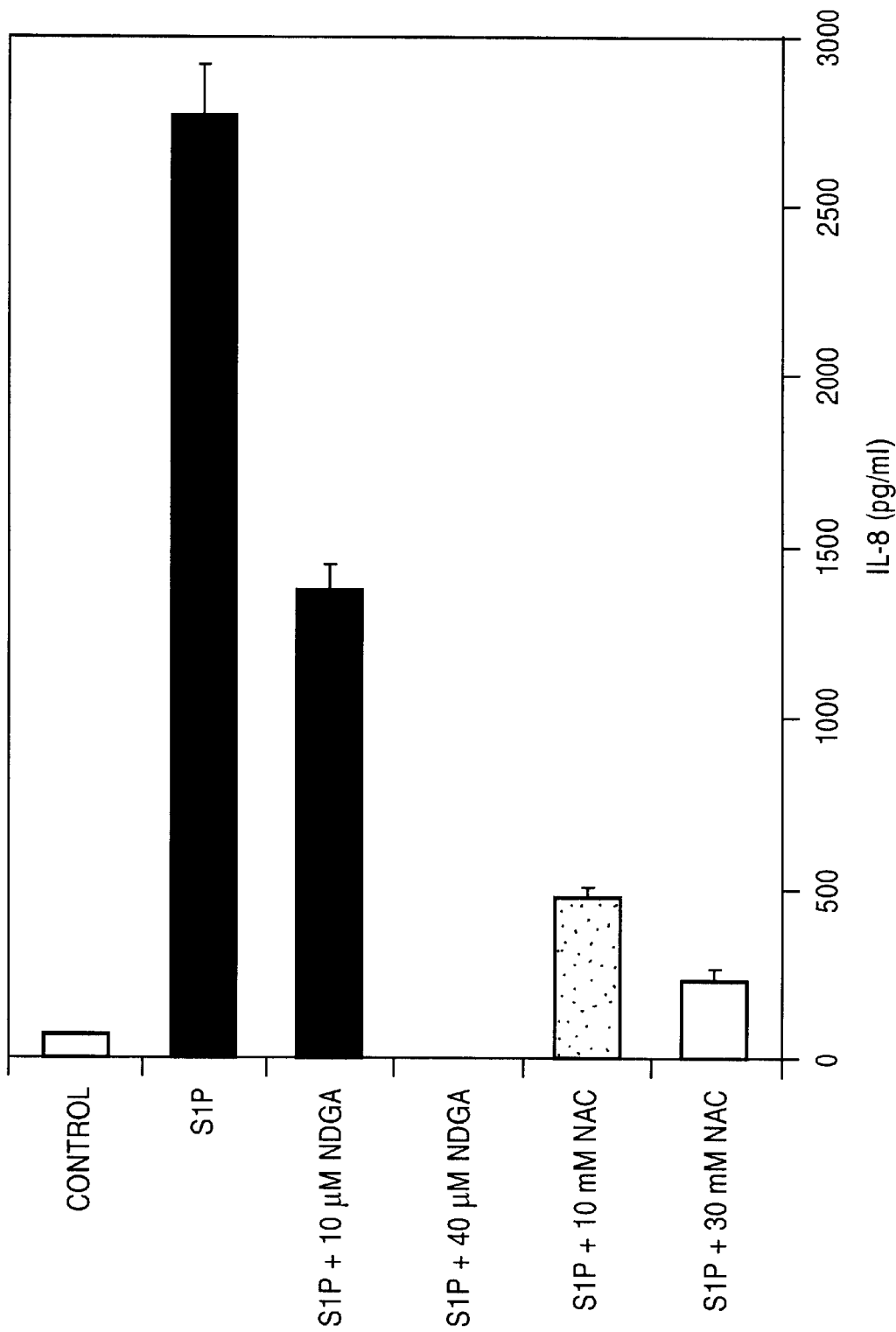
FIG. 8 illustrates the effect the antioxidants NDGA and NAC on the IL-8 response to S1P in HeLa cells.

Results: The IL-8 response to S1P was significantly inhibited by both antioxidants (see FIG. 8). As noted in the literature, the lipophilic antioxidant NDGA, was more potent than the hydrophilic NAC. However, some toxicity of NDGA was seen at 40 $\mu$M, a concentration that completely inhibited the IL-8 response to S1P. Nevertheless, these structurally unrelated antioxidants both inhibited the IL-8 response to S1P, suggesting a cytokine-like pathway mediates S1P signal transduction.

EXAMPLE 9

Suramin and PTX-sensitive IL-8 Response to Edelfosine, an Alkyl Ether Lysophospholipid, in HeLa Cells Edelfosine is an alkyl ether lysophospholipid with potent and selective antitumor activity. In spite of numerous studies highlighting changes in gene expression and signal transduction provoked by edelfosine, conflicting data have been reported on its mechanism of action. Edelfosine inhibits protein kinase C, and thus may have intracellular sites of action. Edelfosine also can inhibit NF-$\kappa$B in at least some cell types. Most important, edelfosine spares normal bone marrow cells at concentrations which kill tumor cells. The mechanism by which this discrimination is effected is unclear. However, given the structural similarity to LPA, the possibility that edelfosine might act on an edg family or LL receptor was considered. Therefore an IL-8 response to edelfosine in HeLa cells in the presence or absence of PTX or suramin was tested.

Procedure #8 For HeLa Cells

Follow Procedure #2 For HeLa Cells with the following exceptions:
1) Solutions required in section C are as follows:
   Suramin 1 mg/ml
   ET-18-$OCH_3$ 10 $\mu$M Stock 10 mM in ethanol Calbiochem, Cat. 341207 Dilute 1:1000
   ET-18-$OCH_3$ 1 $\mu$M Dilute 1:10
   ET-18-$OCH_3$ 3 $\mu$M
   ET-18-$OCh_3$ 3 $\mu$M+suramin 1 mg/ml
2) A 30 minute pre-treatment at 37° C./5%$CO_2$ of 0.5 ml of suramin was done to all wells except control, any PTX and ET-18-$OCH_3$ wells before step 3 of section C.

Results: Edelfosine, like S1P, induced an IL-8 response in HeLa cells at non-cytotoxic concentrations (see FIG. 9). Moreover, this response was potently inhibited by PTX and suramin, suggesting that a $G_{i/o}$-coupled cell-surface receptor may mediate the induction of IL-8 by edelfosine. This receptor may be an edg or LL GPCR, although interaction with a previously identified PAF receptor cannot yet be ruled out. This finding contradicted edelfosine's inhibition of NF-$\kappa$B previously reported in a different cell type. The present invention offers the means to identify and characterize the HeLa cell receptor for edelfosine. Expression of this receptor can then be compared in cells which differ in their cytotoxicity and NF-$\kappa$B responses to edelfosine.

EXAMPLE 10A

Heterologous Expression of EDG-4/H218 in COS-1 Cells Reconstitutes the IL-8 Response to S1P We used a cAMP inhibition assay to show the presence of functional S1P receptors in Swiss 3T3, mouse neuronal B-103 and hamster CHO ProS cells. By comparing the cAMP responses of these cells to the expression profile of the 7 identified edg receptors, we speculated that both EDG-3 and EDGY are likely to be S1P receptors. However, although COS and HEK-293 cells both express abundant RNA for EDG-3, neither cell line shows an IL-8 response to S1P. This suggested that EDGY might selectively mediate the IL-8 response to S1P. Unfortunately, EDG-4 previously could not be measured in HeLa, COS-1 or other primate cells, since it has not yet been cloned from these species. The present invention remedies this situation by providing the sequence of the cloned HEDG-4. However, by transient transfection with a eukaryotic expression vector expressing full-length rat edg-4 cDNA it could be determined if this edg receptor can reconstitute the IL-8 response to S1P in COS-1 cells. The experiment included NF-κB reporter DNA to test for induction of the CAT reporter gene in parallel with the IL-8 response.

A. DEAE/Dextran Cell Suspension Transient Transfection.

Transfection was done as described in Anal Biochem 218:460 (1994).

a) Solutions:
RSC: 49 ml RPMI 1640 (Gibco; Cat. 21870-076)+1 ml Fetal calf serum +50 μl of 100 mM chloroquine (Sigma; Cat. C6628)
DEAE/RSC: 18.4 ml RSC+1.6 ml of 10 mg/ml DEAE/Dextran (Promega; Cat. E112A)

b) Transfection procedure:
1) 6 ml RSC was added to 4–50 ml tubes. The following amounts of DNA were added:

| Tube | DNA (μg)/tube | | | |
|---|---|---|---|---|
| | 1 | 2 | 3 | 4 |
| pcDNA3 | 5 | 5 | — | — |
| pC3-redg4 (rat edg-4) | — | — | 5 | 5 |
| 6xNFκB-tk-CAT5 | 5 | 2 | 5 | 2 |
| pBluescript | — | 3 | — | 3 |

The tubes were incubated at 37° C. until DEAE/RSC solution was made.

2) 6 ml of DEAE/RSC solution was added to each tube and incubated at 37° C. for 2 min.
3) 1.5 ml COS-1 cell suspension ($5.5 \times 10^6$ cells total) in RSC was added to each tube and incubated for 105 min in 37° C. incubator. Tubes were mixed every 20 min.
4) Following incubation, tubes were spun for 5 min, cell pellets were washed with DMEM/F12+10% FBS once and then resuspended in 10 ml media. Cells were plated in 24-well plates at $0.2 \times 10^6$ cells/well.

B. Treatment.

After 2 days (~40 hrs), cells were serum-starved (0.5% FBS media) with or without PTX (50 ng/ml) for at least 6 hrs and treated overnight with 0.5% FBS media, S1P (5 μm) in 0.5% FBS media or TPA (100 ng/ml) in 0.5% FBS media. 500 μl treatment volume was used. Supernatants were microfuged at 14,000 rpm for 10 min., transferred to new eppendorf tubes and stored at −20° C. for future IL-8 ELISA determination.

C. IL-8 ELISA (Enzyme-Linked ImmunoSorbent Assay).

The procedure as outlined in Procedure for HeLa Cells (D) was followed, using 50 μl of sample per ELISA determination in duplicate.

Results: COS-1 cells transfected with the EDG-4 expression plasmid showed a 2-fold increase in IL-8 release when treated with 5 μm S1P as compared to untreated cells (see FIG. 1A.). No IL-8 response to Sip was seen in control cells transfected with the empty expression vector pcDNA3. Moreover, the IL-8 response to S1P in EDG-4 transfected cells was pertussis toxin sensitive, since control and EDG-4 transfected cells showed similarly low levels of IL-8 in the presence of PTX. As expected, PTX did not inhibit the IL-8 response to TPA, which is not mediated by a GPCR. Despite the presence of abundantly expressed endogenous EDG-3 RNA, COS-1 cells do not show an IL-8 response to S1P. However, heterologous expression of rat EDG-4 reconstitutes a PTX-sensitive IL-8 response to S1P, similar to the endogenous receptor expressed in HeLa cells. Therefore, the functional assay described herein critically depends on the expression of specific edg and/or LL receptors which are expressed endogenously in HeLa cells, and which can be heterologously expressed in the form of EDG-4, and perhaps other related GPCRs.

EXAMPLE 10B

Expression of Endogenous Edg Receptors in 293-EBNA Cells

To determine the more appropriate cells for transfection with the edg cDNA receptors, a Northern Blot experiment was conducted for HeLa, COS and 293-EBNA cells. As can be seen from FIG. 10B, the Northern blot shows that 293-EBNA cells has no visible expression of any of the edg receptors other than possible EDG-5. In conjunction with the Northern Blot experiment, each of these cells, HeLa, COS and 293-EBNA were exposed to TPA, LPA and S1P and then measured for IL-8 production. The 293-EBNA cells showed no IL-8 production for LPA and S1P indicating that there is no expression of any EDG receptor.

EXAMPLE 11

Heterologous Expression Studies Using Luciferase Assay

To improve on the 2-fold CAT reporter gene induction observed in the previous experiment, 2 changes were made. First, the NF-κB response element was reconstructed in a new reporter construct (p4Luc) suitable for stable maintenance as an episome in primate cells. Second, transient transfection was carried out in 293-EBNA cells (Invitrogen; Cat. R620-07), an EBNA-1 expressing derivative of HEK-293. The p4-Luc reporter used the backbone of pREP4 (Invitrogen; Cat. V004-50), which contains the EBV origin of replication ($EBV_{ori}$), as well as the EBNA-1 viral antigen required to maintain $EBV_{ori}$-containing plasmids as stable episomes in primate cells, and a prokaryotic selection marker. A dominant eukaryotic selection marker for zeocin resistance was substituted for the neo marker of pREP4, and a luciferase cassette was cloned into the multiple cloning site for expression in pREP4. The promoter of pREP4 was then excised and replaced with a multi-cloning site for introduction of promoter/enhancer inserts. The NF-κB-tk insert of the previous CAT reporter was subcloned into this site and all cloning junctions were sequenced to verify the structure of the plasmid, called NF-κB-tk-p4Luc.

Assay #1

Monolayer Transient Transfection Protocol for 293-EBNA

Day 1:
1) 150 mm plates of 293-EBNA obtained from Invitrogen (Cat. R620-07) with a confluency of ~80% were used for transfection.

2) 6.6 μg NF-κB-tk-p4Luc reporter DNA and 6.6 μg of pC3-redg4 (expressing rat EDG-4), or pcDNA3 DNA was diluted in 500 μl OPTI-MEM (Gibco; Cat. 31985-062)

3) 96.8 μl Lipofectamine (Gibco; Cat. 18324-020) was diluted in 500 μl of OPTI-MEM.

4) The 2 solutions were mixed gently and the tube was incubated for 30 min at room temperature.

5) The 293-EBNA plates were washed once with PBS and 13 ml OPTI-MEM was added to each plate.

6) 6 ml OPTI-MEM was added to each transfection tube and this was added to a plate of 293-EBNA cells. The plates were left for 4 hrs at 37° C. in a 5% $CO_2$ incubator.

7) After 4 hrs, the media was removed and replaced with fresh 10% FBS media.

Day 2:

1) Transfected cells were washed, trypsinized with 1×trypsin, resuspended in 10 ml media and counted.

2) $0.02 \times 10^6$ cells were plated per well of a 96-well Blackview plate coated with polyD-lysine. No cells were plated in the outside wells of the 96well plate. Two 96-well plates were seeded for each transfection.

Day 3:

1) Cells were washed with PBS and 140 μl serum-free media (SFM) added to each well. Plates were incubated in 37° C. incubator for 6 hrs.

2) After 6 hrs, media was removed and cells treated with compounds diluted in 0.5% FBS media (140 μl added to each well).

The following treatments were used:

pcDNA3:
Untreated, LPA 10 μM, LPA 5 μM, S1P 10 μM, S1P 2 μM, SPC 3 μM, SPC 1 μM, edelfosine 1 μM, edelfosine 500 nM, LPC 1 μM, LPC 500 nM, 20% FBS (Gibco; Cat. 10437-028), TPA (50 ng/ml), TPA (25 ng/ml).

pC3-EDG-4:
Untreated, LPA 10 μM, LPA 5 μM, S1P 10 μM, S1P 5 FM, S1P 1 μM, SPC 3 μM, SPC 1 μM, edelfosine 1 μM, edelfosine 500 nM, LPC 1 μM, LPC 500 nM, 20% FBS, TPA (50 ng/ml), TPA (25 ng/ml).

3) Cells were treated for 24 hrs.

Day 4:

Luciferase Assay

1) Luclite kit (Packard; Cat. 6016911) was used for luciferase assay. All reagents were brought to room temperature before use.

2) Supernatant was transferred to a new 96-well plate and stored at −20° C. for future IL-8 measurement.

3) 50 μl 0.5M HEPES pH 7.8 buffer (1 mM $MgCl_2$, 1 mM $CaCl_2$) was added to all wells of 96-well plate. Black adhesive backing (Polyfitronics) was aligned to the bottom of the viewplate.

4) Luclite substrate was made up by adding 10 ml substrate diluent to 1 vial lyophilized substrate. Reconstituted substrate was kept under a dark container. 50 μl substrate was added to each well.

5) A clear adhesive plate sealer was adjusted onto the viewplate and sealer rubbed over the plate with a Kimwipe. The plate was shaken on a plate shaker at 500 rpm for 5 seconds right side up and then upside down. A stop plate was placed on top of the blackview plate to keep it in the dark.

6) Plates were incubated at room temperature for 30 min.

7) After incubation, plates were counted in a 12-detector Packard Top Count on a program without dark delay.

Figure 11:
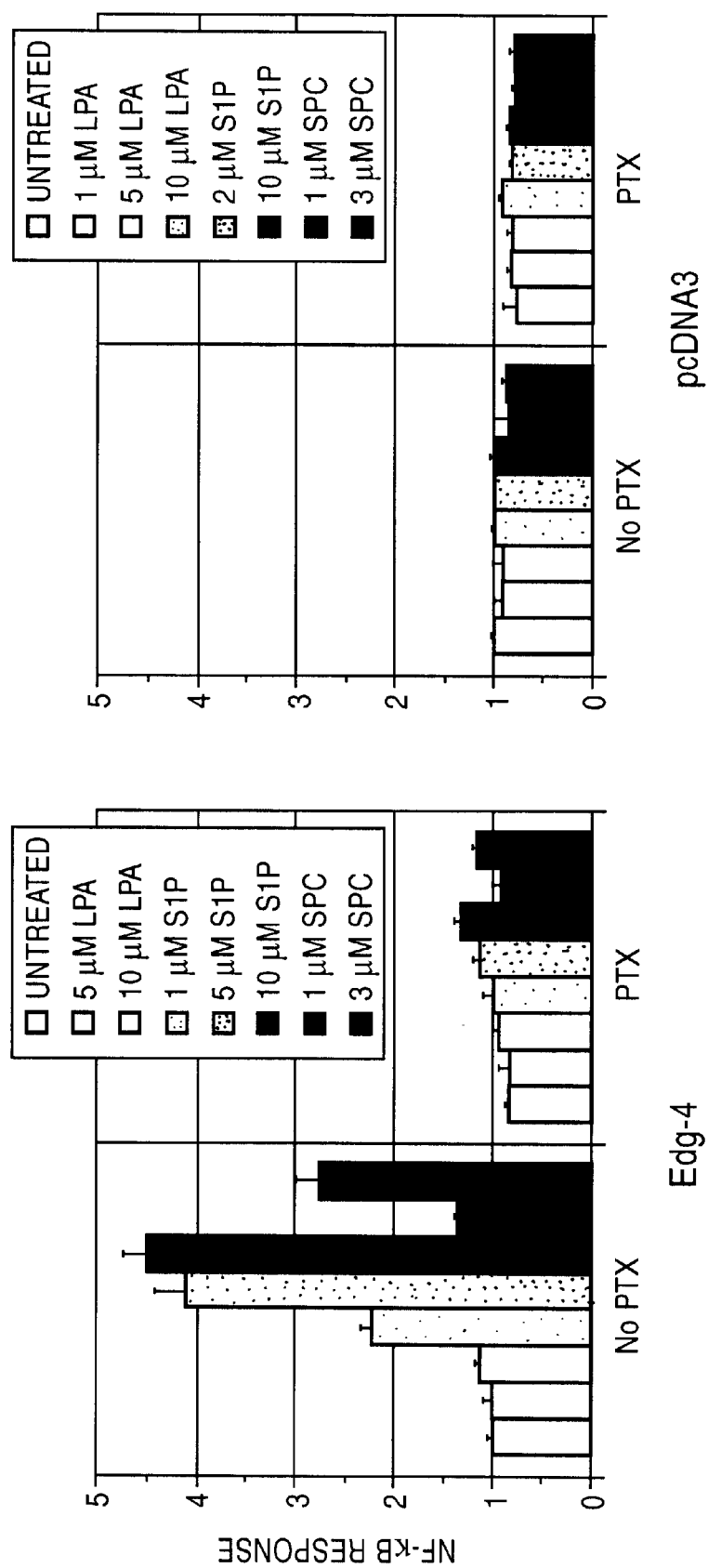
FIG. 11 illustrates the NF-κB reporter response to S1P, LPA and SPC in 293-EBNA cells cotransfected with an edg4 expression plasmid and a NF-κB-tk-p4Luciferase reporter plasmid.

Results: 293-EBNA cells cotransfected with pC3-redg4 and the NF-κB-tk-p4Luc reporter showed a 4–4.5-fold increase in luciferase activity when the cells were treated with 5 μM or 10 μM S1P (see FIG. 11). EDG-4 expressing cells treated with 1 μM S1P showed a 2-fold increase in luciferase activity. Pretreatment with PTX inhibited the response to S1P at all concentrations. No increase in luciferase activity was seen in cells cotnansfected with the empty expression vector pcDNA3 and the luciferase reporter, and no change in luciferase activity was seen with PTX pretreatment in these cells. SPC also induced the reporter gene in EDG-4 expressing cells, but not control cells, and this response was also PTX-sensitive. The potency of SPC was apparently lower than that of S1P, though this was not rigorously assessed. TPA strongly induced the NF-κB reporter, and PTX did not affect this induction, as expected. No induction of the reporter was seen with any of the other ligands assayed, either in pC3-redg4 or pcDNA3-transfected cells.

These results strongly support the assignment of EDG-4 as a PTX-sensitive S1P receptor which signals via NF-κB and inflammatory gene expression. Furthermore, the results provide a definitive validation of the receptor-dependent functional assays, which comprise one aspect of the present invention.

The isolated receptor, which is endogenously expressed in HeLa cells, also constitutes one embodiment of the current invention. Numerous methods well-known to those skilled in molecular biology and expression cloning are available to isolate the edg or LL GPCR which fulfills the criteria we have established herein. These include the screening of a HeLa cDNA library (Invitrogen; Cat. A550-26) with degenerate or specific oligonucleotides derived from EDG-4, the EDG-1/EDG-3/EDG-4 subfamily, or the broader edg family including EDG-1 and EDG-2 paralogs, as well as screening by hybridization with rat EDG-4 coding region DNA. Expression cloning should also easily identify an edg/LL receptor cDNA, cloned in a suitable expression vector, which confers on 293-EBNA cells the capacity to produce IL-8 or induce a NF-κB reporter in response to S1P,SPC and/or LPA in a PTX-sensitive manner.

Assay #2

The IL-8/NF-κB response met all the criteria of a receptor-dependent, robust and reproducible functional assay of EDG/LL receptors. This assay was applied to various cloned EDG receptors for responsiveness to natural LL, as well as complex mixtures such as fetal bovine serum. In this way, agonist ligands for the orphan EDG receptors are identified, and EDG receptors which are capable of inflammatory responses are identified.

Transient Transfection Protocol for 293-EBNA

Day 1:

The above protocol for assay 1 was followed except for the following changes:

1) 100 mm plates of 293-EBNA with a confluency of ~80% were used for transfection.

2) 3 μg NFκB-tk-p4Luc reporter DNA and 3 μg pC3-hedg1, pC3-hedg3, pC3-redg4, pC3-hedg5 or pcDNA3 DNA was diluted in 240 μl OPTI-MEM (Gibco; Cat. 31985-062)

3) 22 μl lipofectamine (Gibco; Cat. 18324-020) was diluted in 240 μl OPTI-MEM.

4) The 293-EBNA plates were washed once with PBS and 7 ml OPTI-MEM was added to each plate.

5) DNA/lipofectamine mixture was added to each plate of 293-EBNA cells. The plates were left for 4 hrs at 37° C. in a 5% $CO_2$ incubator.

Day 2:

1) 0.01×10⁶ cells were plated per well of a 96-well Blackview plate coated with polyD-lysine. No cells were plated in the outside wells of the 96-well plate.

Day 3:

The following treatments were used for all transfections: Untreated, S1P 3 μM, LPA 3 μM, psychosine 3 μM (Sigma; Cat. P-9256, Stock 10 mM in methanol), SPC 3 μM, LPC 1 μM, sphingosine 3 μM, 20% FBS, TPA (20 ng/ml), edelfosine 1 μM, lysosulfatide 3 μM.

Figure 12:
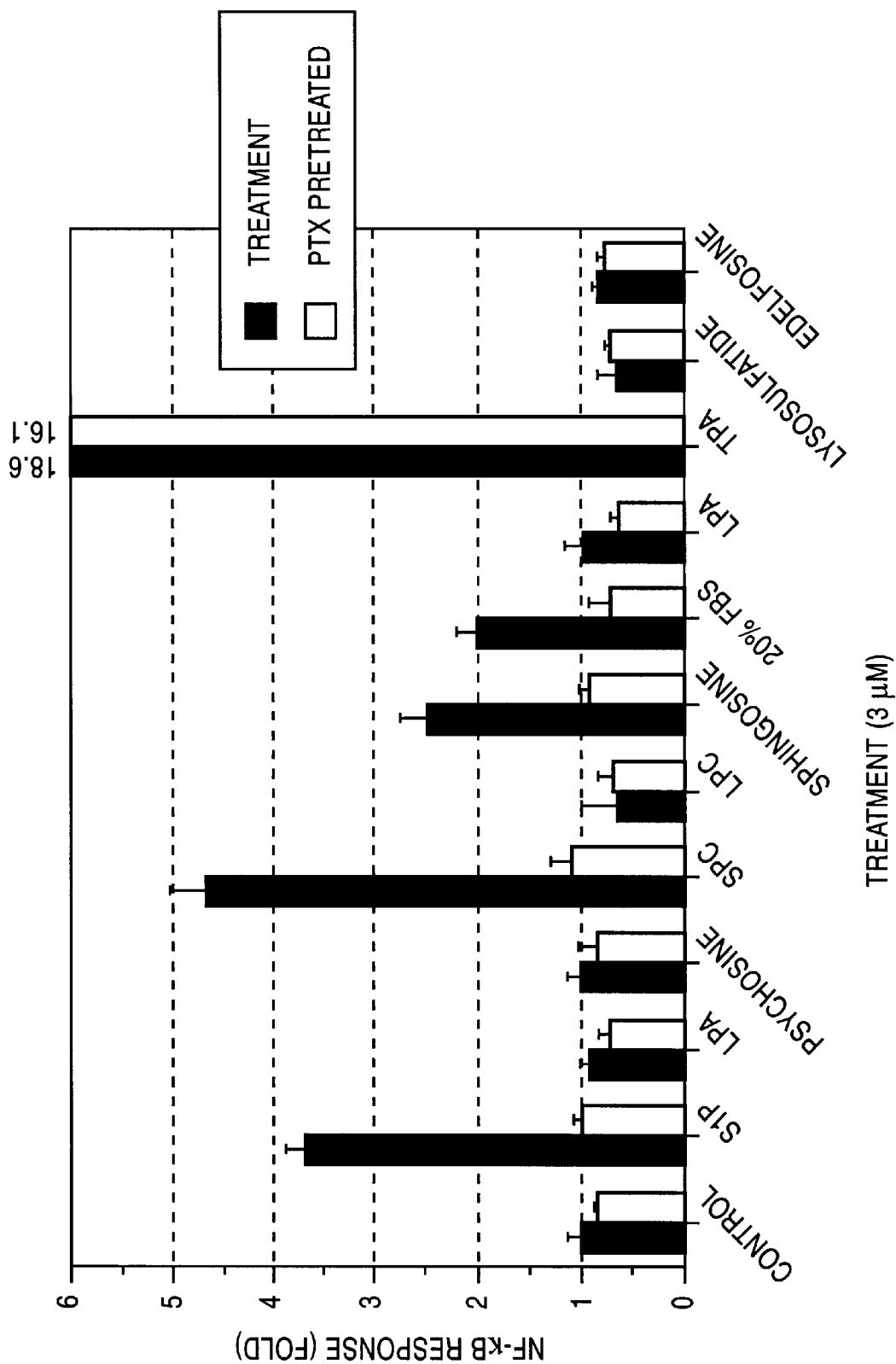
FIG. 12 illustrates the NF-κB reporter response to S1P, LPA, pyschosine, SPC, LPC, sphingosine, 20% FBS, TPA, lysosulfatide and edelfosine in 293-EBNA cells cotransfected with an EDG-4 expression plasmid and an NF-κB-tk-p4Luciferase reporter plasmid, as well as the PTX sensitivity of this response.

Results: 293-EBNA cells transfected with the pC3-redg4 construct showed a 3.5-fold increase in luciferase activity when the cells were treated with 3 μM S1P (see FIG. 12). In this experiment 3 μM SPC showed a 4-fold increase in luciferase activity. As seen previously, PTX efficiently inhibited the response to S1P and SPC. No response to S1P or SPC was seen in pcDNA3-transfected 293-EBNA cells, confirming previous results. This demonstrates that the luciferase response to S1P and SPC is critically dependent on the heterologous expression of EDG-4 in the 293-EBNA cells.

Cells transfected with rat EDG-4 or human EDG-5 and treated with 20% FBS also showed 2-fold increase in luciferase activity and PTX efficiently inhibited this response. No such response was seen to 20% FBS in pcDNA3-transfected cells, and PTX had no effect on the luciferase expression of the control cells in the presence or absence of 20% FBS. S1P is present in FBS as a result of release from clotted platelets, and can account for the increase in luciferase observed in EDG-4 expressing cells treated with 20% serum. We conclude that 20% serum contains 1 or more agonists for EDG-5, which may consist of LPA or related LL. Moreover, EDG-5, like EDG-4, is capable of responding through proinflammatory NF-κB signaling pathways.

These results, in addition to confirming the previous experiment, support a broad application of this robust and reproducible functional assay in screening for agonists and antagonists of edg and LL receptors. With a positive receptor-induced readout such as IL-8 production or the NF-κB reporter gene, experiments can be carried out on transiently transfected cells, allowing for rapid and flexible screening of a target edg/LL receptor. This contrasts with an inhibition assay such as the $G_i$-mediated inhibition of cAMP production by forskolin. In the latter type of assay, stable cell lines are necessary so that the decrease will not be masked by the uninhibited response of untransfected cells.

Additionally, this approach can identify agonists for orphan edg/LL receptors, provided the receptors respond through the inflammatory pathways described herein. Even where the natural agonist of an edg receptor is unknown, screening for agonists is possible with these robust and reproducible readouts. Using this approach, agonists can be identified for heterologously (or endogenously) expressed edg/LL receptors whether applied as chemically pure substances, ligand clips, or in biological preparations such as serum. It is a tractable proposition to purify, isolate, characterize and synthesize the active LL from serum with this reliable bioassay in hand.

Assay #3

NE-κB activates gene expression by binding to specific DNA sequences found in the promoters of genes regulated by this inflammation-related transcription factor. A different sequence, the serum response element (SRE) is found in the promoters of genes which are upregulated by the addition of serum to serum-starved cells. Both LPA and S1P are found in micromolar concentrations in serum, and have been shown to mediate a significant part of the SRE upregulation caused by serum. Since SRE activation reflects different and distinct pathways from those leading to NF-κB activation, EDG-4 and the closely related EDG-1 and EDG-3 receptors were tested for induction of a SRE reporter gene by S1P or SPC. The SRE reporter was identical to the NF-κB reporter, except that the NF-κB binding sites were replaced with 2 SRE sites. The new reporter was called 2XSREtk-p4Luc-zeo.

Transient Transfection Protocol for 293-EBNA (Assay 3):

Day 1.

The protocol described in Example 11 for Assay 1 was followed except for the following changes:

1) 100 mm plates of 293-EBNA with a confluency of ~80% were used for transfection.
2) SRE Cotransfection: 0.5 μg of 2XSREtk-p4Luc-zeo reporter DNA and 3.5 μg pcDNA3, EDG-1, EDG-3 (pC3-hE3HP2, different from the clone used in Assay 2 of Example 11) or the newly cloned human EDG-4 (pC3-hedg4#36); NF-κB Cotransfection: 2 μg 6XNFκBtk-p4Luc-zeo reporter DNA and 2.0 μg pcDNA3, EDG-1, EDG-3 (pC3-hE3HP2), or EDG-4 (pC3-hedg4#36). Expression plasmid and reporter plasmid DNA samples were combined and diluted in 750 μl of DMEM/F12 (serum free media) and 20 μl Plus Reagent (Lipofectamine Plus Kit, Life Technologies Cat. 10964-013), and incubated at room temperature for 15 min.
3) 30 μl Lipofectamine Reagent (Lipofectamine Plus Kit) was diluted in 750 μl DMEM/F12. The diluted Lipofectamine was then combined with the DNA/Plus mixture and incubated at room temperature for 15 min.
4) The 293-EBNA plates were washed once with PBS and 5 ml DMEM/F12 was added to each plate.
5) DNA/Plus/Lipofectamine mixture was added to each plate of 293-EBNA cells. The plates were left for 3 hr at 37° C. in a 5% $CO_2$, incubator.
6) The transfection medium was replaced with serum-free DMEM/F12 for cells transfected with 2XSREtk-p4Luc-zeo reporter DNA and with DMEM/F12 plus 10% FBS for cells tansfected with 6XNFκBtk-p4Luc-zeo reporter DNA.

Day 2.

2) Transfected cells were harvested by trypsinization and 50,000 cells per well were plated in 96-well Blackview plates coated with poly D-lysine (Becton Dickinson Labware, Cat. 40640). No cells were plated in the outside wells of the 96-well plate.

Day 3.

1) Media for cells transfected with 6XNFκBtk-p4Luc-zeo reporter DNA was replaced with DMEM/F12 plus 0.5%FBS.

Day 4.

1) Media was removed and cells treated with compounds diluted in DMEM/F12 media. The following treatments were used for all transfections: Untreated: serun-free medium alone, S1P (3 μM), SPC (3 μM).
2) The cells were treated for 6 hours.
3) Luciferase assay was performed.

Figure 13:
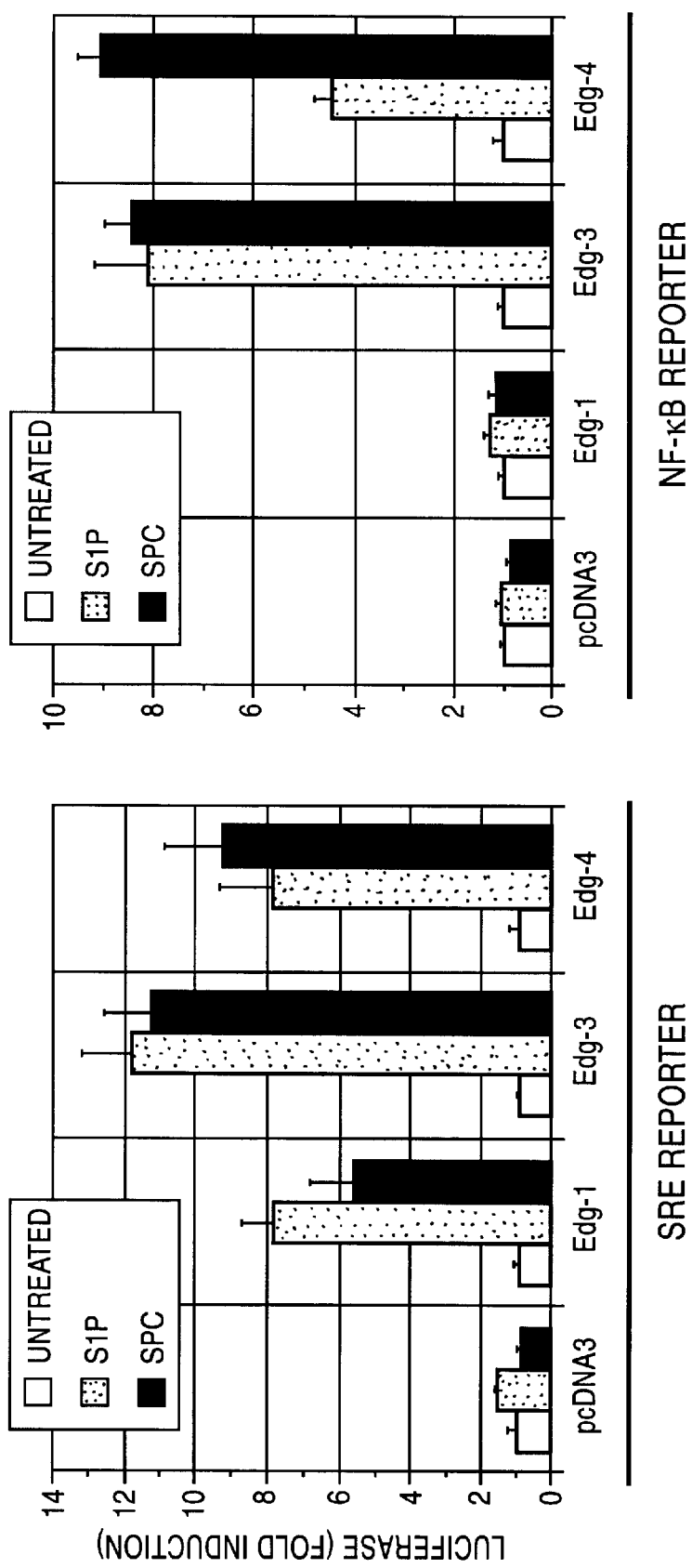
FIG. 13 illustrates the EDG-1, EDG-3 and EDG-4 receptor response to S1P or SPC using (A) the SRE reporter gene assay or (B) the NF-κB-tk-p4Luciferase reporter assay.

Cotransfection of EDG-1 and 2XSREtk-p4Luc-zeo reporter resulted in a 8-fold increase in luciferase activity after treatment with 3 μM S1P, and a 6-fold increase after treatment with 3 μM SPC (FIG. 13A). In contrast, no increase in luciferase activity was seen in S1P- or SPC-treated cells cotransfected with EDG-1 and the 6XNFκBtk-p4Luc-zeo reporter (FIG. 13B). Thus, although the EDG-1 receptor is fully functional, and recognizes S1P and SPC as agonists, the NF-κB reporter was not induced. This result confirms the finding that EDG-1 is a non-inflammatory subtype of S1P/SPC receptor.

Although the original human EDG-3 clone did not produce a NF-κB response to S1P or SPC, a different human EDG-3 clone, derived from human pancreas (pC3-E3HP2), was cotransfected with the SRE reporter and this clone showed a robust 12-fold SRE response to 3 μM S1P and 11-fold response to 3 μM SPC (FIG. 13A). A control cotransfection of the empty expression vector pcDNA3 with the SRE reporter showed a small but reproducible response to S1P (about 1.5-fold) but not SPC (FIG. 13A). The robust SRE response of the pancreas EDG-3 clone confirms our hypothesis that both EDG-1 and EDG-3, in addition to the closely related EDG-4, function as S1P/SPC receptor subtypes. Moreover, a similar induction of the NF-κB reporter gene (about 8-fold) was seen both in S1P- and in SPC-treated cells, compared to untreated controls, after cotransfection with EDG-3 (FIG. 13B). No such induction was seen in the cells cotransfected with pcDNA3 and the NF-κB reporter gene (FIG. 13B), indicating that the NF-κB response to S1P and SPC in EDG-3 transfected cells was not due to endogenous receptors. Therefore, EDG-3 (but not EDG-1) must be considered to be another edg/lysolipid receptor subtype which can mount an inflammatory response to S1P and other lysosphingolipids.

Like EDG-1 and EDG-3, human EDG-4 (See Examples 12, 13 and 14 for identification and cloning of HEDG-4) also responded through the SRE reporter gene, showing a 8-fold response to S1P and a 9-fold response to SPC, relative to untreated control cells (FIG. 13A). As we had previously observed with the rat EDG-4 expression construct tested in Example 11, human EDG-4 also mediated a robust NF-κB -response, showing a 4.5- and 9-fold induction of the reporter gene to S1P and SPC, respectively (FIG. 13B). Therefore, induction of inflammatory gene expression pathways is a conserved feature of EDG-4 in humans and rats, and likely reflects a fundamental biological aspect of receptor function.

Together, these results suggest that the SRE response is a shared feature of many different edg/lysolipid receptors, and can be used to verify the response of intact, functional receptors to their cognate agonist(s). On the other hand, the NF-κB response is shared by a subset of edg/lysolipid receptors which are specialized to mobilize inflammatory gene expression and immune system recruitment. Since EDG-1, EDG-3, EDG-4 and EDG-7 are all S1P/SPC receptors, their varying and even overlapping tissue distribution and inducibility frustrate the meaningful design, screening and therapeutic testing of anti-inflammatory S1P analogs unless the subtype specificity of inflammatory signaling is appreciated. This complexity highlights the value and utility of the recombinant inflammatory lysolipid receptors and the functional assays specified herein.

EXAMPLE 12

Identification of Human Expressed Sequence Tags (ESTs) Homologous to Rat H218 (EDG-4)

A BLAST search of the complete GenBank database was conducted with the sequence of an oligonucleotide RE4_181F [5'-GAGAAGGTTCAGGAACACTACAATTACACCAAGGA-3'], based on the sequence of rat EDG-4. The search identified a human EST (GenBank accession AA804628), which was 88% identical to the corresponding region of rat EDG-4 cDNA (GenBank accession U10699). A subsequent TBLASTN search of the EST database using the predicted polypeptide product of the rat EDG-4 cDNA (according to accession number U10699) revealed 2 other matching EST's (accession AA827835 and AA834537) in addition to the original human EST. The 3 EST's encompassed the predicted translation start site of human EDG-4 (based on similarity to rat EDG-4), overlapped each other extensively, and together spanned some 109 codons of the N-terminal portion of the human EDG-4 polypeptide (FIG. 14). The predicted fragment of the human EDG-4 polypeptide showed 90.1% identity and 93.3% similarity to the equivalent fragment of rat EDG-4, suggesting the human polypeptide is an ortholog of the rat EDG-4 gene product, rather than a closely related gene product. A BLAST search was then conducted with the complete sequence of rat EDG-4 cDNA (accession number U10699) against the EST database. In addition to the previously identified EST's, 2 EST's apparently derived from the 3'-untranslated region of human EDG-4 cDNA adjacent to the poly(A) tail were found (AA767046 and N93714). Of the 5 human EST's identified in total, only N93714 was present in the public database before Feb. 19, 1998. This EST was derived from the 3' end of a 1421 bp cDNA insert which contained no coding region. The closest match recorded in the DBEST database entry (accession 500502) was a cGMP phosphodiesterase. The 5' end of the clone had been sequenced and given the GenBank accession W21101; however, similarity to other cDNAs was obscured by the presence of an Alu sequence.

EXAMPLE 13

Survey of Potential cDNA Sources Using 5' End and 3' End Dialnostic PCR

To evaluate possible sources of human EDG-4 cDNA from HeLa cells (which express the inflammatory S1P/SPC receptor) and lung (a predominant site of EDG-4 expression in rat) for the presence of the desired cDNA fragments, diagnostic PCR primers were designed from the cluster of 5' end EST's (AA804628, AA834537 and AA827835) and 3' end EST's (N93714 and AA767046):

5' end primers:
HE4-DF1 [5'-ATTATACCAAGGAGACGCTGGAAAC-3']
HE4-DR1 [5'-AGAGAGCAAGGTATTGGCTACGAAG-3']
3' end primers:
HE4-DF2 [5'-TCCTCTCCTCGTCACATTTCCC-3']
HE4-DR2 [5'-GCATTCACAAGAAATTACTCTGAGGC-3']

Template sources: 1) cDNA library from WI-38 lung fibroblasts (Origene Technologies Inc., Cat. DLH-102); 2) cDNA library from human lung (Clontech, Cat. 7114-1); 3) cDNA library from HeLa cells (Invitrogen, Cat. A550-26); 4) First strand cDNA prepared in-house from HeLa cell total RNA. Each template was amplified with each pair of primers using the Expand™ PCR system from Boehringer Mannheim (Cat. 1681-842).

Each reaction contained the following reagents:

| | |
|---|---|
| 2 μl | 10x PCR Buffer 3 |
| 0.4 μl | 25mM dNTP mix |
| 0.6 μl | Primer HE4-DF1 or HE4-DF2 (10 μM) |
| 0.6 μl | Primer HE4-DR1 or HE4-DR2 (10 μM) |
| 0.3 μl | Expand ™ enzyme (3 units) |
| 15.1 μl | water |
| 1 μl | cDNA template |

PCR conditions:

| | |
|---|---|
| Incubate: | 94° C. for 2 min |
| 30 cycles: | 94° C. for 40 sec |
| | 55° C. for 1 min |
| | 68° C. for 40 sec |
| Incubate: | 68° C. for 8 min |
| Hold: | 4° C. |

The expected ~200 bp 5' PCR product was successfully amplified from WI-38 lung cDNA (Origene), and from the first strand cDNA prepared in-house from HeLa cells. The ~200 bp 3' PCR product was successfully amplified from human lung cDNA libraries (Origene and Clontech) and HeLa cDNA library (Invitrogen), but not from the random hexamer-primed HeLa first strand cDNA. Thus, the WI-38 human lung fibroblast cDNA library (Origene) appeared to be the most likely source of full length human EDG-4 cDNA clones. More important, the successful amplification of a fragment of human EDG-4 cDNA from HeLa provides a concrete demonstration of EDG-4 expression in this S1P/SPC-responsive cell line, and directly supports the claim of composition of matter on EDG-4 and inflammatory S1P/SPC receptors isolated from HeLa cells. Together with fill-length sequence information presented below, full-length cloning and expression of the inflammatory EDG-4 receptor from HeLa cells is reduced to a simple technical exercise for one skilled in the art.

EXAMPLE 14

Cloning of the Complete Coding Region of Human edg-4 cDNA

Two new primers were designed to amplify the complete coding region and most of the 3'-untranslated region. The primers were based on the EST sequences spanning the translation start site, and the EST sequences representing putative 3'-untranslated sequences of human edg-4. Provided that these primers bind appropriately to a common template (ie. human edg-4 cDNA), a ~2.4 kb PCR fragment should be amplified, containing the complete coding region. These primers were used in a PCR reaction with the WI-38 human lung fibroblast cDNA library (Origene) as follows:

HE4-DF3 [5'-GAGCCCCACCATGGGCAGCTTGTACT-3']
HE4-DR2 [5'-GCATTCACAAGAAATTACTCTGAGGC-3']

Each reaction contained the following reagents:

| | |
|---|---|
| 5 μl | 10x PCR Buffer 3 |
| 1.0 μl | 25 mM dNTP mix |
| 1.5 μl | Primer HE4-DF3 (10 μM) |
| 1.5 μl | Primer HE4-DR2 (10 μM) |
| 0.75 μl | Expand ™ enzyme (2 units) |
| 39.25 μl | water |
| 1 μl | cDNA template (250 ng or 500 ng of DNA) |

PCR conditions:

| | |
|---|---|
| Incubate: | 94° C. for 2 min |
| 10 cycles: | 94° C. for 40 sec |
| | 60° C. for 40 sec |
| | 68° C. for 5 min |
| 25 cycles: | 94° C. for 40 sec |
| | 60° C. for 40 sec |
| | 68° C. for 3 min |
| Incubate: | 68° C. for 8 min |
| Hold: | 4° C. |

Amplified reactions from 250 ng (tube 227-45) and 500 ng (227-50) of cDNA template each contained 3 PCR products 2 kb or larger. The PCR reaction and the DNA fragments from the gel were purified using QIAquick PCR purification kit (Qiagen Cat. 28106) and QIAquick gel extraction kit (Qiagen, Cat. 28704), respectively. Diagnostic PCR reactions were carried out on each of the 3 PCR products, and all 3 yielded the expected diagnostic PCR products using both the 5' end and 3' end primer pairs. Because they differed in size (~2 kb, 2.2 and 2.4 kb) and yet amplified with primers from the translation start and the 3'-untranslated region, all 3 may represent different alternatively spliced edg-4 transcripts.

The 3 PCR products were used as templates to reamplify human edg-4 with primers containing restriction sites suitable for cloning into an expression vector. Two different 3'-end primers were selected with longer (HE4-DR3) or shorter (HE4-DR4) 3'-untranslated regions. The following PCR primers and PCR conditions were used:

2 HE4-DF4 [5'-TTTAAAAAGCTTCCCACCATGGGCAGCTTGTACT-3']
HE4-DR3 [5'-TATATATCTAGACATTCACAAGAAATTACTCTGAGGC-3']
HE4-DR4 [5'-TATATATCTAGAGGAAATGTGACGAGGAGAGG-3']

Each reaction contained the following reagents:

| | |
|---|---|
| 5 μl | 10x PCR Buffer 3 |
| 1.0 μl | 25 mM dNTP mix |
| 1.5 μl | Primer HE4-DF4 (10 μM) |
| 1.5 μl | Primer HE4-DR3 or HE4-DR4 (10 μM) |
| 0.75 μl | Expand ™ enzyme (5 units) |
| 39.25 μl | water |
| 1 μl | DNA |

PCR conditions:

| | |
|---|---|
| Incubate: | 94° C. for 2 min |
| 28 cycles: | 94° C. for 40 sec |
| | 60° C. for 40 sec |
| | 68° C. for 3.5 min |
| Incubate: | 68° C. for 8 min |
| Hold: | 4° C. |

The amplified fragments were purified using QIAquick PCR purification kit (Qiagen Cat. No.28106). The DNAs were restricted with HinDIII and XbaI, purified using QIAquick PCR purification kit (Qiagen Cat. No.28106) and QIAquick gel extraction kit (Qiagen, cat. no. 28704) and subcloned into HinDIII and XbaI-restricted pcDNA3

(Invitrogen; discontinued). Sequencing was carried out using fluorescent dye-labeled dideoxy terminators and an Perkin-Elmer/ABI 377 automated sequencing apparatus, with primers designed from vector sequences flanking the edg-4 insert, or from known rat or human edgy sequence. The human edg-4 sequence was compiled and assembled using the Lasergene DNAStar component SeqMan. Comparisons to rat edgy were carried out with the Wisconsin Group's GCG modules FRAMESEARCH, GAP, FASTA and BLAST.

A 1,170 bp span of the ~2.4 kb human edg-4 cDNA insert was sequenced extensively. The cDNA sequence as derived from clones pC3-hedg4#5 and pC3-hedg 4#36 is presented in FIG. 15A. This region included 37 bp of putative 5'-untranslated region, a 1059 bp open reading Same (excluding the stop codon) corresponding to the complete human edgy coding region, and 74 bp of 3'-untranslated region adjacent to the coding region. This cDNA sequence showed 82.1% identity to the rat edg-4 cDNA sequence of GenBank entry U10699 over a 1129 bp region spanning the complete open reading frames of the rat and human edg-4 polypeptides, respectively.

The predicted human edg-4 translation product (FIG. 16A) showed 90.1% identity, and 92.3% similarity to the rat EDG-4 polypeptide, consistent with its identification as the human ortholog of rat EDG-4. An alignment of the rat and human EDG-4 amino acid sequences is shown in FIG. 17A. The human EDG-4 polypeptide sequence has features typical of a G protein-coupled receptor, including 7 putative transyembrane domains, multiple potential intracellular phosphorylation sites and a single potential extracellular N-glycosylation site. The locations of these features are indicated in FIG. 16A.

FIGS. 15B and 16B illustrate the cDNA sequence and amino acid sequence, respectively, of the HEDG-4 receptor of clone pC3-hEdg4#36. FIG. 17B shows the alignment of the amino acid sequences of FIGS. 16A, 16B and the rat EDG-4.

EXAMPLE 15A

S1P Activation and Functional Response of the Cloned Human EDG-4 Receptor

To determine whether the newly identified human EDG-4 gene product, like its rat counterpart, can respond to SPC via activation of a serum response element (SRE) reporter gene, the expression clone pC3-hedg4#36 was transfected into 293-EBNA cells together with a luciferase reporter bearing 2 copies of a consensus binding sequence for serum response factor. Transfection was accomplished using the Lipofectamine Plus kit (Life Technologies, Cat. 10964-013), using the manufacturer's recommended conditions. Optimal SRE induction was seen when cells were seeded so as to become 100% confluent at the time of treatment, 72–96 hr after transfection. The cells were serum-starved in medium with 0% to 0.15% serum for the last 72 hr before treatment, then treated in serum-free medium for 6 hr with 3 $\mu$M SPC, or with serum-free medium alone. Under these conditions, a control cotransfection with empty expression vector pcDNA3 gave about 2.5-fold induction of the SRE reporter, suggesting that a low level of S1P/SPC receptor was expressed endogenously by the 293-EBNA cells. Human EDGE expression, in contrast, yielded a 26.3-fold induction of the SRE reporter gene by 3 $\mu$M SPC (FIG. 18A). Similarly, rat edg4 cotransfection with the SRE reporter gave a 35.6-fold induction of luciferase activity with 3 $\mu$M SPC. Thus, the human edg-4 cDNA encodes a functional S1P/SPC receptor, whose expression can be readily detected in 293-EBNA cells.

EXAMPLE 15B

Determination of Relative Potency and Efficacy of Human EDG-4 Receptor Agonists

One aspect of the present invention is a method for using recombinant human EDG-4 receptors in drug screening programs. Although the use of GPCRs in high-throughput screening is well known, no such screen has been reported for any edg receptor. More specifically, the novel human EDGE receptor presented herein can be used to identify and rank the relative potency and efficacy of potential agonists. These compounds may be useful inasmuch as they would be expected to trigger the survival-related signal transduction pathways associated with NF-κB induction. Equally, once a quantitative and reliable assay is established, it can readily be applied to identify and rank the relative potency and efficacy of receptor antagonists. This application, without limiting other aspects, of the screening methods described herein is specifically contemplated and incorporated within the scope of this invention.

Transfection of EDG-4, expression, pretreatment and treatment of 293-EBNA cells expressing recombinant human EDG-4 was carried out essentially as described in "Example 11. Heterologous Expression studies using Luciferase Assay." Various concentrations of S1P, SPC, psychosine, glucopsychosine or dihydrosphingosine 1-phosphate (dihydro-S1P) were applied in triplicate to cells in 96-well plates, and luciferase levels were measured after 6 hr treatment. Results were tabulated in Microsoft Excel, and analyzed with GraphPad Prism software. $EC_{50}$ values were determined using a fixed Hill-slope equation, unless variable slope significantly improved the fit to the data. The luciferase response was expressed as fold response, after subtracting any endogenous response in pcDNA3-transfected cells at a given concentration of compound. The experiment was repeated three times with similar results, and a representative experiment is shown in FIG. 18B.

Results: Table 2 summarizes the relative potency and efficacy of the compounds tested.

| Compound | $EC_{50}$ ($\mu$M) | Rank | Max. Fold | $E_{Max}$ (Percent) | Rank |
|---|---|---|---|---|---|
| S1P | 0.32 | 1 | 5.60 | 86.7 | 2 |
| SPC | 0.88 | 3 | 5.77 | 100 | 1 |
| Psychosine[a] | >10 | 4 | 1.78 | 30.9 | 5 |
| Glucospychosine[a] | >10 | 4 | 1.81 | 31.4 | 4 |
| Dihydro-S1P | 0.53 | 2 | 2.84 | 49.2 | 3 |

[a]Cytotoxicity was seen at 10 $\mu$M or higher concentrations, preventing quantitative determination of $EC_{50}$ or $E_{Max}$ Results: From the results obtained here, it can be concluded that EDG-4 responds to both S1P and SPC as full agonists with similar potency and efficacy. In contrast, dihydro-S1P was a partial agonist under these assay conditions, despite an apparent potency similar to S1P and SPC. Thus, while the addition of a choline substituent to the phosphate headgroup did not greatly affect activity, the unsaturated carbon-carbon bond appears to play a role for full agonist activity. Psychosine and glucopsychosine both showed poor potency and efficacy, as well as cytotoxicity at higher concentrations. Nonetheless, these compounds did activate the receptor (since pcDNA3 activity was set to 1.0 at each concentration). Published literature supports the existence of multiple receptors for S1P, and the identity of at least some of these with SPC receptor subtypes.

EXAMPLE 16

Role of Inflammatory lysolipid Receptors in Nerve Growth Factor-mediated Inflammation and Neurotronhic Signal Transduction The use of sphingosine 1-phosphate (S1P) in suppressing programmed cell death is known (Cuvillier et al., 1996; Spiegel, 1998). However, since S1P was presumed to act as an intracellular second messenger, no receptor-based data were presented. Our own work shows that the G protein-coupled receptors (GPCRs) EDG-1 (Hla & Maciag, 1990), EDG-3 (Yamaguchi et al., 1996), EDGA-4 (referred to in published literature as AGR16 [Okazaki et al., 1993] or H218 [MacLennan et al., 1994]) and HEDG-4 as cloned herein, and EDG-7 (Munroe et al., unpublished; corresponding U.S. Ser. No. 60/070,185, incorporated herein by reference) respond to S1P and sphingosylphosphorylcholine (SPC) as an agonist. However, as shown in the previous examples and in Example 18 below, only two of the four S1P/SPC receptors signal through activation of NF-κB: EDG-3 and EDG-4. S1P has multiple biological activities including mitogenesis, neurite retraction, inhibition of cell motility, suppression of apoptosis and as we have found, inflammatory gene expression. Therefore, successful therapeutic use of S1P or its analogs hinges on recognizing which receptors are expressed, and what their function(s) are in tissues exposed to the agent.

Direct modulation of NF-κB activation cascades has been proposed as a therapeutic mechanism for inflammation or apoptosis. However, NF-κB plays a vital role in innate immunity against ubiquitous microbial pathogens and in mobilizing the antigen-specific immune system. Therefore, rather than targeting this irreplaceable defense system, it would be preferred to instead block inappropriate activation of NF-κB through inflammatory S1P/SPC receptors, in situations where their agonists and/or receptor signaling are excessive or inappropriate. Alternatively, where NF-κB could prevent unwanted apoptosis or could enhance immune function in immunocompromised hosts, agonists of these receptors would be desirable, especially with favorable medicinal chemistry properties and selective pharmacology.

Because the sphingosine-phosphorylating enzyme sphingosine kinase (Edsall et al., 1997) and NF-κB (Rius et al., 1997) have both been shown to play critical roles in the neurotrophic action of NGF in the well-defined PC12 neuroblastoma model, we can surmise that the anti-apoptotic signaling pathway of NGF depends on both S1P and NF-κB. EDG-4 has been shown to be expressed in PC12 cells before, during and after NGF treatment (MacLennan et al., 1994). In CNS, the highest levels of edg-4 RNA are detected during embryogenesis. Immunohistochemical localization of CNS EDG-4 protein labels cell bodies and axons to young, differentiating neurons, consistent with the proposed role in neurotrophic function (MacLennan et al., 1997).

Since EDG-4 responds to S1P/SPC by activating NF-κB, it can be predicted that a causal link between S1P production (Edsall et al., 1997) and NF-κB activity (Rius et al., 1997) exists in PC12 cells. EDG-3, if expressed, could play a similar role. Although many steps in NGF signaling have been described, no report exists which links S1P to NF-κB in this system. In U937 cells, a single report does show that S1P treatment resulted in NF-κB activation (Shatrov et al., 1997). However, the authors did not show whether inflammatory gene expression such as IL-8 or IL-6 resulted, nor did they realize that a cell-surface receptor could be involved. Instead they assumed that S1P is an intracellular second messenger, as indeed did U.S. Pat. No. 5,712,262 (Cuvillier et al., 1996; Spiegel, 1998). We have now provided a molecular explanation of the link between these signaling steps. S1P acts on an inflammatory receptor subtype such as EDG-4 or EDG-3. This in turn leads to the activation of the $G_{i/o}$ heterotrmeric protein complex, triggering downstream events that depend on tyrosine kinase(s) and reactive oxygen species. Finally, NF-κB is activated, resulting in anti-apoptotic gene expression.

Two receptors exist for NGF on PC12 cells and many other neuronal and non-neuronal cell types. One of these, TrkA, is a high-affmity NGF receptor which signals through a classical dimeric transmembrane tyrosine kinase receptor mechanism. The other, $p75^{NGFR}$, is a low affinity receptor for NGF and several other neurotrophins, belongs to the "death receptor" gene family including TNFR, Fas/CD95 and CD28, and signals through a sphingomyelinase pathway using ceramide and/or sphingosine as key pro-apoptotic intermediates. In fact, $p75^{NGFR}$ expression in the absence of TrkA causes NGF to induce apoptosis, rather than survival of PC12 cells. TrkA co-expression with $p75^{NGFR}$ is required for NGF to display neurotrophic activity in PC12 cells; expression of TrkA alone is without effect on apoptosis.

Without wishing to be bound by theory, it appears that TrkA confers neurotrophic activity on NGF as follows. Sphingosine kinase (SK) is an enzyme that converts the proapoptotic sphingosine into S1P. S1P has been shown to actively suppress programmed cell death induced by death receptor ligands or ceramide (Cuvillier et al., 1996; Spiegel, 1998). SK is induced by NGF in PC12 cells that co-express TrkA and p75NGFR, but not when the tyrosine kinase activity of TrkA is inhibited with K252a (Edsall et al., 1997). Therefore, it appears that the induction of sphingosine kinase converts a $p75^{NGFR}$ death signal (ceramnide/sphingosine) into a survival signal (S1P). Given the presence of EDG-4 (and perhaps EDG-3) in PC12 cells, the production of S1P via sphingosine kinase would be expected to lead to activation of the GPCR, thereby activating NF-κB. NF-κB, in turn, is already known to be essential for neurotrophic responses to NGF (Rius et al., 1997). Thus, inflammatory S1P receptors play a pivotal role in directly linking these two essential steps in NGF neurotrophic signaling.

Like $p75^{NGFR}$, several other death receptors have been shown to induce apoptosis and/or NF-κB activation, depending on the cell type and costimulus applied. The involvement of sphingomyelinase, ceramide/sphingosine and sphingosine kinase in the signaling cascade has also been shown repeatedly with TNFR, Fas/CD95 and other family members. Another parallel with the NGF system is the observation that some cell types that express a given death receptor survive their ligands while other do not. Again, protein kinase C is implicated in survival pathways. There is even direct evidence that S1P plays a similar role in survival for Fas/CD95 and in inflammatory gene expression for TNFR. Therefore, one can predict a widespread role for inflammatory lysosphingolipid/edg receptors in modulating the apoptotic/inflammatory potential of death receptor ligands. If true, these GPCRs may play a fundamental role in cell survival, differentiation, and inflammation. Therefore, methods for isolating such receptors, and for identifying ligands that modulate these activities constitute aspects of the invention described herein.

The ligands for other GPCRs known to activate NF-κB are generally peptides or small molecules produced in a very limited range of cell types. However, the sphingolipids and sphingomyelinase which are ubiquitously distributed can be used to generate ligands for the edg receptors. Therefore, potentially every cell type can make ligands for these receptors. Moreover, ceramide and/or sphingosine are synthesized as an integral part of the death receptor signaling pathways, so that survival may require as little as a single additional metabolic conversion to S1P, provided the appropriate S1P receptors are present. While TrkA provides the signal to induce SK in PC12 cells, other inducers of protein kinase C have also been shown to induce SK expression. One of these is the potent tumor promoter phorbol ester. Thus, other costimulators may dramatically change or even reverse the outcome of death receptor signaling through the inflammatory S1P/SPC receptors.

Screening of individual S1P/SPC receptors will permit the identification and optimization of selective ligands for use in modulating apoptosis and inflammation. For example, SPC shows greater activity than S1P acting on EDG-4, whereas the 2 compounds have similar activity on the EDG-3 receptor. While anti-apoptotic compounds directed at these targets are difficult to identify without the receptor assays, selective pro-apoptotic compounds are even harder to target, since many enzyme inhibitors can trigger apoptotic pathways. Furthermore, since it now appears that edg receptor-induced NF-κB is one mechanism by which S1P suppresses apoptosis, inflammatory gene expression is also expected to occur. A further implication is the potential for immune stimulation with EDG-3 or EDGY agonists, including S1P and SPC. Antagonists, on the other hand, could be used to treat transplant rejection or autoimmune diseases, in which both inflammatory responses and insufficient apoptosis of auto/alloreactive T cells play a role.

EXAMPLE 17

Three Inflammatory Subtypes of Lysophosphatidic Acid (LPA) Receptor

LPA, like S1P, is abundant in serun, but not plasma. Moreover, LPA is produced as a consequence of phospholipase $A_2$ with or without the contribution of phospholipase D (depending on the phospholipid substrate). Our results showing IL-8 production in HUVEC exposed to 5 μM LPA further suggest that inflammatory responses could be mediated by. some, or all, LPA receptors. To date we have identified three subtypes of edg receptors that respond to LPA as an agonist. These are EDG-2, EDG-6 and EDG-5 (referred to also as $LP_{A1}$, $LP_{A2}$ and $LP_{A3}$, respectively (Chun, J, Contos, J J A and Munroe, D G. 1998. A growing family of receptor genes for lysophosphatidic acid (LPA) and other lyso-phospholipids. Cell Biochem Biophys (in press)). The EDG-5 receptor is set out in co-pending U.S. application Ser. No. 08/997,803 to MLUNROE et al., incorporated herein by reference and the amino acid sequence and cDNA sequence for the EDG-6 receptor is set out in FIGS. 21 and 22, respectively. To determine whether these receptors might mediate inflammatory responses, each was cotransfected separately with SRE, NF-κB or AP-1 reporter genes. The AP-1 reporter contained approximately 1 kb of the human collagenase II promoter, and the first 50 bp of the 5'-untranslated region of the collagenase II transcription unit(Angel P, et al. 1987. Phorbol ester-inducible genes contain a common cis element recognized by a TPA-modulated trans-acting factor. Cell 49:729–739), a region whose inducible expression has been shown to be controlled by AP-1. This transcription factor, like NF-κB has been implicated in inflammatory and neoplastic signal transduction., though the gene targets of its action are largely distinct from those of NF-κB (Adcock IM. 1997. Transcription factors as activators of gene transcription: AP-1 and NF-κB. Monaldi Arch Chest Dis 52:178–186. Review).

293-EBNA cells were grown, lipofected in monolayer cultures, and pretreated as described above for Example 11, assay #1, except that NF-κB and AP-1 reporter-transfected cells were pretreated for 6 hr in medium containing 0.5% FBS, then treated overnight in the same medium with or without 10 μM LPA.

Results: As shown in FIG. 23, all three receptors robustly activated the NF-κB reporter (about 3–4-fold) in the presence of 10 μM LPA, while no response to LPA was seen when the NF-κB reporter was cotransfected with the empty expression vector pcDNA3. With the SRE and AP-1 reporter genes, some endogenous response to LPA was seen (about 1.5-fold vs untreated control cells). However, EDG-6 strongly induced both reporters, while EDG-2 and EDG-5 caused greater than 2-fold induction of the SRE and AP-1 reporters with LPA. Therefore, all three LPA receptors tested here are capable of inducing inflammatory gene transcription through NF-κB , and perhaps, AP-1 as well. As mentioned, these two inflammatory transcription factors respond to different signaling pathways by inducing distinct gene sets. However, some genes are powerfully and synergistically activated by both factors acting in concert (Stein B, et al. 1993. Cross-coupling of the NF-κB p65 and Fos/Jun transcription factors produces potentiated biological function. EMBO J 12:3879–3891). Thus, the LPA receptors EDG-2, EDG-5 and EDG-6 are likely to respond to LPA or other lysolipid agonists by activating one or both sets of gene targets controlled by NF-κB and AP-1. Since phospholipase action and NF-κB/AP-1 activation are common features of many diseases with an inflammatory or immune component, it is also possible that edg/LPA receptors exacerbate a pre-existing disease or injury through their inflammatory responses to lysolipids. Therefore, antagonists of one or more of these inflanmnatory receptors could be useful in treating such diseases. Without limiting the intended scope of the inventions disclosed, examples include rheumatoid arthritis, stroke, neurotrauma, Alzheimer's disease, ALS, asthma, endotoxic shock, atherosclerosis and many other diseases. Besides inflammation, activation of NF-κB is likely to promote survival in the face of pro-apoptotic signals, for example, those initiated by the TNF receptors or other "death receptors". (Van Antwerp D J, et al. 1998. Inhibition of TNF-induced apoptosis by NF-κB. Review. Trends Cell Biol 8:107–111) This may explain the observed reduction in efficacy of chemotherapy-induced apoptosis in LPA-treated ovarian cancer cells.(Frankel A, et al. 1996. Peptide and lipid growth factors decrease cis-diamminedichloroplatinum-induced cell death in human ovarian cancer cells. Clin Cancer Res 2:1307–1313) With the present disclosure, antagonists of inflammatory LPA receptors may be discovered and optimized to reduce or delay the emergence of cancer cell populations immune to the apoptosis-inducing effects of chemotherapeutics. Such therapies may also be used to treat autoimmunity or other diseases where excessive or inappropriate cell survival occurs. Alternatively, agonists of inflammatory LPA receptors may be neuroprotective, or promote survival of other cell types in diseases where inappropriate or excessive cell death occurs. Examples include HIV/AIDS, myelodysplasia, endotoxic shock, cirrhosis of the liver, to name a few.

EXAMPLE 18

Calcium Microfluorimetry as a Real-time Readout of EDG Receptor Functional Responses Reporter gene assays, while very useful, produce an endpoint assay result, and therefore cannot give information about transient, reversible or desensitizing responses initiated by EDG receptors. Calcium microfluorimetry is one example of an alternative approach that does allow such information to be gathered. Since $Ca^{2+}$ responses to S1P or LPA have been observed in cells that endogenously express their receptors (Tomquist K, et al. 1997. Sphingosine 1-phosphate mobilizes sequestered calcium, activates calcium entry, and stimulates deoxyribonucleic acid synthesis in thyroid FRTL-5 cells. Endocrinology 138:4049–4057; Holtsberg F W, et al. 1997. Lysophosphatidic acid induces a sustained elevation of neuronal intracellular calcium. J Neurochem. 69:68–75) we tested 293-EBNA cells transiently transfected with different EDG receptors for functional responses via calcium microfluorimetry.

Transfections were carried out with EDG receptors in 293-EBNA cells as described above, except that no reporter gene vector was included in the DNA mix. Two days after transfection, cells were harvested by trypsinization and plated at a density of 200,000 cells onto poly-D-lysine-coated coverslips in 100 μl of medium containing 0.5% FBS. After briefly allowing cell attachment to take place, 2 ml of medium without FBS was added and the cells were incubated overnight. The next day, cells were loaded with 5 μM fura-2 AM ester (Molecular Probes) for 60 min at RT, then washed and used for calcium microfluorimetry. S1P was prepared as a 10 mM stock in 100% ethanol and diluted to a final concentration of 2 μM in ACSF; PMA was used at a final concentration of 25 ng/ml. Treatments were applied using a gravity-fed perfusion apparatus. Fluorescence emission was continuously monitored and recorded with PTI 2.060a software and analyzed with Sigma Plot software. Intracellular calcium concentrations were calculated by interpolation on a ratiometric fluorescence curve generated from fura-2 fluorescence in a calcium dilution series.

Figure 20:
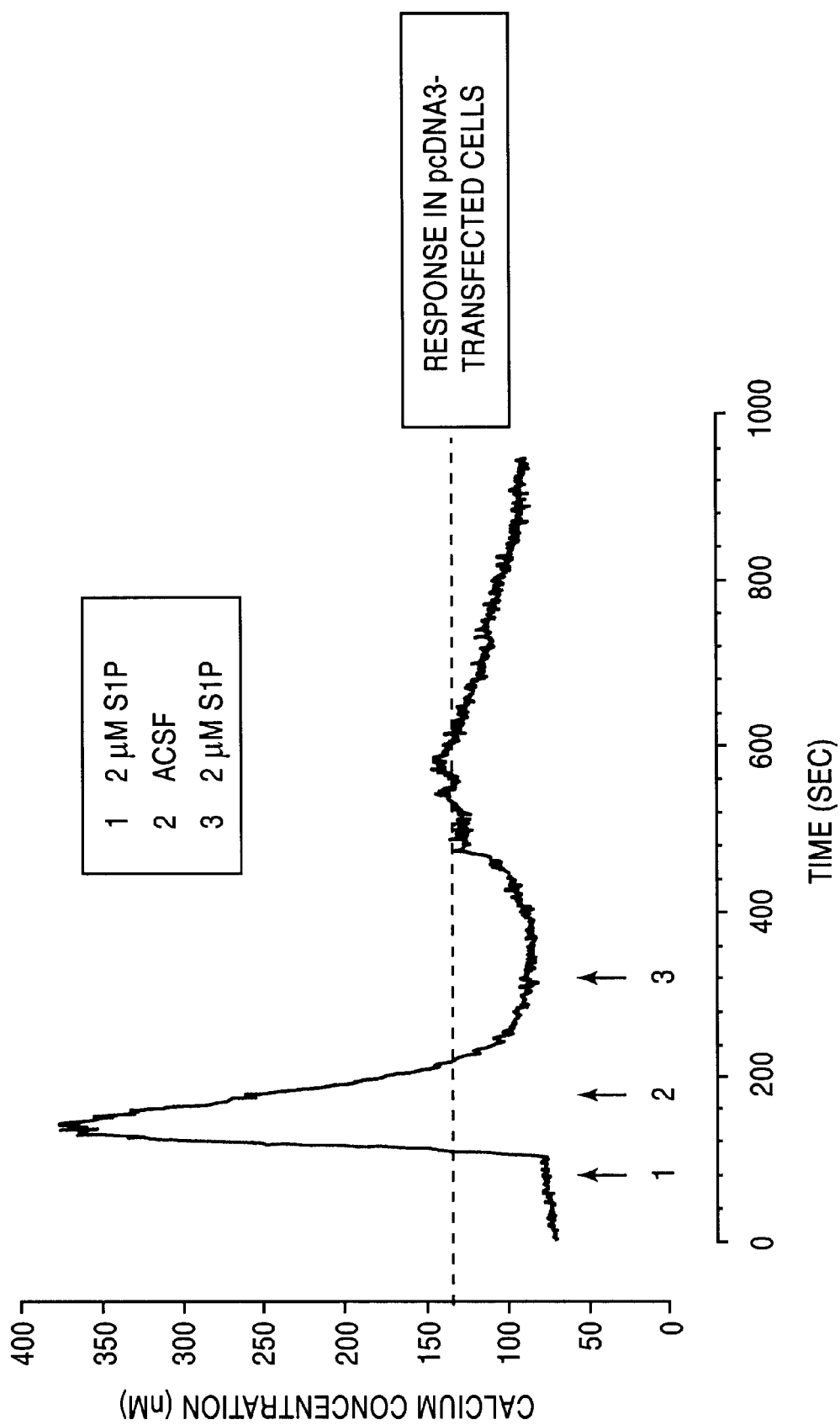
FIG. 20 illustrates the intracellular calcium response to S1P in cells transfected with human EDG-3 expression vector.

Results: FIG. 19 shows the response of control cells transfected with pcDNA3 and treated with 2 μM S1P. A small increase in intracellular calcium concentration was observed with 2 μM S1P, and this response completely desensitized the response to a second application of S1P. FIG. 20 shows the calcium response to S1P in EDG-3 transfected cells. In contrast to the approximantely 60 mM change in intracellular calcium in pcDNA3-transfected cells, a 300 nM increase was observed in EDG-3 transfected cells treated with 2 μM S1P. A second application of S1P elicited a small response, though desensitization clearly occurred. The Table below shows a qualitative analysis of preliminary data we have obtained from cells expressing each EDG receptor, after addition of the appropriate agonist at a 2 or 10 μM concentration.

TABLE 3

Qualititative calcium response of EDG-transfected cells to receptor agonists.

| Receptor | Agonist | Concentration | Response |
|---|---|---|---|
| EDG-1 | S1P | 2 and 10 μM | None within 20 min |
| EDG-2 | LPA | 10 μM | ++ |
| EDG-3 | S1P | 2 and 10 μM | +++ |
| EDG-4 | S1P | 2 and 10 μM | +++ |
| EDG-5 | LPA | 2 and 10 μM | +++ |
| EDG-6 | LPA | 2 and 10 μM | +++ |
| EDG-7 | S1P | 2 and 10 μM | None within 20 min |

While further experiments are required to quantitatively assess the capacity of these receptor subtypes to elevate intracellular calcium, initial results strongly suggest a correlation of calcium signaling with induction of inflammatory response pathways. Supporting this conclusion, EDG-1 and EDG-7 both respond through the SRE reporter to S1P, yet fail to signal through NF-κB reporters or increases in intracellular calcium. The fact that only two of the four identified S1P receptors signal through NF-κB indicates that effective anti-inflammatory or survival-modulating therapeutics can best be developed using the inventions disclosed herein, which specifically measure the relevant receptor subtypes and pathways as indicators of therapeutic efficacy. Therefore, NF-κB reporter genes, other endpoint assays that measure inflammatory signal transduction or gene expression, and real-time functional assays that monitor inflammatory signaling by edg/LL receptors are specifically encompassed within the scope of the present invention.

EXAMPLE 19

Construction and Functional Testing of a Human EDG-4 Fusion Protein with Jellyfish Green Fluorescent Protein (GFP)

Chimeric proteins may be used to study the structure, function, mechanism of activation or biological role of a protein. In the case of edg receptors, little is known of their intracellular trafficking, post-translational processing, or physical interaction with other proteins. The green fluorescent protein (GFP) from *Aequorea victoria* has been used as a tool for the direct visualization of various fusion proteins in living cells, since no fixation or substrate addition is required to obtain fluorescence. Numerous examples exist of different proteins that retain function after fusion to GFP, including at least some GPCRs. (Kallal L, et al. 1998. Visualization of agonist-induced sequestration and down-regulation of a green fluorescent protein-tagged beta2-adrenergic receptor. J Biol Chem 273:322–328). To address of questions of EDG-4 trafficking and protein-protein interactions, we constructed a GFP fusion with human EDG-4 cDNA and tested for a functional response to S1P using the SRE reporter gene as a readout.

A pair of primers was designed from two ends of reading frame of human edg-4 cDNA sequence to engineer the edg-4 open reading frame into a vector designed for GFP fusion protein expression, with the GFP tag carboxy-terminal to the full-length EDG-4 polypeptide:

5'-End Primer: Contains Site for Kpn I enzyme, and optimized (Kozak) translation initiation sequence:
HE4-ATG KpnF: [5'-TTTAAAGGTACCGCCACCATGGGCA GCT TGTAC-3']

3'-End Primer: Contains site for XbaI enzyme, and lacks naturally-occurring edg-4 stop codon:
HE4-xba/1096R: [5'-TATATATCTAGAGACCACCGTGTTGCC CTCCAG-3']

pc3-hedg4#36 plasmid DNA was amplified with the above pair of primers under the following conditions of PCR amplification, using the Expand™ PCR system from Boehringer Mannheim (Cat. 1681-842).

The reaction contained the following reagents:

5 μl of 10× PCR Buffer 3

1.0 μl of 25 mM dNTP mix 1.5 μl of Primer HE4-ATG KpnF (10 μM)

1.5 μl of Primer HE4-xba/1096R (10 μM)

0.75 μl of Enzyme (2 units)

39.25 µl water
1µl DNA

| PCR conditions: | |
| --- | --- |
| Incubate: | 94° C. for 2 min |
| 10 cycles: | 94° C. for 1 min |
| | 50° C. for 1 min |
| | 68° C. for 2 min |
| 20 cycles: | 94° C. for 1 min |
| | 68° C. for 3 min |
| Incubate: | 68° C. for 8 min |
| Hold: | 4° C. |

The amplified reaction (designated as sample 80727-3) was purified using QIAquick PCR purification kit (Qiagen Cat.28106). The DNA was restricted with KpnI and Xba I enzymes, and subcloned into Kpn I and XbaI restricted pcDNA3.1/CT-GFP (Invitrogen, Cat K4820-01). Three positive clones i.e. E4-GFP#8-3, E4-GFP#15-3, E4-GFP#17-3 were identified, sequenced to confirm the expected insert and cloning junction, and tested by lipofection into 293-EBNA cells as described above for human edg-4 cDNA.

Figure 24:
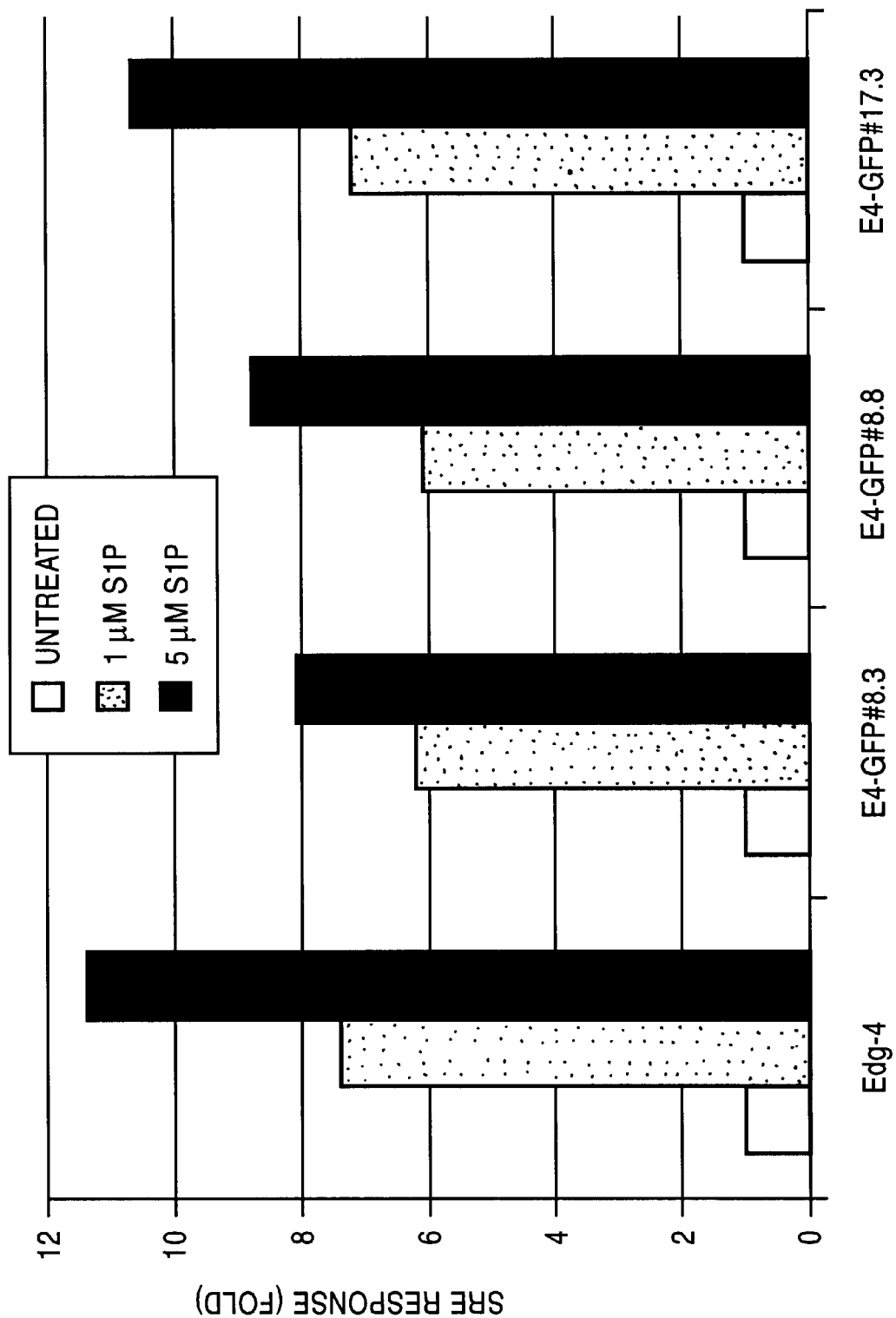
FIG. 24 illustrates the SRE Response for a human EDG-4 fusion protein with Jellyfish Green Fluorescent Protein (GFP).

Results: Cells were observed under fluorescence microscopy using a fluorescein filter set. Cells expressing the EDG-4/GFP fusion protein were easily identified due to their bright green fluorescence. In untreated, serum-starved cells most of the fluorescence was peripherally located, apparently at the plasma membrane. However, 72 hr after transfection, high levels of the GFP fusion protein accumulated in discrete clusters which might be "capped" on the cell surface or, alternatively, internalized in vesicles. A control transfection with a nonfusion GFP construct revealed only a diffuse cytoplasmic localization of GFP fluorescence. Importantly, the EDG-4/GFP receptors could be directly visualized in living cells without special fixing or development. Thus, trafficking and interaction of EDG-4/GFP with various organelles may be followed in living cells before, during and after addition of agonists and/or pharmacological treatments. Such localization would only be meaningful, of course, if the receptors bind ligands and activate signal transduction pathways normally. Results of SRE reporter gene cotransfection and response to 1 or 5 µM S1P are shown in FIG. 24. All 3 clones of EDG-4/GFP did not differ significantly from the EDG-4 parent is expression vector in SRE response to S1P. Thus, despite the fairly large fusion domain presented by GFP, apparently normal ligand-responsiveness and intracellular signaling was retained. Visualization and quantitation of fusion receptor internalization offers an alternative means of assessing functional activation of the EDG-4 receptor, for example, in pharmacological evaluation of partial agonists of EDG-4.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments.

References

An, S, Bleu, T, Huang, W, Hallmark, O G, Coughlin, S R and Goetzl, E J. 1997. Identification of cDNAs encoding two G protein-coupled receptors for lysosphingolipids. FEBS Lett 417: 279–282.

Carter, B D, Kaltschmidt, C, Kaltschmidt, B, Offenhauser, N, Bohm-Matthaei, R, Baeuerle, P and Barde, Y-A. 1996. Selective activation of NF-κB by nerve growth factor through the neurotrophin receptor p75. Science 272: 542–545.

Cuvillier, O, Pirianov, G, Kleuser, B, Vanek, P G, Coso, O A, Gutkind, J S and Spiegel, S. 1996. Suppression of programmed cell death by sphingosine-1-phosphate. Nature 381: 800–803.

Cuvillier, O, Rosenthal, D S, Smulson, M E and Spiegel, S. 1998. Sphingosine 1-phosphate inhibits activation of caspases that cleave poly(ADP-ribose) polymerase and lamins during Fas- and ceramide-mediated apoptosis in Jurkat T lymphocytes. J Biol Chem 273: 2910–2916.

Edsall, L C, Pirianov, G G and Spiegel, S. 1997. Involvement of sphingosine 1-phosphate in nerve growth factor-mediated neuronal survival and differentiation. J Neurosci 17: 6952–6960.

Hla, T and Maciag, T. 1990. An abundant transcript induced in differentiating human endothelial cells encodes a polypeptide with structural similarities to C-protein-coupled receptors. J Biol Chem 265: 9308–9313.

Lee, M-J, Van Brocklyn, J R, Thangada, S, Liu, C H, Hand, A R, Menzeleev, R, Spiegel, S and Hla T. Sphingosine-1-phosphate as a ligand for the G protein-coupled receptor EDG-1. Science 279: 1552–1555.

MacLennan, A J. 1996. Molecular cloning and expression of G-protein coupled receptors. U.S. Pat. No. 5,585,476. Issued Dec. 17, 1996.

MacLennan, A J, Browe, C S, Gaskin, A A, Lado, D C and Shaw, G. 1994. Cloning and characterization of a putative G-protein coupled receptor potentially involved in development. Mol Cell Neurosci 5: 201–209.

MacLennan, A J, Marks, L, Gaskin, A A and Lee, N. 1997. Embryonic expression pattern of H218, a G-protein coupled receptor homolog, suggests roles in early mammalian nervous system development. Neuroscience 79: 217–224.

Okazaki, H, Ishizaka, N, Sakurai, T, Kurokawa, K, Goto, K, Kumada, M and Takuwa, Y. 1993. Molecular cloning of a novel putative G protein-coupled receptor expressed in the cardiovascular system. Biocehm Biophys Res Commun 190: 1104–1109.

Rius, R A, Edsall, L C and Spiegel, S. 1997. Activation of sphingosine kinase in pheoclromocytoma PC12 neuronal cells in response to trophic factors. FEBS Lett 417: 173–176.

Shatrov, V A, Lehmann, V and Chouaib, S. 1997. Sphingosine-1-phosphate mobilizes intracellular calcium and activates transcription factor NF-κB in U937 cells. Biochem Biophys Res Commun 234: 121–124.

Spiegel, S. 1998. Use of sphingosine-1-phosphate to suppress programmed cell death. U.S. Pat. No. 5,712,262. Issued Jan. 27, 1998.

Taglialatela, G, Robinson, R and Perez-Polo, J R. 1997. Inhibition of nuclear factor kappa B (NFκB) activity induces nerve growth factor-resistant apoptosis in PC12 cells. J Neurosci Res 47: 155–162

Yamaguchi, F, Tokuda, M, Hatase, O and Brenner, S. 1996. Molecular cloning of the novel human G protein-coupled receptor (GPCR) gene mapped on chromosome 9. Biochem Biophys Res Commun 227: 608–614.

Zondag, G C M, Postma, F R, van Etten, I, Verlaan, I and Moolenaar, W H. 1998. Biochemi J 330

The embodiments of the invention in which an exclusive property or privilege is claimed are defined as follows:

1. An isolated polynucleotide that codes for an endothelial differentiation gene (EDG) receptor, said EDG receptor comprising the amino acid sequence, selected from the group consisting of: (a) the amino acid sequence comprising SEQ ID NO:2 and (b) the amino acid sequence comprising SEQ ID NO:4.

2. An isolated polynucleotide according to claim 1 that codes for an EDG receptor of the amino acid sequence comprising the amino acids of SEQ ID NO: 2.

3. An isolated polynucleotide according to claim 1 that codes for an EDG receptor of the amino acid sequence comprising the amino acids of SEQ ID NO): 4.

4. An isolated polynucleotide according to claim 1 comprising the nucleotide sequence comprising nucleotides 38–1099 of SEQ ID NO: 1.

5. An isolated polynucleotide according to claim 1 comprising the nucleotide sequence of SEQ ID NO: 3.

6. A vector comprising a polynucleotide according to claim 1.

7. A vector according to claim 6 comprising a polynucleotide that codes for an EDG receptor of the amino acid sequence comprising the amino acids of SEQ ID NO: 2.

8. A vector according to claim 6 comprising a polynucleotide that codes for an EDG receptor of the amino acid sequence comprising the amino acids of SEQ ID NO: 4.

9. A cell that has been genetically engineered to produce an EDG receptor wherein said cell has incorporated expressibly therein a polynucleotide as defined in claim 1.

10. A cell according to claim 9 wherein said cell has incorporated expressibly therein a polynucleotide that codes for an EDG receptor of the amino acid sequence comprising the amino acids of SEQ ID NO: 2.

11. A cell according to claim 9 wherein said cell has incorporated expressibly therein a polynucleotide that codes for EDG receptor of the amino acid sequence comprising the amino acids of SEQ ID NO: 4.

12. A membrane preparation obtained from a cell as defined in claim 9.

13. A membrane preparation obtained from a cell as defined in claim 10.

14. A membrane preparation obtained from a cell as defined in claim 11.

15. An isolated EDG receptor comprising the amino acid sequence of SEQ ID NO: 2.

16. An isolated EDG receptor comprising the amino acid sequence of SEQ ID NO: 4.

* * * * *